United States Patent
Sohda et al.

[11] Patent Number: 5,932,601
[45] Date of Patent: Aug. 3, 1999

[54] OXAZOLIDINEDIONE DERIVATIVES, THEIR PRODUCTION AND USE

[75] Inventors: Takashi Sohda, Takatsuki; Hiroyuki Odaka, Kobe; Yu Momose, Takarazuka; Mitsuru Kawada, Amagasaki, all of Japan

[73] Assignee: Takeda Chemical Industries, Ltd., Osaka, Japan

[21] Appl. No.: 08/550,289

[22] Filed: Oct. 30, 1995

[30] Foreign Application Priority Data

Nov. 2, 1994 [JP] Japan .................................. 6-269826
Jul. 7, 1995 [JP] Japan .................................. 7-171768
Aug. 29, 1995 [JP] Japan .................................. 7-220942

[51] Int. Cl.$^6$ .................................................. A61K 31/42
[52] U.S. Cl. .......................... 514/376; 548/226; 548/235; 548/169; 514/365; 514/340; 546/271.4
[58] Field of Search ............................... 514/376; 548/226

[56] References Cited

U.S. PATENT DOCUMENTS

| | | | |
|---|---|---|---|
| 4,332,952 | 6/1982 | Schnur | 548/226 |
| 4,342,771 | 8/1982 | Schnur | 546/152 |
| 4,430,337 | 2/1984 | Holland | 514/376 |
| 4,725,610 | 2/1988 | Meguro et al. | 514/369 |
| 5,391,565 | 2/1995 | Hindley | 514/375 |
| 5,468,762 | 11/1995 | Malamas et al. | 514/376 |
| 5,478,852 | 12/1995 | Olefsky et al. | 514/376 |
| 5,498,621 | 3/1996 | Dow | 514/369 |
| 5,614,544 | 3/1997 | Sohda | 514/376 |
| 5,665,748 | 9/1997 | Sohda et al. | 514/365 |
| 5,728,720 | 3/1998 | Shinkai | 514/374 |
| 5,739,345 | 4/1998 | Fujita | 548/226 |
| 5,834,501 | 11/1998 | Fujita | 548/226 |

FOREIGN PATENT DOCUMENTS

| | | |
|---|---|---|
| 0428312 | 5/1991 | European Pat. Off. . |
| 428 312 | 5/1991 | European Pat. Off. . |
| 0612743 | 8/1994 | European Pat. Off. . |
| 612743 | 8/1994 | European Pat. Off. . |
| 0 684 242 A1 | 11/1995 | European Pat. Off. . |
| 92-02520 | 2/1992 | WIPO . |
| 95/31454 | 11/1995 | WIPO . |

OTHER PUBLICATIONS

Burger, Ed Medicinal Chemistry 2d Ed, Interscience, New York, 1960 p. 43.
Dow et al. J. Med. Chem. vol. 34 pp. 1538–1544 (1991).
Sohda, J. Med. Chem., 1992, 35, pp. 2617–2626.

*Primary Examiner*—Donald G. Daus
*Attorney, Agent, or Firm*—Wenderoth, Lind & Ponack L.L.P.

[57] ABSTRACT

2,4-Oxazolidinedione derivative represented by the formula:

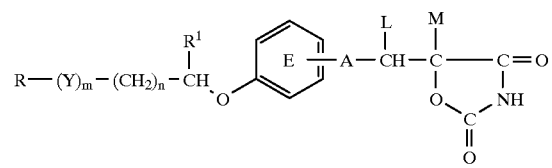

wherein R stands for an optionally substituted hydrocarbon residue or heterocyclic group; Y stands for a group represented by —CO—, —CH(OH)— or —NR$^3$— (wherein R$^3$ stands for an optionally substituted alkyl group); m is 0 or 1; n is 0, 1 or 2; A stands for a C$_{1-7}$ divalent aliphatic hydrocarbon group; R$^1$ stands for hydrogen or an alkyl group; ring E stands for a benzene ring having 1 or 2 substituents; L and M respectively stand for hydrogen, or L and M may optionally be combined with each other to form a bond; with a proviso that the partial formula:

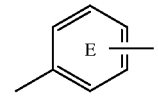

does not include the formula:

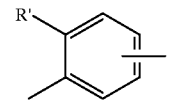

wherein R' stands for an alkyl group; or a salt thereof, which has excellent actions of lowering blood sugar and lipid in blood.

17 Claims, No Drawings

OXAZOLIDINEDIONE DERIVATIVES, THEIR PRODUCTION AND USE

FIELD OF THE INVENTION

This invention relates to a novel oxazolidinedione derivative having an action of lowering blood sugar and lipid in blood, to a method of producing it and to an agent comprising it for the therapy of diabetes, which is used in the field of pharmaceuticals.

BACKGROUND OF THE INVENTION

As remedies of diabetes, various biguanide compounds and sulfonylurea compounds have so far been used. However, biguanide compounds are hardly used at present, since they cause lactic acidosis, while sulfonylurea compounds, which have a strong action of lowering blood sugar, often cause severe hypoglycemia, requiring special attention in use. On the other hand, there are thiazolidinedione derivatives and oxazolidinedione derivatives known to have actions of lowering blood sugar and lipid in blood, which are free of such drawbacks.

For example, JPA H3(1991)-170478 and WO9202520-A1 describe, as 2,4-oxazolidinedione derivatives having substituents at the 5-position, a series of 5-(substituted benzyl)-2,4-oxazolidinedione derivatives, JPB S62(1987)-30993 describes 2,4-oxazolidinedione derivatives substituted with an alicyclic hydrocarbon group at the 5-position, and JPB S63(1988)-35632 describes 2,4-oxazolidinedione derivative substituted with, among others, a substituted aromatic ring at the 5-position.

SUMMARY OF THE INVENTION

The present inventors studied extensively on 2,4-oxazolidinedione derivatives, and found that novel derivatives having, as substituents at the 5-position of 2,4-oxazolidinedione ring, a divalent straight or branched carbon chain having, at its terminal, a substituted phenyl, e.g. 2-(substituted phenyl)ethyl group, 3-(substituted phenyl)propyl group, 4-(substituted phenyl)butyl group, 5-(substituted phenyl)pentyl group, etc., possess actions of lowering blood sugar and lipid in blood, thus the present invention being completed.

More specifically, the present invention relates to:
1. a 2,4-oxazolidinedione derivative represented by the formula:

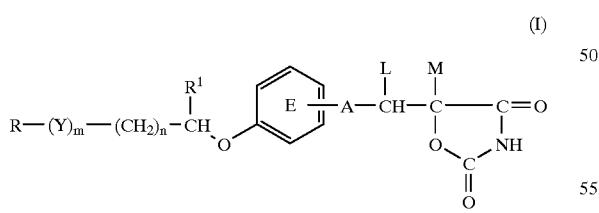

(I)

wherein R stands for an optionally substituted hydrocarbon residue or heterocyclic group; Y stands for a group represented by —CO—, —CH(OH)— or —NR$^3$— (wherein R$^3$ stands for an optionally substituted alkyl group); m is 0 or 1; n is 0, 1 or 2; A stands for a C$_{1-7}$ divalent aliphatic hydrocarbon residue; R$^1$ stands for hydrogen or an alkyl group; ring E stands for a benzene ring having 1 or 2 substituents; L and M respectively stand for hydrogen, or L and M may optionally be combined with each other to form a bond; with a proviso that the partial formula:

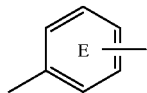

does not include the formula:

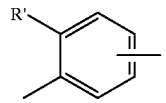

wherein R' stands for an alkyl group; or a salt thereof,
2. a pharmaceutical composition, comprising, as an effective component, a 2,4-oxazolidinedione derivative represented by the formula (I) or a pharmaceutically acceptable salt thereof, and
3. a method of producing a compound represented by the formula (I).

DETAILED DESCRIPTION OF THE INVENTION

The compounds represented by the above formula (I) include compounds represented by the following formulae:

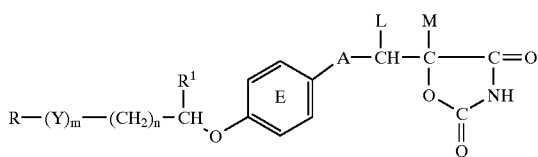

(I-A1)

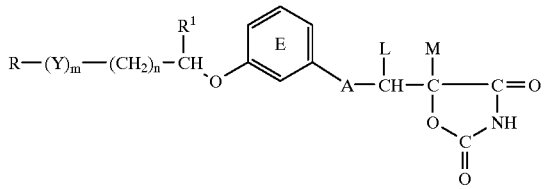

(I-A2)

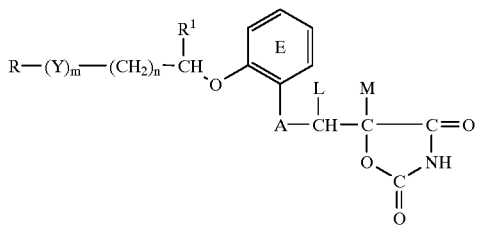

(I-A3)

wherein each symbol has the same meaning as defined above.

Among the compounds represented by the formulae (I-A1), (I-A2) and (I-A3), compounds represented by (I-A1) and (I-A2) are preferable, and compounds represented by (I-A1) are most preferable, in view of pharmacological activity and toxicity.

Compounds represented by the formula (I) wherein L and M are combined with each other to form a bond, are ones represented by the following formula:

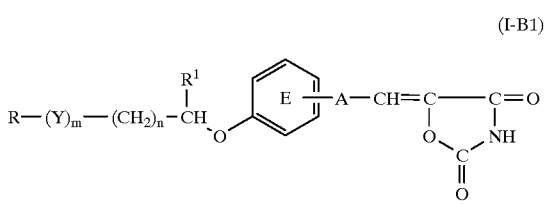

(I-B1)

wherein each symbol has the same meaning as defined above. And, compounds represented by the formula (I) wherein L and M are respectively hydrogen, are ones represented by the following formula:

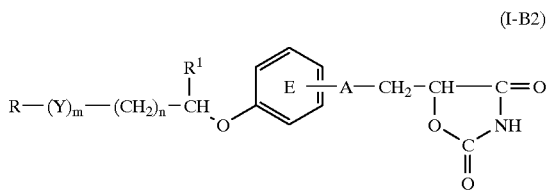

(I-B2)

wherein each symbol has the same meaning as defined above.

In the compounds represented by the above formula (I-B1), there exist (E)- and (Z)-isomers relative to the double bond at the 5-position of the oxazolidinedione ring.

In the compounds represented by the above formula (I-B2), there exist (R)- and (S)-optical isomers due to the asymmetric carbon at the 5-position of the oxazolidinedione ring. The compounds represented by the above formula (I-B2) include these (R)- and (S)-optical isomers and racemic isomers.

Among the compounds represented by the formulae (I-B1) and (I-B2), ones represented by the formula (I-B2) are preferable.

As the hydrocarbon residue in the optionally substituted hydrocarbon residue represented by R, mention is made of aliphatic hydrocarbon residues, alicyclic hydrocarbon residues, alicyclic-aliphatic hydrocarbon residues, aromatic aliphatic hydrocarbon residues and aromatic hydrocarbon residues. As the aliphatic hydrocarbon residues, mention is made of ones having 1 to 8 carbon atoms including $C_{1-8}$ saturated aliphatic hydrocarbon residues (e.g. alkyl group) as exemplified by methyl, ethyl, propyl, isopropyl, butyl, isobutyl, sec.-butyl, t.-butyl, pentyl, isopentyl, neopentyl, t.-pentyl, hexyl, isohexyl, heptyl and octyl, and $C_{2-8}$ unsaturated aliphatic hydrocarbon residues (e.g. alkenyl group, alkynyl group) as exemplified by ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl. As the alicyclic hydrocarbon residues, mention is made of ones having 3 to 7 carbon atoms including $C_{3-7}$ saturated alicyclic hydrocarbon residues (e.g. cycloalkyl group) as exemplified by cyclopropyl, cyclobutyl, cyclopentyl, cyclohexyl and cycloheptyl, $C_{5-7}$ unsaturated alicyclic hydrocarbon residues (e.g. cycloalkenyl group, cycloalkadienyl group) as exemplified by 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. As the alicyclic-aliphatic hydrocarbon residues, mention is made of, among those formed by combination of the above-mentioned alicyclic hydrocarbon residues with aliphatic hydrocarbon residues (e.g. cycloalkyl-alkyl group, cycloalkenyl-alkyl group, cycloalkynyl-alkyl group), ones having 4 to 9 carbon atoms as exemplified by cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl. As the aromatic aliphatic hydrocarbon residues, mention is made of $C_{7-9}$ phenylalkyl as exemplified by benzyl, phenethyl, 1-phenylethyl, 3-phenylpropyl, 2-phenylpropyl and 1-phenylpropyl, and $C_{11-13}$ naphthylalkyl as exemplified by α-naphthylmethyl, α-naphthylethyl, β-naphthylmethyl and β-naphthylethyl. As the aromatic hydrocarbon residues, mention is made of, ones having 6 to 14 carbon atoms as exemplified by phenyl, naphthyl (α-naphtyl, β-naphthyl).

In the above-mentioned formula (I), as the heterocyclic group in the optionally substituted heterocyclic group represented by R, mention is made of, for example, 5- to 7-membered heterocyclic groups containing one sulfur atom, nitrogen atom or oxygen atom, 5- to 6-membered heterocyclic groups containing 2 to 4 nitrogen atoms, and 5- to 6-membered heterocyclic groups containing 1 to 2 nitrogen atoms and one sulfur atom or oxygen atom. These heterocyclic groups are optionally condensed with 6-membered ring containing one or two nitrogen atoms, benzene ring or 5-membered ring containing one sulfur atom. Examples of these heterocyclic groups include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-oxadiazol-5-yl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl and 1H-imidazo[4,5-b]pyrazin-2-yl. Among them, oxazolyl, thiazolyl and triazolyl are preferable.

In the above-mentioned formula (I), R is preferably an optionally substituted heterocyclic group, more preferably an optionally substituted oxazolyl group.

In the above-mentioned formula (I), the hydrocarbon residue and heterocyclic group represented by R may optionally have 1 to 3 substituents at substitutable positions. Examples of such substituents include aliphatic chain hydrocarbon group, alicyclic hydrocarbon group, aryl group, aromatic heterocyclic group, non-aromatic heterocyclic group, halogen atom, nitro group, optionally substituted amino group, optionally substituted acyl group, optionally substituted hydroxyl group, optionally substituted thiol group and optionally esterified carboxyl group. Examples of these aliphatic chain hydrocarbon groups include $C_{1-15}$ straight-chain or branched aliphatic hydrocarbon groups as exemplified by alkyl group, preferably $C_{1-10}$ alkyl group, alkenyl group, preferably $C_{2-10}$ alkenyl group, and alkynyl group, preferably $C_{2-10}$ alkynyl group.

Preferable examples of the alkyl group include methyl, ethyl, propyl, isopropyl, butyl, isobutyl, sec.-butyl, t.-butyl, pentyl, isopentyl, neopentyl, t.-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Preferable examples of the alkenyl group include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Preferable examples of the alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. As the alicyclic hydrocarbon group, mention is made of $C_{3-12}$ saturated or unsaturated alicyclic hydrocarbon groups as exemplified by cycloalkyl group, cycloalkenyl group and cycloalkadienyl group. Preferable examples of cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl. Preferable examples of cycloalkenyl group include 2-cyclopenten-1-yl, 3-cyclopenten-1-yl, 2-cyclohexen-1-yl and 3-cyclohexen-1-yl. Preferable examples of cycloalkadienyl group include 2,4-cyclopentadien-1-yl, 2,4-cyclohexadien-1-yl and 2,5-cyclohexadien-1-yl. The said aryl group means monocyclic or condensed polycyclic aromatic hydrocarbon group. Preferable examples of the aryl group include $C_{6-14}$ ones such as phenyl, naphthyl, anthryl, phenanthryl and acenaphthylenyl. Among them, phenyl, 1-naphthyl and 2-naphthyl are preferable.

Preferable examples of the aromatic heterocyclic group include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl; and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

Preferable examples of the non-aromatic heterocyclic group include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, pyrrolidino, piperidino and morpholino. Examples of the halogen include fluorine, chlorine, bromine and iodine. Among them, fluorine and chlorine are especially preferable. As the optionally substituted amino group, mention is made of, besides unsubstituted amino group, amino group (—$NH_2$) on which one or two of $C_{1-10}$ alkyl, $C_{1-10}$ alkenyl, $C_{1-10}$ acyl or aromatic group are substituted, [e.g. methylamino, dimethylamino, ethylamino, diethylamino, dibutylamino, diallylamino, cyclohexylamino, acetylamino, propionylamino, benzoylamino, phenylamino and N-methyl-N-phenyl-amino). The optionally substituted acyl group includes unsubstituted acyl group and substituted acyl groups. As the unsubstituted acyl group, mention is made of formyl and those formed by condensation of $C_{1-10}$ alkyl, $C_{1-10}$ alkenyl or $C_{6-12}$ aromatic group with carbonyl group, (e.g. acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl and nicotinoyl). As the substituted acyl group, mention is made of those formed by allowing, for example, $C_{1-3}$ alkyl, $C_{1-3}$ alkoxy, halogen (e.g. chlorine, fluorine, bromine, etc.), nitro, hydroxy or amino to be substituted on the said unsubstituted acyl.

The optionally substituted hydroxyl group includes unsubstituted hydroxyl group and substituted hydroxyl groups, i.e. hydroxyl groups having a suitable substituent. As the substituted hydroxyl group, mention is made of such ones as protected with hydroxyl-protecting group, for example, aryloxy, besides alkoxy, alkenyloxy, aralkyloxy and acyloxy. Preferable examples of the alkoxy include $C_{1-10}$ alkoxy (e.g. methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy, cyclobutoxy, cyclopentyloxy and cyclohexyloxy). As alkenyloxy, mention is made of $C_{2-10}$ ones such as allyloxy, crotyloxy, 2-pentenyloxy, 3-hexenyloxy, 2-cyclopentenylmethoxy and 2-cyclohexenylmethoxy, and, as aralkyloxy, mention is made of, for example, phenyl-$C_{1-4}$alkyloxy (e.g. benzyloxy and phenethyloxy). Preferable examples of acyloxy include $C_{2-4}$ alkanoyloxy (e.g. acetyloxy, propionyloxy, butyryloxy and isobutyryloxy). As aryloxy, mention is made of $C_{6-14}$ ones such as phenoxy and 4-chlorophenoxy.

As the optionally substituted thiol group, mention is made of, besides thiol group, such ones as having on this thiol group, a suitable substituent, especially the one employable as a thiol-protecting group. Practical examples of them include alkylthio, aralkylthio and acylthio. Preferable examples of the alkylthio include $C_{1-10}$ alkylthio (e.g. methylthio, ethylthio, propylthio, isopropylthio, butylthio, isobutylthio, sec.-butylthio, t.-butylthio, pentylthio, isopentylthio, neopentylthio, hexylthio, heptylthio, nonylthio, cyclobutylthio, cyclopentylthio and cyclohexylthio). As aralkylthio, mention is made of, for example, phenyl-$C_{1-4}$alkylthio (e.g. benzylthio and phenethylthio). Preferable examples of acylthio include $C_{2-4}$ alkanoylthio (e.g. acetylthio, propionylthio, butyrylthio and isobutyrylthio).

As the optionally esterified carboxyl group, mention is made of, for example, besides unsubstituted carboxyl group, alkoxycarbonyl (e.g. $C_{2-5}$ ones such as methoxycarbonyl, ethoxycarbonyl, propoxycarbonyl and butoxycarbonyl), aralkyloxycarbonyl (e.g. $C_{8-10}$ ones such as benzyloxycarbonyl), aryloxycarbonyl (e.g. $C_{7-15}$ ones such as phenoxycarbonyl and p-tolyloxycarbonyl).

Among the substituents on the hydrocarbon residue and heterocyclic group represented by R, phenyl, naphthyl, furyl, thienyl and $C_{1-3}$ alkyl are especially preferable.

In the above-mentioned formula (I), substituents on the hydrocarbon residue and heterocyclic group which are represented by R, may, when they are alicyclic hydrocarbon group, aryl group, aromatic heterocyclic group or non-aromatic heterocyclic group, have one or more, preferably 1 to 3, of suitable substituents respectively. Examples of these substituents include lower alkyl groups ($C_{1-6}$ ones), lower alkenyl groups ($C_{2-6}$ ones), lower alkynyl groups ($C_{2-6}$ ones), cycloalkyl groups ($C_{3-7}$ ones), aryl groups (e.g. phenyl and naphthyl), aromatic heterocyclic groups (e.g.

thienyl, furyl, pyridyl, oxazolyl and thiazolyl), non-aromatic heterocyclic groups (e.g. tetrahydrofuryl, morpholino, piperidino, pyrrolidino and piperazino), aralkyl groups ($C_{7-9}$ ones), amino group, N-mono($C_{1-4}$)alkylamino groups, N,N-di($C_{1-4}$)alkylamino groups, acylamino group (e.g. acetylamino, propionylamino and benzoylamino), amidino group, $C_{2-8}$ acyl group, carbamoyl group, N-mono($C_{1-4}$) alkyl carbamoyl groups, N,N-di($C_{1-4}$)alkyl carbamoyl groups, sulfamoyl group, N-mono($C_{1-4}$)alkyl sulfamoyl groups, N,N-di($C_{1-4}$)alkyl sulfamoyl groups, carboxyl group, lower alkoxycarbonyl groups ($C_{2-8}$ ones), hydroxyl group, lower alkoxy groups ($C_{1-4}$ ones), lower alkenyloxy groups ($C_{2-5}$ ones), cycloalkyloxy groups ($C_{3-7}$ ones), aralkyloxy groups ($C_{7-9}$ ones), aryloxy groups (e.g. phenyloxy and naphthyloxy), mercapto group, lower alkylthio groups ($C_{1-4}$ ones), aralkylthio groups ($C_{7-9}$ ones), arylthio groups (e.g. phenylthio and naphthylthio), sulfo group, cyano group, azido group, nitro group, nitroso group and halogen (e.g. fluorine, chlorine, bromine and iodine).

In the formula (I), R is more preferably an oxazolyl, thiazolyl or triazolyl group which is optionally substituted by 1 to 3 substituents selected from phenyl group, naphthyl group, furyl group, thienyl group or $C_{1-3}$ alkyl group.

In the above formula (I), as the alkyl groups represented by $R^1$, mention is made of, for example, $C_{1-4}$ ones such as methyl, ethyl, propyl, isopropyl, butyl, isobutyl, sec.-butyl and t.-butyl. As $R^1$, hydrogen is preferable. The symbol m denotes 0 or 1, and 0 is preferable. The symbol n denotes 0, 1 or 2, preferably 0 or 1, and, most preferably 0.

When both m and n are 0, the carbon substituted by $R^1$ is directly bonded to R; when m is 0 and n is 1 or 2, R is directly bonded to —(CH$_2$)n—; and when m is 1 and n is 0, Y is directly bonded to the carbon substituted by $R^1$.

Y stands for —CO—, —CH(OH)— or —NR$^3$—, preferably —CH(OH)— or —N(R$^3$)—. As the alkyl group in the optionally substituted alkyl group represented by $R^3$, mention is made of, for example, $C_{1-4}$ ones such as methyl, ethyl, propyl, isopropyl, butyl, isobutyl, sec.-butyl and t.-butyl. Examples of the substituents include halogen (fluorine, chlorine, bromine and iodine), $C_{1-4}$ alkoxy groups (e.g. methoxy, ethoxy, propoxy, butoxy, isobutoxy, sec.-butoxy and t.-butoxy), hydroxyl group, nitro group and $C_{1-4}$ acyl groups (e.g. formyl, acetyl and propionyl).

The $C_{1-7}$ divalent aliphatic hydrocarbon residue represented by A may be straight-chain or branched, and saturated or unsaturated. Specific examples of them include saturated ones [e.g. —CH$_2$—, —CH(CH$_3$)—, —(CH$_2$)$_2$—, —CH (C$_2$H$_5$)—, —(CH$_2$)$_3$—, —(CH$_2$)$_4$—, —(CH$_2$)$_5$—, —(CH$_2$)$_6$— and —(CH$_2$)$_7$—] and unsaturated ones [e.g. —CH=CH—, —C(CH$_3$)=CH—, —CH=CH—CH$_2$—, —C(C$_2$H$_5$)=CH—, —CH$_2$—CH=CH—CH$_2$—, —CH$_2$—CH$_2$—CH=CH—CH$_2$—. —CH=CH—CH=CH—CH$_2$— and —CH=CH—CH=CH—CH$_2$—. Among them, $C_{1-4}$ saturated ones are preferable, —CH$_2$— or —CH$_2$CH$_2$ is more preferable, and —CH$_2$CH$_2$— is most preferable.

In the formula (I), ring E has 1 or 2 substituents at any substitutable positions. Examples of such substituents include alkyl group, optionally substituted hydroxyl group, halogen atom, optionally substituted acyl group and optionally substituted amino group. These substituents have substantially the same meaning as those described as substituents of the hydrocarbon residue and heterocyclic group represented by R.

Ring E, namely the partial formula:

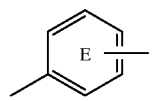

preferably represents the formula:

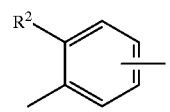

wherein $R^2$ stands for an optionally substituted hydroxyl group, a halogen atom, an optionally substituted acyl group, nitro group or an optionally substituted amino group. As the optionally substituted hydroxyl group, halogen atom, optionally substituted acyl group and optionally substituted amino group represented by $R^2$, mention is made of those described as substituents of the hydrocarbon residue and heterocyclic group represented by R. Preferable examples of $R^2$ include optionally substituted hydroxyl group or halogen atom, more preferably lower ($C_{1-4}$) alkoxy groups.

The compound wherein the partial formula:

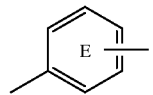

in the general formula (I) represents the formula:

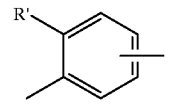

wherein R' stands for an alkyl group is not included in the compound of present invention. As the alkyl group represented by R', mention is made of those described as substituents of the hydrocarbon residue and heterocyclic group represented by R.

Preferable examples of the compounds represented by the formula (I) include those of the formula (I) in which R is oxazolyl, thiazolyl or triazolyl optionally substituted with 1 to 3 substituents selected from phenyl, naphthyl, furyl, thienyl and $C_{1-3}$ alkyl; m is 0; n is 0 or 1; $R^1$ is hydrogen; ring E, namely the partial formula:

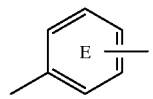

represents the formula:

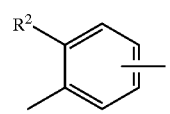

and $R^2$ is $C_{1-4}$ alkoxy group; A is —CH$_2$CH$_2$—; and L and M are both hydrogen.

Preferable specific examples of the compound represented by the formula (I) include (R)-(+)-5-[3-[4-[2-(2-furyl)-5-methyl-4-oxazolylmethoxy]-3-methoxyphenyl]propyl]-2,4-oxazolidinedione;

(S)-(−)-5-[3-[4-[2-(2-furyl)-5-methyl-4-oxazolylmethoxy]-3-methoxyphenyl]propyl]-2,4-oxazolidinedione;

5-[3-[3-fluoro-4-(5-methyl-2-phenyl-4-oxazolylmethoxy)phenyl]propyl]-2,4-oxazolidinedione;

5-[5-[3-methoxy-4-(5-methyl-2-phenyl-4-oxazolylmethoxy)phenyl]pentyl]-2,4-oxazolidinedione and 5-[3-[3,5-dimethoxy-4-[2-[(E)-styryl]-4-oxazolylmethoxy]phenyl]propyl]-2,4-oxazolidinedione.

Among these compound, (R)-(+)-5-[3-[4-[2-(2-furyl)-5-methyl-4-oxazolylmethoxy]-3-methoxyphenyl]propyl]-2,4-oxazolidinedione is especially preferable.

As salts of the compound (I) of this invention, pharmaceutically acceptable ones are preferable, as exemplified by salts formed with an inorganic base, salts formed with an organic base, salts formed with an inorganic acid, salts formed with an organic acid, and salts formed with an basic or acidic amino acid. Preferable examples of salts formed with an inorganic base include alkali metal salts such as sodium salts and potassium salts; alkaline earth metal salts such as calcium salts and magnesium salts; as well as aluminum salts and ammonium salts. Preferable examples of salts formed with an organic base include those formed with, for example, trimethylamine, triethylamine, pyridine, picoline, ethanolamine, diethanolamine, triethanolamine, dicyclohexylamine and N,N'-dibenzylethylenediamine. Preferable examples of salts formed with an inorganic acid include those formed with, for example, hydrochloric acid, hydrobromic acid, nitric acid, sulfuric acid and phosphoric acid. Preferable examples of salts formed with an organic acid include those formed with, for example, formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable examples of salts formed with a basic amino acid include those formed with, for example, arginine, lysine and ornithine, and, preferable examples of salts formed with an acidic amino acid include those formed with, for example, aspartic acid and glutamic acid. Among these salts, sodium salts and potassium salt are most preferable.

The compound (I) or its pharmaceutically acceptable salts of the present invention are less toxic and possess an action of lowering blood sugar and lipid in blood and of increasing insulin-sensitivity, which can be used as such or in combination with, for example, a per se known pharmacologically acceptable carrier, excipient and filler as a therapeutic agent of diabetes and an antihypertensive agent in mammals (e.g. humans, mice, rats, rabbits, dogs, cats, bovines, horses, swines, monkeys).

The compound (I) or its pharmaceutically acceptable salts of the present invention possess an action of inhibiting the proliferation of tumor cells, which can be used as an anticancer agent.

The compound (I) of this invention is low in toxicity. For example, oral administration of the compound of Working Example 22 at a dose of 10 mg/kg/day for 14 days to mice caused no change in body weight and liver weight in comparison with the control group, with no animals killed. And further, oral administration of the compounds of Working Example 13 and 24 respectively at a dose of 30 mg/kg/day for 4 weeks to rats caused no death.

The administration is usually performed orally in the form of, for example, tablets, capsules (including soft capsules and microcapsules), powders and granules, and, depending on cases, non-orally in the form of, for example, injections, suppositories and pellets. The dosage for adults in the case of oral administration ranges from 0.05 to 10 mg/kg/day, desirably once to three times a day.

The compound (I) of this invention, mixed with pharmaceutically acceptable carriers, can be administered orally or non-orally in the form of solid preparations such as tablets, capsules, granules and powders; or in the form a liquid preparations such as syrups and injections.

As pharmaceutically acceptable carriers, use is made of conventional organic or inorganic carriers for pharmaceutical preparations, more specifically, for example, excipients, lubricants, binders and disintegrators for solid preparations; and solvents, solubilizers, suspending agents, isotonizers, buffering agents and local anesthetic agents for liquid preparations. And, upon necessity, such additives as antiseptics, anti-oxidants, colorants and sweeteners are further used. Preferable examples of excipients include lactose, sucrose, D-mannitol, starch, crystalline cellulose and light silicon dioxide. Preferable examples of lubricants include magnesium stearate, calcium stearate, talc and colloid silica. Preferable examples of binders include crystalline cellulose, sugar, D-mannitol, dextrin, hydroxypropyl cellulose, hydroxypropyl methyl cellulose and polyvinyl pyrrolidone. Preferable examples of disintegrators include starch, carboxymethyl cellulose, carboxymethyl cellulose calcium, crosscarmellose sodium and carboxymethyl starch sodium. Preferable examples of solvents include distilled water for injection, alcohol, propylene glycol, macrogol, sesame oil and corn oil. Preferable examples of solubilizers include polyethylene glycol, propylene glycol, D-mannitol, benzyl benzoate, ethanol, tris-amino methane, cholesterol, triethanolamine, sodium carbonate and sodium citrate. Preferable examples of suspending agents include surfactants such as stearyl triethanolamine, sodium lauryl sulfate, lauryl aminopropionate, lecithin, benzalkonium chloride, benzethonium chloride, glycerin monostearate; and hydrophilic polymers such as polyvinyl alcohol, polyvinyl pyrrolidone, sodium carboxymethylcellulose, methylcellulose, hydroxymethylcellulose, hydroxyethylcellulose and hydroxypropylcellulose. Preferable examples of isotonizers include sodium chloride, glycerin and D-mannitol. Preferable examples of buffering agents include buffer solutions of phosphate, acetates, carbonates and citrates. Preferable examples of local anesthetic agents include benzyl alcohol. Preferable examples of antiseptics include paraoxybenzoic acid esters, chlorobutanol, benzyl alcohol, phenethyl alcohol, dehydroacetic acid and sorbic acid. Preferable examples of anti-oxidants include sulfites and ascorbic acid.

The following is the description on the method of producing the compound (I) of this invention.

Method A

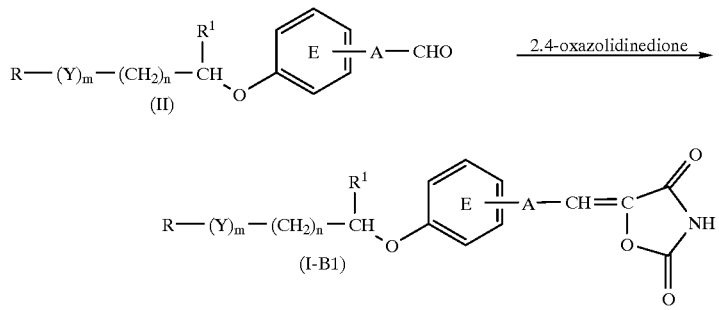

wherein each symbol has the same meaning as defined above.

The compound (I-B1) can be produced by condensation of the compound (II) with 2,4-oxazolidinedione. This reaction is conducted in a solvent in the presence of a base. As the solvent, mention is made of alcohols such as methanol, ethanol, propanol, isopropanol, and 2-methoxyethanol; aromatic hydrocarbons such as benzene, toluene and xylene; ethers such as ethyl ether, isopropyl ether, dioxane and tetrahydrofuran; N,N-dimethylformamide, dimethyl sulfoxide and acetic acid. As the base, use is made of sodium alkoxide (e.g. sodium methoxide and sodium ethoxide), potassium carbonate, sodium carbonate, sodium hydroxide, sodium acetate or a secondary amine such as piperidine, piperazine, pyrrolidine, morpholine, diethylamine and diisopropylamine. The amount of 2,4-oxazolidinedione to be used ranges from 1 to 10 molar equivalents, preferably 1 to 5 molar equivalents, relative to the compound (II). The amount of the base to be used ranges from 0.01 to 5 molar equivalents, preferably 0.05 to 2 molar equivalents, relative to the compound (II). This reaction is conducted at temperatures ranging from 0 to 150° C., preferably from 20 to 100° C., over a period ranging from 0.5 to 30 hours.

The compound (I-B1) to be produced by the above method is, in some instances, obtained as a mixture of (E)-compound and (Z)-compound, relative to the double bond at 5-position of the 2,4-oxazolidinedione.

Thus-obtained 2,4-oxazolidinedione derivative (I-B1) can be isolated and purified by a known isolating and purifying means such as concentration, concentration under reduced pressure, solvent extraction, crystallization, recrystallization, phasic transfer and chromatography.

Method B wherein Z stands for hydrogen, a lower alkyl group or an aralkyl group, and other symbols are of the same meaning as defined above.

In the above formula (III), as the lower alkyl group represented by Z, mention is made of $C_{1-4}$ alkyl (e.g. methyl, ethyl, propyl, isopropyl, butyl, isobutyl, sec.-butyl and t.-butyl). The aralkyl group represented by Z means an alkyl group having aryl group as the substituent (aryl alkyl group). Examples of the aryl group include phenyl and naphthyl, which may optionally be substituted with the aforementioned lower alkyl groups ($C_{1-4}$ ones), halogen atoms (e.g. fluorine, chlorine, bromine, iodine), hydroxyl group and nitro group. Examples of the alkyl group include $C_{1-4}$ ones as exemplified by methyl, ethyl and propyl. Preferable examples of the aralkyl group include benzyl, phenethyl, 3-phenylpropyl, (1-naphthyl)methyl and (2-naphthyl)methyl. Among them, benzyl and phenethyl are preferable.

An alkali metal salt of the compound (I-B2) can be produced by allowing a compound (III) to react with an alkali metal cyanate such as potassium cyanate or sodium cyanate. Then the alkali metal salt is processed with an acid to produce the compound (I-B2). The reaction of the compound (III) with the alkali metal cyanate is conducted in an adequate solvent. As the solvent, use is generally made of alcohols such as methanol, ethanol, propanol, isopropanol, 2-methoxyethanol and butanol; N,N-dimethylformamide (DMF), dimethyl sulfoxide, acetonitrile or a suitable mixture of them. The amount of the alkali metal cyanate to be used ranges from 1 to 10 molar equivalents, preferably 1 to 5 molar equivalents, relative to the compound (III). The reaction temperature ranges from 0 to 180° C., preferably from 30 to 150° C., and the reaction time ranges from 0.5 to 100 hours. The alkali metal salt of the compound (I-B2) thus

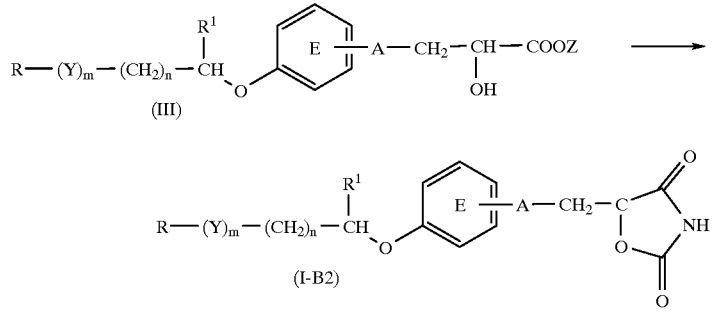

obtained is processed with an acid by a conventional means to produce the compound (I-B2). This acid treatment is conducted in the presence or absence of a suitable solvent. Examples of the solvent include alcohols such as methanol, ethanol, propanol, isopropanol, 2-methoxyethanol and butanol; aromatic hydrocarbons such as benzene, toluene and xylene; ethers such as ethyl ether, isopropyl ether, dioxane and tetrahydrofuran; halogenated hydrocarbons such as chloroform, dichloromethane and 1,1,2,2-tetrachloroethane; ethyl acetate, acetonitrile or a suitable mixture of these solvents. As the acid, use is preferably made of an excess amount of an inorganic acid such as hydrochloric acid, sulfuric acid, nitric acid and hydrobromic acid, while an organic acid such as acetic acid, citric acid or tartaric acid can also be employed.

Thus-obtained 2,4-oxazolidinedione derivative (I-B2) can be isolated and purified by a known isolating and purifying means such as concentration, concentration under reduced pressure, solvent-extraction, crystallization, recrystallization, phasic transfer and chromatography.
Method C alcohols such as methanol, ethanol, propanol, isopropanol and 2-methoxyethanol; aromatic hydrocarbons such as benzene, toluene and xylene; ethers such as ethyl ether, isopropyl ether, dioxane and tetrahydrofuran; halogenated hydrocarbons such as chloroform, dichloromethane and 1,1,2,2-tetrachloroethane; ethyl acetate, acetic acid, N,N-dimethylformamide or a suitable mixture of these solvents. Examples of preferable catalysts include metals such as nickel compounds and transition metals such as palladium, platinum and rhodium. Reaction temperatures range from 0 to 150° C., preferably from 10 to 120° C. Reaction time ranges from 0.5 to 100 hours.

The 2,4-oxazolidinedione derivative (I-B2a) thus obtained can be isolated and purified by a known isolating and purifying means such as concentration, concentration under reduced pressure, solvent extraction, crystallization, recrystallization, phasic transfer and chromatography.

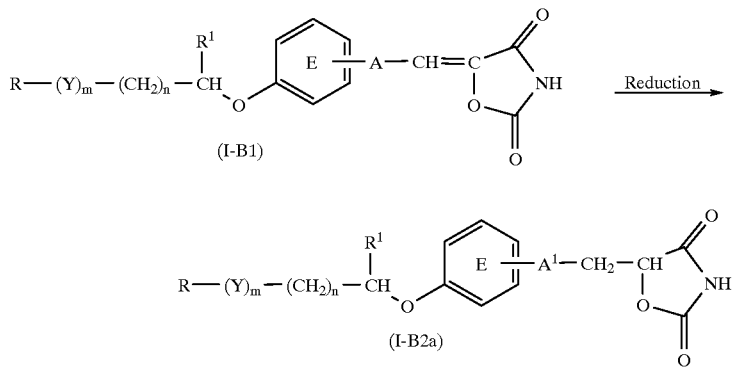

wherein $A^1$ stands for $C_{1-7}$ straight-chain or branched divalent saturated aliphatic hydrocarbon residue, and other symbols are of the same meaning as defined above.

The $C_{1-7}$ straight-chain or branched divalent saturated aliphatic hydrocarbon residue represented by $A^1$ means the saturated one among the divalent aliphatic hydrocarbon residues represented by A.

By subjecting the compound (I-B1) to reduction, the compound (I-B2a) can be produced. This reduction is conducted, in accordance with a conventional method, in a solvent in the presence of a catalyst under hydrogen atmosphere of 1 to 150 atm. As the solvent, mention is made of Method D

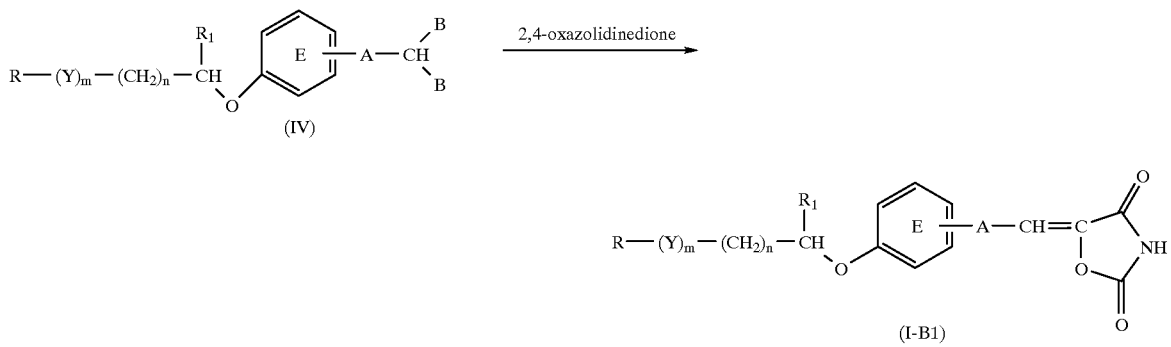

wherein B stands for lower alkoxy, lower alkylthio or lower acyloxy; and other symbols are of the same meaning as defined above.

As the lower alkoxy represented by B, mention is made, for example, $C_{1-4}$ ones such as methoxy, ethoxy, propoxy, isopropoxy and butoxy; as the lower alkylthio group, mention is made of, for example, $C_{1-4}$ ones such as methylthio, ethylthio, propylthio, isopropylthio and butylthio; and, as the lower acyloxy, mention is made of, for example, $C_{1-4}$ ones such as acetyloxy and propionyloxy. Depending on cases; two B's may be combined to each other to form, for example, ethylenedioxy, propylenedioxy or dithiotrimethylene. In other words, —CH(B)$_2$ of the formula (IV) means a protected aldehyde group.

The compound (IV) is condensed with 2,4-oxazolidinedione to produce (I-B1). This condensation reaction is conducted substantially the same manner as in the reaction of the compound (II) with 2,4-oxazolidinedione in Method A.

The compound (I-B1) to be produced by the above method is, in some instances, obtained as a mixture of (E)-compound and (Z)-compound, relative to the double bond at 5-position of the 2,4-oxazolidinedione.

The 2,4-oxazolidinedione derivative (I-B1) thus obtained can be isolated and purified by a known separating and purifying means such as concentration, concentration under reduced pressure, solvent extraction, crystallization, recrystallization, phasic transfer and chromatography.

Method E relative to the compound (V). This reaction is conducted usually at temperatures ranging from −50 to 150° C., preferable about −10 to 100° C. The reaction time ranges from 0.5 to 50 hours.

The 2,4-oxazolidinedione derivative (I-C1) thus obtained can be isolated and purified by a conventional separating and purifying means such as concentration, concentration under reduced pressure, solvent extraction, crystallization, recrystallization, phasic transfer and chromatography.

Among the compound (I-C1) produced by Method E, the compounds wherein R contains unsaturated bonds (C—C double bond, C—C triple bond) can be led to the compounds wherein the unsaturated bonds (C—C double bond, C—C triple bond) in R are reduced by substantially the same reduction reaction as in Method C.

Among the compounds produced by Method E, (I-C2) can be led to the compound (I-C3) by further subjecting the former to reduction.

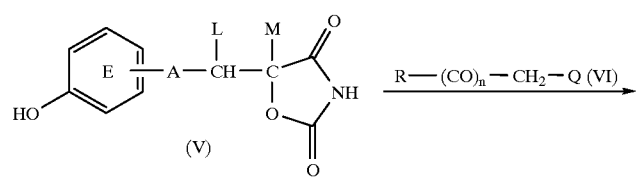

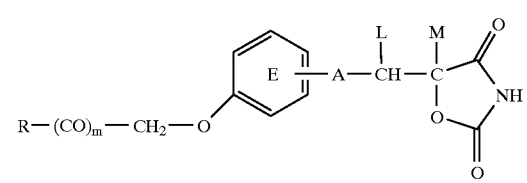

wherein Q stands for a leaving group, and other symbols are of the same meaning as defined above.

As the leaving group represented by Q, mention is made of a halogen atom (chlorine, bromine, iodine), methanesulfonyloxy, benzenesulfonyloxy and p-toluenesulfonyloxy.

The compound (V) is condensed with the compound (VI) to produced a compound (I-C1). This reaction is conducted, in accordance with a conventional method, in an adequate solvent in the presence of a base. As the solvent, mention is made of, for example, aromatic hydrocarbon such as benzene, toluene and xylene; ethers such as dioxane, tetrahydrofuran and dimethoxyethane; ketones such as acetone and 2-butanone; N,N-dimethylformamide, dimethyl sulfoxide, chloroform, dichloromethane, 1,2-dichloroethane, 1,1,2,2-tetrachloroethane and a suitable mixture of these solvents. As the base, mention is made of alkali metal salt such as sodium hydroxide, potassium hydroxide, potassium carbonate and sodium hydrogencarbonate; amines such as pyridine, triethylamine and N,N-dimethylaniline; metal hydride such as sodium hydride and potassium hydride; sodium ethoxide, sodium methoxide and potassium t.-butoxide. The amount of these bases to be used is preferably in a range of about 1 to 5 molar equivalents Method F

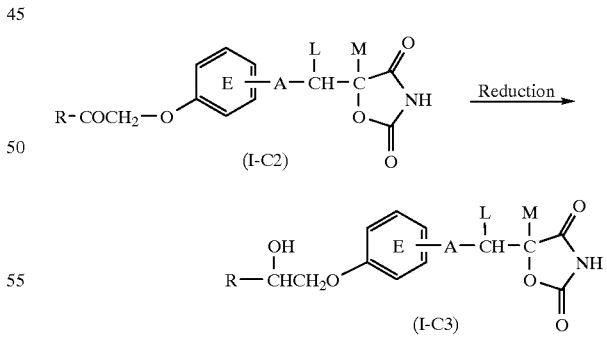

wherein each symbol is of the same meaning as defined above.

In this method, the compound (I-C2) produced by Method E is reduced to produce the compound (I-C3). This reduction reaction can be conducted by a per se known method, for example, reduction by metal hydride, reduction by a metal hydride complex compound, reduction by diborane and substituted borane and catalytic hydrogenation. In other words, this reaction is conducted by processing the compound (I-C2) with a reducing agent. As the reducing agent, mention is made of alkali metal borohydride (e.g. sodium borohydride and lithium borohydride); a metal hydride complex compound such as lithium aluminium hydride;

Method G

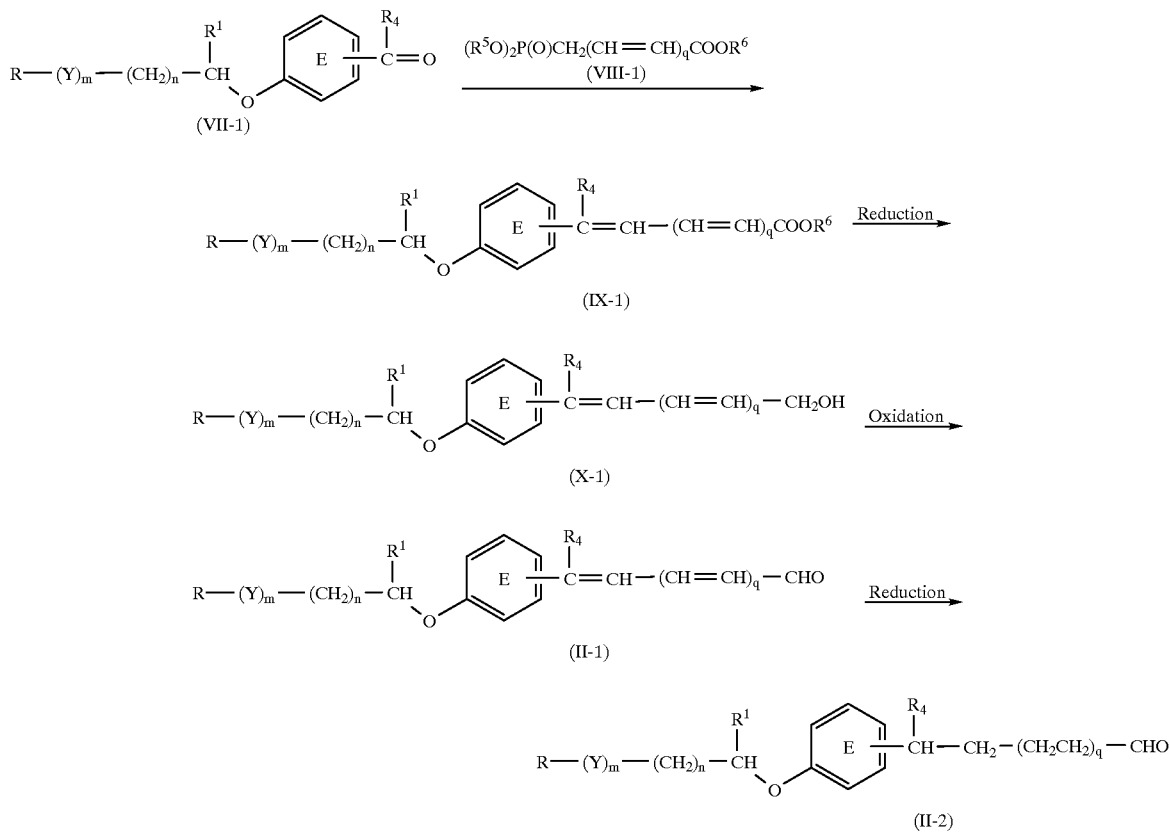

metal hydride such as sodium hydride; an organotin compound (e.g. triphneyltin hydride); metals and metal salts including nickel compounds, zinc compounds or the like; an agent for catalytic reduction using transition metal catalysts including palladium, platinum, rhodium or the like together with hydrogen; and diborane, among others. Above all, use of alkali metal borohydride (e.g. sodium borohydride, lithium borohydride) is advantageous. This reaction is conducted in an organic solvent which does not interfere with the reaction. Examples of the solvent include aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol, 2-methoxyethanol; amides such as N,N-dimethylformamide; or a suitable mixture of these solvents. From among them, a suitable one is selectively employed depending on types of reducing agents. The reaction temperature ranges from −20 to 150° C., especially from 0 to 100° C. The reaction hour ranges from about 1 to 24 hours.

The compound (I-C3) thus obtained can be isolated and purified by a conventional separating and purifying means such as concentration, concentration under reduced pressure, solvent extraction, crystallization, recrystallization, phasic transfer and chromatography.

The starting compound (II) in the Method A is produced by, for example, Method G.

wherein $R^5$ and $R^6$ independently stand for a lower alkyl group; R stands for hydrogen or a lower alkyl group; q is 0, 1 or 2; and other symbols are of the same meaning as defined above.

Examples of the lower alkyl groups represented by $R^4$, $R^5$ and $R^6$ include $C_{1-4}$ ones such as methyl, ethyl, propyl, isopropyl and butyl.

In this method, first, a carbonyl derivative (VII-1) is allowed to react with a phosphonocarboxylic acid derivative (VIII-1) to produce an unsaturated ester derivative (IX-1). The reaction of (VI-1) with (VIII-1) is conducted, in accordance with a conventional method, in an adequate solvent in the presence of a base. Examples of the solvent include aromatic hydrocarbon such as benzene, toluene and xylene; ethers such as dioxane, tetrahydrofuran and dimethoxyethane; alcohols such as methanol, ethanol and propanol; N,N-dimethylformamide, dimehtyl sulfoxide, chloroform, dichloromethane, 1,2-dichloroethane, 1,1,2,2-tetrachloroethane, as well as a suitable mixture of these solvents. Examples of the base include alkali metal salts such as sodium hydroxide, potassium hydroxide, potassium carbonate, sodium carbonate and sodium hydrogencarbonate; amines such as pyridine, triethylamine and N,N-dimethylaniline; metal hydrides such as sodium hydride and potassium hydride; sodium ethoxide, sodium methoxide and potassium t.-butoxide. The amount of these bases to be employed ranges, preferably, from about 1 to about 5 molar equivalents relative to the compound (VIII-1). The amount of the compound (VIII-1) to be used ranges from 1 to 5 molar equivalents, preferably from about 1–3 molar equivalents relative to the compound (VII-1). This reaction is conducted generally at temperatures ranging from −50 to 150° C., preferably from about −10 to 100° C. The reaction time ranges from 0.5 to 30 hours.

Then, the compound (IX-1) is subjected to reduction to produce an alcohol derivative (X-1). This reduction reaction can be conducted by a per se known method, for example, reduction with a metal hydride, reduction with a metal hydride complex compound and reduction with diborane and a substituted borane. In other words, this reaction can be conducted by processing the compound (IX-1) with a reducing agent. Examples of the reducing agents include alkali metal borohydrides (e.g. sodium borohydride and lithium borohydride); metal hydride complexes such as lithium aluminium hydride; and diborane, and use of diisobutyl aluminum hydride serves to conduct the reaction advantageously. This reaction is conducted in an organic solvent which does not interfere with the reaction. Examples of the solvent include aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; or a suitable mixture of these solvents, and, from among them, a suitable one is selectively employed depending on kinds of the reducing agent. The reaction temperature ranges from −20 to 150° C., especially preferably from 0 to 100° C., and the reaction time ranges from about 1 to 24 hours.

Then, the compound (X-1) is subjected to oxidation to produce an unsaturated aldehyde derivative (II-1). This oxidation reaction can be conducted by a per se known method, for example, oxidation with manganese dioxide, oxidation with chromic acid, oxidation with dimethyl sulfoxide, or the like. In other words, this reaction is conducted by processing the compound (X-1) with an oxidizing agent. As the oxidizing agent, use is made of manganese dioxide or chromic anhydride, and use of the former is preferable to conduct the reaction more advantageously. This reaction is conducted in an organic solvent which does not interfere with the reaction. As the solvent, use is made of, for example, aromatic hydrocarbons such as benzene, toluene and xylene; halogenated hydrocarbons such as chloroform carbon tetrachloride, dichloromethane, 1,2-dichloroethane and 1,1,2,2-tetrachloroethane; ethers such as diethyl ether, tetrahydrofuran and dioxane; dimethyl sulfoxide or a suitable mixture of these solvents, and, from among them, a suitable one is selectively employed depending on kinds of the oxidizing agent. The reaction temperatures range from −20 to 150° C., especially those ranging from 0 to 100° C. are preferable, and the reaction time ranges from about 1 to 24 hours.

Then, the compound (II-1) is subjected to reduction reaction to produce the compound (II-2). This reduction reaction is conducted in substantially the same manner as Method C.

The aldehyde derivatives (II-1), (II-2) thus obtained can be isolated and purified by means of a conventional separating and purifying process, for example, concentration, concentration under reduced pressure, solvent extraction, crystallization, recrystallization, phasic transfer, chromatography or the like.

The compound (II-3) among the compounds produced by Method G can be modified into the compound (II-4) and (II-5) having prolonged carbon chain by, for example, Method H.

Method H

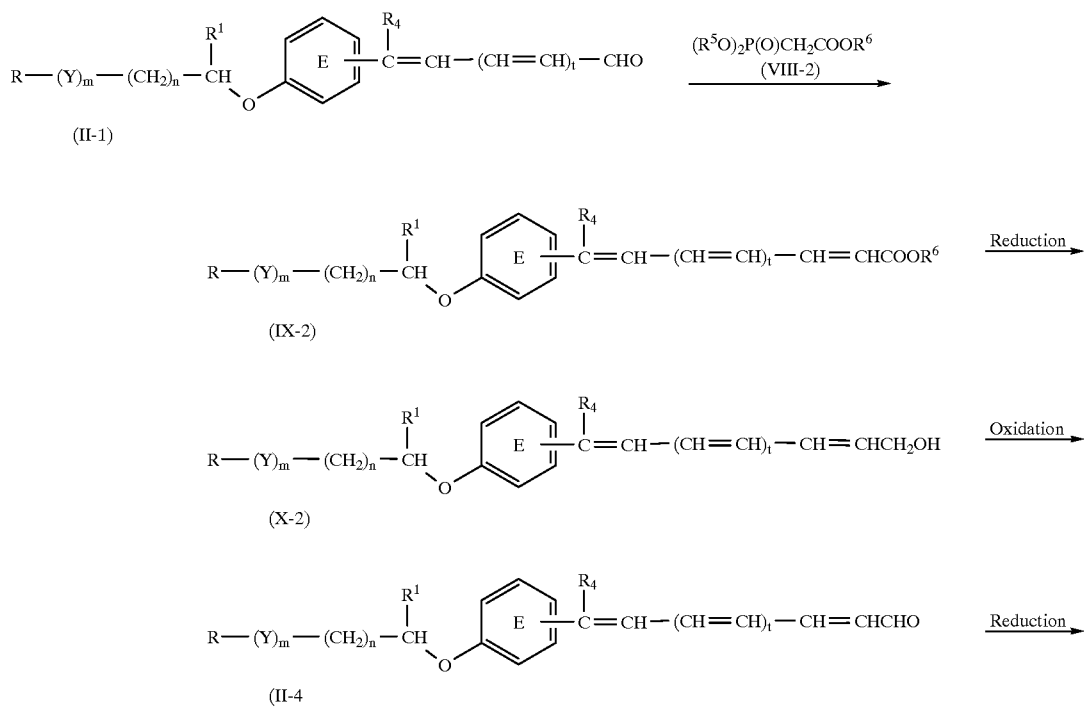

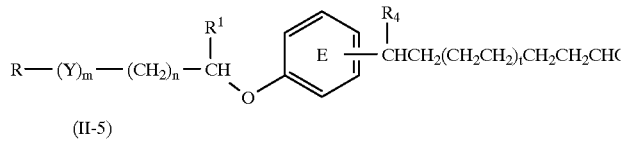

(II-5)

wherein l is 0 or 1, and other symbols are of the same meaning as defined above.

This method is conducted in substantially the same manner as in Method G. In other words, the reaction of the compound (II-3) with the compound (VIII-2) is conducted in substantially the same manner as in the reaction of the compound (VII-1) with the compound (VIII-1) in the Method G, and the reduction of the compound (IX-2) is conducted in substantially the same manner as in the reduction of the compound (IX-1) in the Method G. Further, the oxidation of the compound (X-2) is conducted in substantially the same manner as in the oxidation of the compound (X-1) in the Method G to give the compound (II-4), which is subjected to reduction in substantially the same manner as in the reduction of the compound (II-1) in Method G to produce the compound (II-5).

The aldehyde derivatives (II-4) and (II-5) thus obtained can be isolated and purified by a known separating and purifying means such as concentration, concentration under reduced pressure, solvent extraction, crystallization, recrystallization, phasic transfer and chromatography.

The compound (III) to be employed in Method B can be produced by, for example, Method I.

Method I wherein $A^2$ stands for a bond or a $C_{1-6}$ divalent aliphatic hydrocarbon residue; $A^3$ stands for a bond or a $C_{1-6}$ divalent saturated aliphatic hydrocarbon residue; and other symbols are of the same meaning as defined above.

The $C_{1-6}$ divalent aliphatic hydrocarbon residues represented by $A^2$ are $C_{1-6}$ ones among the divalent aliphatic hydrocarbon residues represented by A, and the $C_{1-6}$ divalent saturated aliphatic hydrocarbon residues represented by $A^3$ are saturated ones among those represented by $A^2$.

In this method, firstly, the compound (VII-2) is condensed with pyruvic acid to produce a compound (XI). Condensation reaction of the compound (VII-2) with pyruvic acid is conducted in substantially the same manner as in the reaction of the compound (II) with 2,4-oxazolidinedione in Method A. Then, the compound (XI) is subjected to esterification to produce a compound (XII). This esterification reaction can be conducted by a per se known method, for example, a method which comprises allowing the compound (XI) to react directly with alcohol ($R^6OH$) in the presence of an acid to cause esterification, or a method which comprises allowing a reactive derivative of the compound (XI), for example, acid anhydride, acid halide (acid chloride, acid bromide), imidazolide or a mixed acid anhydride (e.g. anhydride with methyl carbonate, anhydride with ethyl

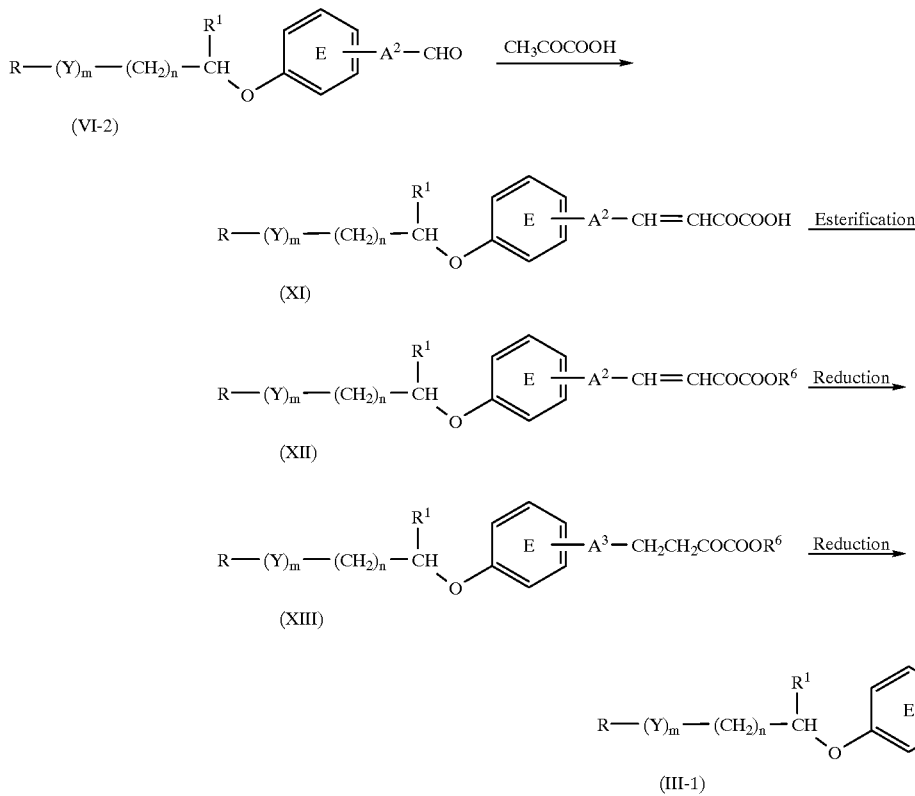

carbonate, anhydride with isobutyl carbonate or the like) to adequately react with alcohol (R⁶OH). Then, the compound (XII) is subjected to catalytic reduction to produce a compound (XIII). This catalytic reduction is conducted in substantially the same manner as in Method C. Then, the compound (XIII) is subjected to reduction to produce a compound (III-1). This reduction reaction can be conducted in substantially the same manner as in Method F.

The compound (III-1) thus obtained can be isolated and purified by a known separating and purifying means such as concentration, concentration under reduced pressure, solvent extraction, crystallization, recrystallization, phasic transfer and chromatography.

The compound (IV) to be employed in Method D can be produced by, for example, Method J.

Method J (IV-1) is subjected to reduction to produce the compound (IV-2). This reduction is conducted in substantially the same manner as that in Method C.

The compounds (IV-1) and (IV-2) thus obtained can be isolated and purified by a known separating and purifying means such as concentration, concentration under reduced pressure, solvent extraction, crystallization, recrystallization, phasic transfer and chromatography. And, the compounds (IV-1) and (IV-2) can be, by eliminating a protecting group respectively with an acid in an aqueous solvent, led to the aldehyde derivatives (II-6) and (II-7), respectively. Examples of the solvent include a mixture of water with alcohols such as methanol, ethanol and propanol, ethers such as tetrahydrofuran and dioxane, acetonitrile, acetone, 2-butanone or acetic acid. As the acid, mention is made of p-toluenesulfonic acid, besides inorganic acids such

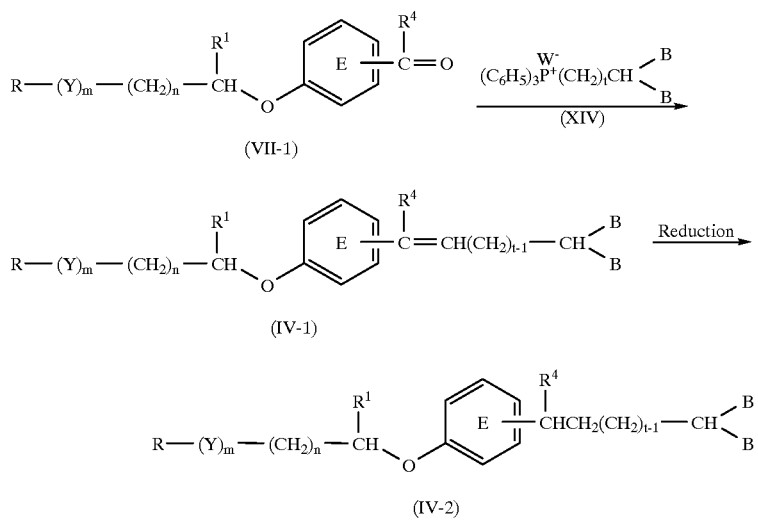

wherein W stands for halogen atom; t denotes an integer of 1 to 6; and other symbols have the same meaning as defined above.

As the halogen atom represented by W, chlorine, bromine and iodine are mentioned.

In this method, firstly, the compound (VII-1) is allowed to react with the compound (XIV) to produce the compound (IV-1). This reaction is conducted in substantially the same manner as in the reaction of the compound (VII-1) with the compound (VIII-1) in Method G. Then, the compound as hydrochloric acid, sulfuric acid, nitric acid and hydrobromic acid.

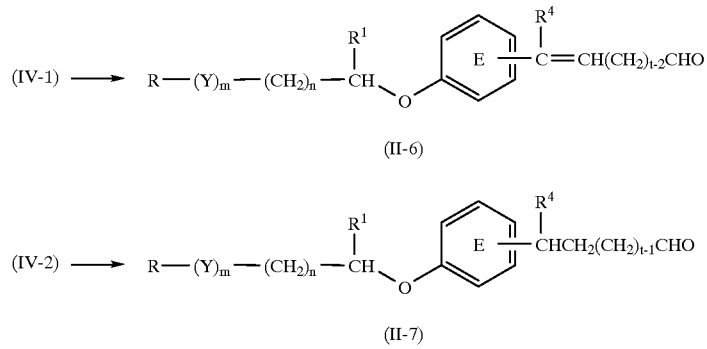

The aldehyde derivative (II) to be employed in Method A can be produced also in accordance with Method K.

Method K

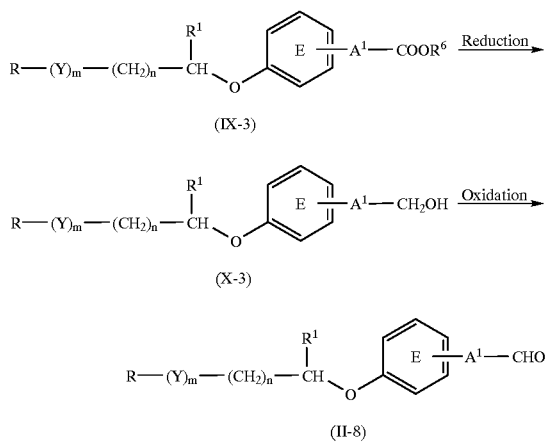

wherein each symbol is of the same meaning as defined above.

In this method, firstly, the compound (IX-3), which is produced by subjecting the compound (IX-1) or the compound (IX-2) to catalytic reduction, is subjected to reduction to produce the compound (X-3). This reduction is conducted in substantially the same manner as that of the compound (IX-1) in Method G. Then, the compound (X-3) is subjected to oxidation to produce the compound (II-8). The oxidation of the compound (X-3) to (II-8) is conducted in accordance with a per se known oxidation method, for example, the chromic acid oxidation such as Jones' oxidation using chromium oxide-sulfuric acid-pyridine, Collins' oxidation using chromium oxide-pyridine complex, oxidation using pyridinium chlorochromate (PCC) and oxidation using pyridinium dichloride (PDC); oxidation using activated DMSO or oxidation using oxoammonium salt. The oxidation using activated DMSO is preferable. Oxidation using activated dimethyl sulfoxide (DMSO) is carried out in a solvent, in the co-presence of DMSO and an electrophilic reagent. As the solvent, mention is made of ethers such as ethyl ether, isopropyl ether, tetrahydrofuran and dioxane; aromatic hydrocarbons such as benzene, toluene and xylene; N,N-dimethylformamide (DMF); halogenated hydrocarbons such as chloroform and dichloromethane; pyridine and dimethyl sulfoxide. From these solvents, a proper one is selected depending of the kind of electrophilic reagent then employed.

The compound (II-8) thus obtained can be isolated and purified by means of a conventional separating and purifying process such as concentration, concentration under reduced pressure, solvent extraction, crystallization, recrystallization, phasic transfer and chromatography. Incidentally, the compound (II-8) can be used for Method D, after subjecting the aldehyde group to acetalization or dithioacetalization by a conventional method.

A part of the intermediate (IX-1) in Method G or of the starting compound (IX-3) in Method K can be produced also by, for example, Method L.

Method L

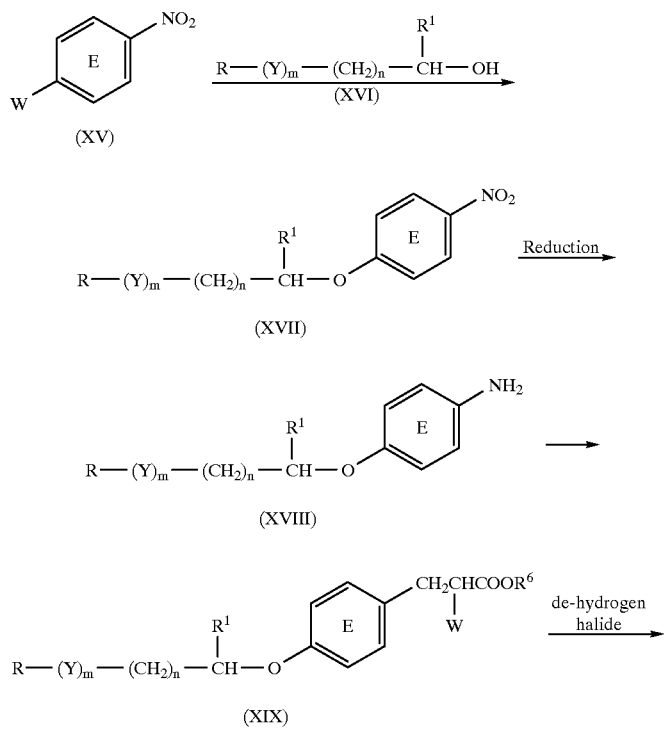

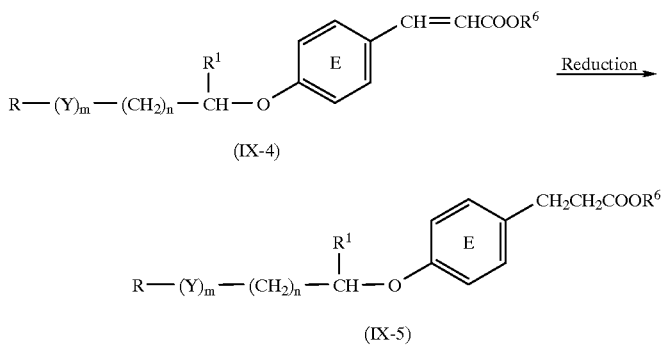

(IX-4)

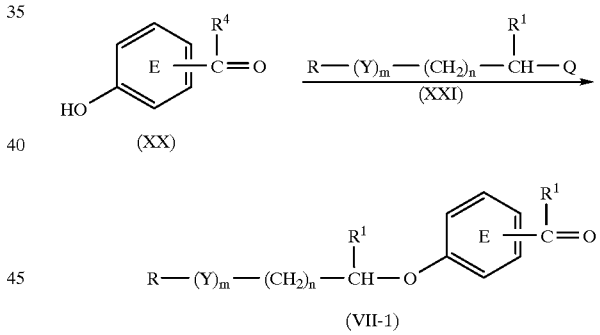

(IX-5)

wherein each symbol is of the same meaning as defined above.

In this method, firstly, the compound (XV) is allowed to react with the compound (XVI) to produce the compound (XVII). This reaction is conducted substantially the same manner as in Method E. Then, the compound (XVII) is subjected to reduction to produce the compound (XVIII). This reduction can be carried out by a per se known method, but it is conducted more advantageously in accordance with Method C.

Then, the compound (XVIII) is subjected to a per se known Meerwein Arylation reaction to produce (XIX). In this reaction, firstly, the compound (XVIII) is diazotized by adding dropwise thereto an aqueous solution of sodium nitrite ($NaNO_2$) in a solvent in the presence of a hydrohalogenic acid (e.g. HCl, HBr and HI), which is then allowed to react with acrylic acid ester ($CH_2=CHCOOR^6$) in the presence of a copper catalyst (e.g. cuprous oxide, cupric oxide, cuprous chloride, cupric chloride, cuprous bromide and cupric bromide) to produce the compound (XIX). As the solvent, mention is made of alcohols such as methanol, ethanol, propanol and isopropanol; ethers such as dioxane and tetrahydrofuran; acetone, 2-butanone or a suitable mixture of these solvents. The reaction temperature ranges from −50 to 100° C., preferably from −20 to 60° C. The reaction time ranges from 0.5 to 20 hours. Then, the compound (XIX) subjected to dehydrohalogenation to produce (IX-4). This reaction is conducted in a suitable solvent in the presence of a base. Examples of the solvent include aromatic hydrocarbons such as benzene, toluene and xylene; ethers such as dioxane, tetrahydrofuran and dimethoxyethane; alcohols such as methanol, ethanol and propanol; ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and a suitable mixture of these solvents. As the base, mention is made of inorganic bases including, for example, alkali metal hydroxide (e.g. sodium hydroxide and potassium hydroxide), alkaline earth metal hydroxide (e.g. magnesium hydroxide and calcium hydroxide), alkali metal carbonate (e.g. sodium carbonate and potassium carbonate), alkaline earth metal carbonate (e.g. magnesium carbonate and calcium carbonate), alkali metal hydrogencarbonate (e.g. sodium hydrogencarbonate and potassium hydrogencarbonate) and alkali metal acetate (e.g. sodium acetate and potassium acetate); and organic bases including trialkylamine (e.g. trimethylamine and triethylamine), picoline, N-methylpyrrolidine, N-methylmorpholine, 1,5-diazabicyclo(4.3.0]non-5-ene, 1,4-diazabicyclo[2.2.2]non-5-ene, and 1,8-diazabicyclo[5.4.0]-7-undecene. The amount of these bases to be used ranges preferably from about 1 to about 5 molar equivalents relative to the compound (XIX). This reaction is conducted usually at temperatures ranging from −20 to 150° C., preferably from about −10 to 100° C. The compound (IX-4) can be led to (IX-5) in accordance with Method C.

The compounds (IX-4) and (IX-5) thus obtained can be isolated and purified by known separating and purifying processes, for example, concentration, concentration under reduced pressure, solvent extraction, crystallization, recrystallization, phasic transfer, chromatography or the like.

The starting compound (VII-1) in Method G can be produced by, for example Method M.

Method M

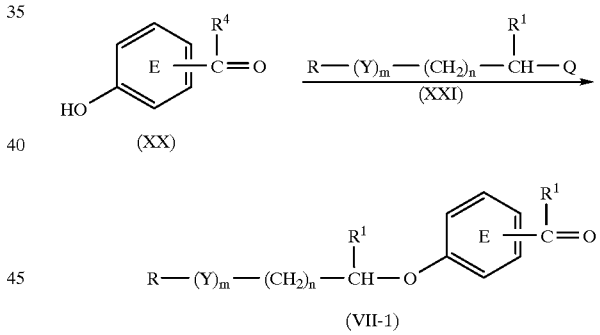

wherein each symbol is of the same meaning as defined above.

In this method, the compound (XX) is allowed to react with the compound (XXI) to produce the compound (VII-I). This reaction is conducted in substantially the same manner as in Method E.

The compound (VII-1) thus obtained can be isolated and purified by a known separating and purifying means such as concentration, concentration under reduced pressure, solvent extraction, crystallization, recrystallization, phasic transfer and chromatography.

The compound (I-B2) can be produced also by Method N described below. This method is advantageous especially for the production of an optically active compound relative to the asymmetric carbon at the 5-position of 2,4-oxazolidinedione ring.

Method N

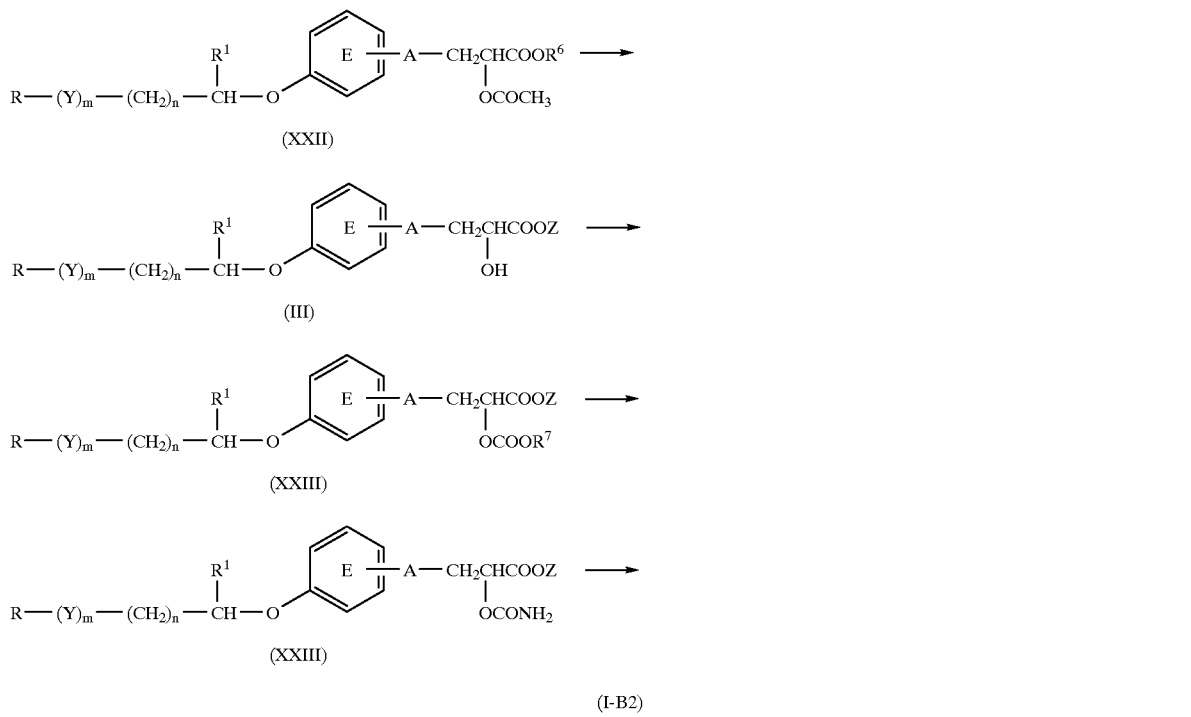

wherein $R^7$ in the formula (XXIII) stands for a lower alkyl group or a substituted phenyl group, and other symbols are of the same meaning as defined above.

The compounds represented by the above-mentioned formulae (XXII), (III), (XXIII) and (XXIV) include optically active compounds due to the asymmetric carbon at the α-position of ester residue, and the compounds represented by the formula (I-B2) include optically active compounds due to the asymmetric carbon at the 5-position of 2,4-oxazolidinedione ring.

As the lower alkyl group represented by $R^7$ in the formula (XXIII), mention is made of $C_{1-4}$ alkyl (e.g. methyl, ethyl, propyl, isopropyl, butyl and isobutyl). Examples of the substituent at the substituted phenyl group represented by $R^7$ include the above-mentioned lower alkyl groups ($C_{1-4}$ ones), halogen atoms (fluorine, chlorine, bromine and iodine), hydroxyl group and nitro group.

This method provides a method of producing 2,4-oxazolidinedione derivative (I-B2) starting from α-acetoxyester represented by the formula (XXII).

In this method, firstly, the α-hydroxycarboxylic acid ester derivative (III) is produced from the compound (XXII). This reaction is conducted, in accordance with a per se known method, in alcohol (Z—OH) in the presence of an acid. The amounts of alcohol (Z—OH) and acid to be employed are usually a large excess ones. This reaction is carried out usually at temperatures ranging from −80 to 100° C., preferably from about −50 to 30° C. The reaction time ranges from 0.5 to 100 hours. Then, the compound (III) is allowed to react with chlorocarbonic ester (ClCOOR$^7$), and the reaction mixture is further allowed to react with ammonia to produce the compound (XXIV). The reaction of the compound (III) with chlorocarbonic ester (ClCOOR$^7$) is carried out, in accordance with a conventional method, in a suitable solvent in the presence of a base. As the solvent, mention is made of, for example, aromatic hydrocarbons such as benzene, toluene and xylene; ethers such as dioxane, tetrahydrofuran and dimethoxyethane; chloroform, dichloromethane, 1,2-dichloroethane, 1,1,2,2-tetrachloroethane, and a suitable mixture of these solvents. As the base, mention is made of alkali metal salts such as sodium hydroxide, potassium hydroxide, potassium carbonate, sodium carbonate and sodium hydrogencarbonate, and amines such as pyridine, triethylamine and N,N-dimethylaniline. The amount of these bases to be employed is preferably in the range of from about 2 to 5 molar equivalents relative to the compound (III). Bases such as pyridine and triethylamine can be used also as solvents. The amount of chlorocarbonic ester (ClCOOR$^7$) to be used ranges from about 1 to 5 molar equivalents, preferably from 1 to 3 molar equivalents, relative to the compound (III). This reaction is conducted usually at temperatures ranging from −80 to 100° C., preferably from about −50 to 50° C. The reaction time ranges from 0.5 to 30 hours.

Then, the product (XXIII) is subjected to the reaction with ammonia to produce the compound (XXIV). This reaction is carried out usually in a suitable solvent in the presence of ammonia. As the solvent, mention is made of aromatic hydrocarbons such as benzene, toluene and xylene; ethers such as dioxane, tetrahydrofuran and dimethoxyethane; chloroform, dichloromethane, 1,2-dichloroethane, 1,1,2,2-tetrachloroethane, ethyl acetate; and a suitable mixture of these solvents. As ammonia, ammonia gas or aqueous ammonia is used, and the reaction is carried out at temperatures ranging from −100 to 50° C., preferably about from −80 to 30° C. The reaction time ranges from 0.5 to 30 hours. The compound (XXIV) thus obtained is subjected to cyclization to produce the 2,4-oxazolidinedione derivative (I-B2). The cyclization reaction is carried out by processing the compound (XXIV) in accordance with a conventional method, with a base in a suitable solvent. As the solvent, mention is made of, for example, aromatic hydrocarbons such as benzene, toluene and xylene; ethers such as dioxane, tetrahydrofuran and dimethoxyethane; chloroform, dichloromethane, 1,2-dichloroethane, 1,1,2,2-tetrachloroethane, acetonitrile; and a suitable mixture of these solvents. As the base, mention is made of alkali metal salts such as sodium hydroxide, potassium hydroxide, potassium carbonate, sodium carbonate and sodium hydrogencarbonate; amines such as pyridine, triethylamine, N,N-dimethylaniline, 1,8-diazabicyclo[5.4.0]undec-7-ene (DBU), 1,5-diazabicyclo[4.3.0]non-5-ene (DBN); sodium ethoxide, sodium methoxide, potassium tert.-butoxide or the like. Amount of these bases to be employed ranges from 1 to 5 molar equivalents relative to the compound (XXIV). This reaction is conducted usually at temperatures ranging from −80 to 50° C., preferably from about −50 to 30° C. The reaction time ranges from 0.5 to 30 hours.

The 2,4-oxazolidinedione derivative (I-B2) thus obtained can be isolated and purified by a conventional separating and purifying means such as concentration, concentration under reduced pressure, solvent extraction, crystallization, recrystallization, phasic transfer and chromatography.

The compounds (XXII) and (III) including optically active compounds to be employed in Method N can be produced by, for example, Method O.

Method O

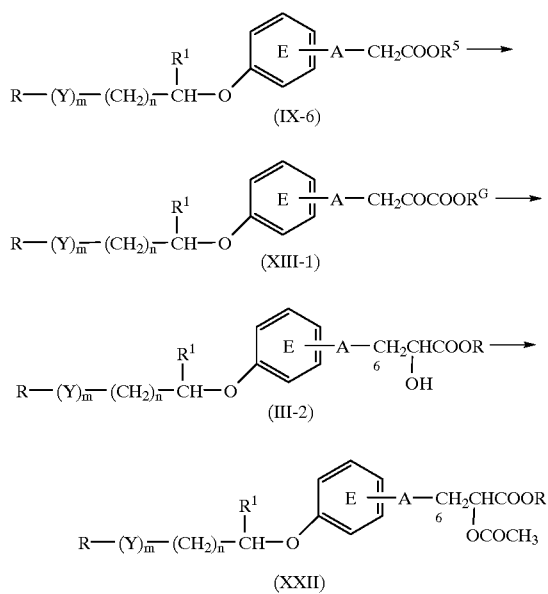

wherein each symbol is of the same meaning as defined above.

In this method, the compound (IX-6) is subjected to reaction with oxalic ester $(COOR^6)_2$ in the presence of a base. The reaction of the compound (IX-6) with oxalic ester $(COOR^6)_2$ is conducted, in accordance with a conventional method, in a suitable solvent in the presence of a base. As the solvent, mention is made of, for example, alcohols such as methanol, ethanol, propanol, isopropanol and 2-methoxyethanol; aromatic hydrocarbons such as benzene, toluene and xylene; ethers such as ethyl ether, isopropyl ether, dioxane and tetrahydrofuran; halogenated hydrocarbons such as chloroform, dichloromethane and 1,1,2,2-tetrachloroethane; N,N-dimethylformamide; and a suitable mixture of these solvents. As the base, mention is made of sodium ethoxide, sodium methoxide and potassium tert.-butoxide or the like. The amount of these bases to be employed ranges from about 1 to 5 molar equivalents relative to the compound (IX-6), and the amount of $(COOR^6)_2$ to be employed is preferably ranges from about 1 to 5 molar equivalents relative to the compound (IX-6). This reaction is conducted usually at temperatures ranging from −50 to 150° C., preferably from about −10 to 100° C. The reaction time ranges from 0.5 to 50 hours.

The condensate thus obtained is subjected to decarboxylation reaction to produce α-ketoester (XIII-1). This decarboxylation reaction is conducted under heating in aqueous dimethyl sulfoxide in the presence of sodium chloride or lithium chloride. The amount of sodium chloride or lithium chloride ranges from 1 to 5 molar equivalents. The reaction temperatures ranges from 50 to 150° C., preferably from about 80 to 120° C. The reaction time ranges from 0.5 to 50 hours. Then, the α-ketoester (XIII-1) thus obtained is subjected to reduction to product the compound (III-2). This reduction can be carried out by a per se known method, for example, reduction with a metal hydride, reduction with a metal hydride complex compound, reduction with diborane and a substituted diborane, catalytic hydrogenation or the like. In other words, this reaction is conducted by processing the compound (XIII-1) with a reducing agent. Examples of the reducing agent include alkali metal borohydrides (e.g. sodium borohydride and lithium borohydride); metal hydride complex compounds such as lithium aluminum hydride; metal hydrides such as sodium hydride; organotin compounds (e.g. triphenyltin hydride), metals such as a nickel compound or a zinc compound and salts thereof; catalytic reduction agents using a transition metal such as palladium, platinum or rhodium and hydrogen; and diborane, and, use of, among them, alkali metal borohydride (e.g. sodium borohydride or lithium borohydride) serves to allow the reaction to proceed advantageously. This reaction is conducted in an organic solvent which does not interfere with the reaction. Examples of the solvent include aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide: or a suitable mixture of these solvents, and, from among them, a suitable one is selectively employed depending on kinds of the reducing agent. The reaction temperatures ranges from −20 to 150° C., especially preferably from 0 to 100° C., and the reaction time ranges from about 1 to 24 hours.

An optically active compound of the compound (III-2) can be produced from the compound (XIII-1) in accordance with a per se known asymmetric reduction, as exemplified by asymmetric reduction of ketone to alcohol by using baker's yeast; asymmetric reduction of ketone to alcohol by using optically active-DIOP/[Rh(COD)Cl$_2$]$_2$,Ph$_2$SiH$_2$; asymmetric reduction of ketone to alcohol by asymmetric hydrogenation using chiral catalyst [(Cinchonidine, Pt—Al$_2$O$_3$), (Quinidine, Pt-Al$_2$O$_3$), (Cinchonidine, Pt—Al$_2$O$_3$), (optically active-BINAP, RuCl$_2$)etc.]. An optically active compound of the compound (XXII) can be produced by optical resolution based on theory of rate process by a per se known enzyme reaction. For example, a racemate of the compound (III-2) is allowed to react in toluene in the presence of vinyl acetate and lipase to produce an optically active compound of the compound (XXII).

Among the compounds represented by the general formula (IX-6) referred to in Method O, the compound (IX-9) can be derived from the carbonyl derivative (VII-3) in accordance with Method P.

Method P

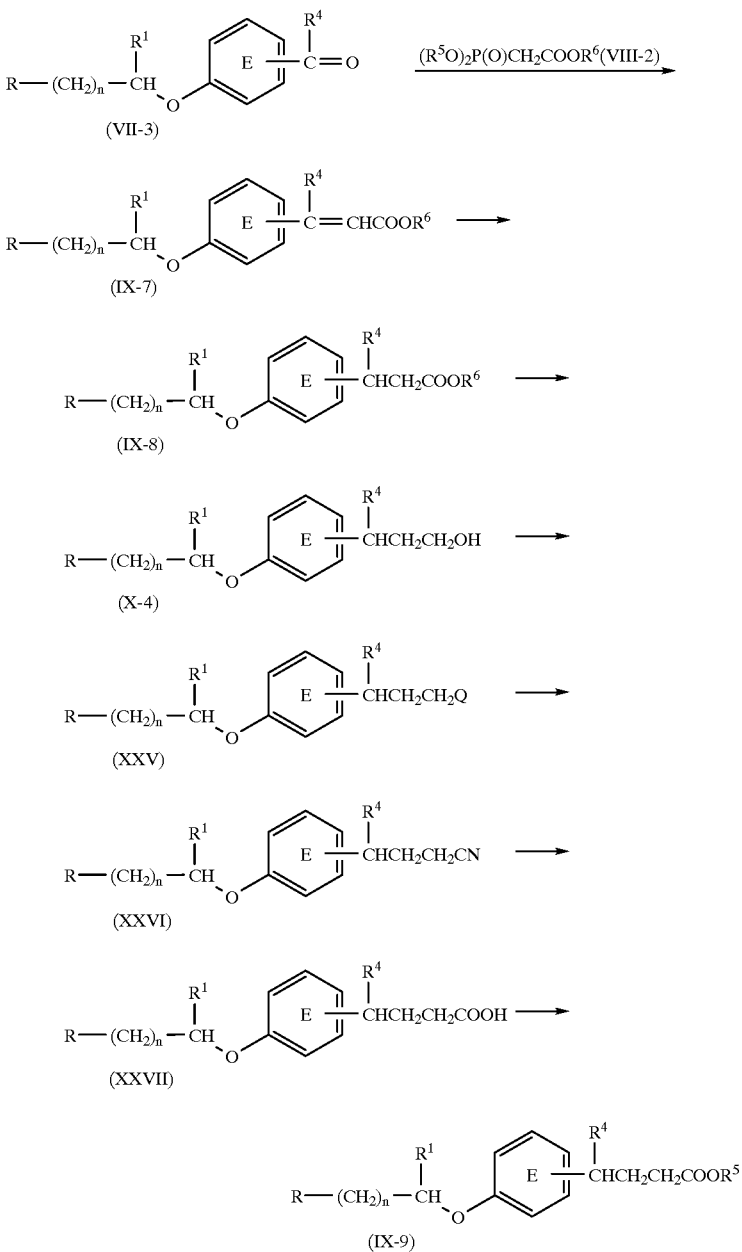

wherein each symbol is of the same meaning as defined above.

In this method, firstly, a carbonyl derivative (VII-3) is allowed to react with a phosphonoacetic acid derivative (VIII-2) to produce an unsaturated ester derivative (IX-7). The reaction of (VII-3) with (VIII-2) is conducted in substantially the same manner as in the reaction of the compound (VII-1) with the compound (VIII-1) in Method G. Then, the compound (IX-7) is processed in substantially the same manner as in the catalytic reduction of the compound (II-1) in Method G to produce the compound (IX-8). Further, the compound (IX-8) is processed in substantially the same manner as in the reduction of the compound (IX-1) in Method G to produce an alcohol derivative (X-4). The alcohol derivative (X-4) is subjected to a per se known reaction, for example, chlorination with thionyl chloride, bromination with phosphorus tribromide or mesylation with methanesulfonyl chloride to produce compounds of the formula (XXV) in which Q is Cl, Br and $OSO_2CH_3$, respectively. The compound (XXV) is led to a compound represented by the formula (XXVI) by allowing to react with potassium cyanide or sodium cyanide in a suitable solvent. Examples of the solvent include aromatic hydrocarbons such as benzene, toluene and xylene; ethers such as dioxane, tetrahydrofuran and dimethoxyethane; alcohols such as methanol, ethanol and propanol; N,N-dimehtylformamide, dimethyl sulfoxide, chloroform, dichloromethane, 1,2-dichloroethane, 1,1,2,2-tetrachloroethane, acetone, 2-butanone and a suitable mixture of these solvents. The amount of potassium cyanide or sodium cyanide is preferably in the range from 1 to 5 molar equivalents relative to the compound (XXV). This reaction is conducted usually at temperatures ranging from 0 to 150° C., preferably from about 20 to 100° C. The reaction time ranges from 0.5 to 30 hours. Then, the compound (XXVI) is subjected to hydrolysis to produce a carboxylic acid derivative (XXVII). This hydrolysis is conducted preferably in an aqueous solvent in the presence of potassium hydroxide or sodium hydroxide. The carboxylic acid derivative (XXVII) is processed in substantially the same manner as in the esterification of the compound (XI) in Method I to produce the compound (IX-9).

The ester derivative (IX-9) can be isolated and purified by a known separating and purifying means such as concentration, concentration under reduced pressure, solvent extraction, crystallization, recrystallization, phasic transfer, chromatography or the like.

The starting compound (II) in Method A, the starting compound (IV) in Method D, the starting compound (VII-1) in Method G and Method J, the starting compound (VII-2) and the compound (XIII) in Method I, the starting compound (IX-3) in Method K, the starting compound (IX-6) in Method O, the starting compound (VII-3) in Method P, and the like can be produced also by Method Q.

Method Q

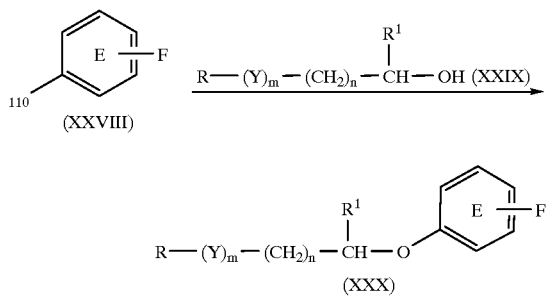

wherein F stands for —A—CHO, —A—CH(B)$_2$, —C(R$^4$)=O, —A$^2$—CHO, —A$^3$—CH$_2$CH$_2$COOR$^6$, —A$^1$—COOR$^6$ or —A—CH$_2$COOR$^5$, and other symbols are of the same meaning as defined above.

In this method, the compound (XXVIII) is allowed to react with the compound (XXIX) to produce the compound (XXX). This method is carried out in accordance with a per se known Mitsunobu reaction.

This reaction is carried out preferably in a solvent in the presence of triphenylphosphine and diethylazedicarboxylate. Examples of the solvent include aromatic hydrocarbons such as benzene, toluene and xylene; ethers such as ethylether, isopropylether, dioxane and tetrahydrofuran; halogenated hydrocarbons such chloroform, dichloromethane and 1,1,2,2-tetrachloroethane; and a suitable mixture of these solvents. The amount of triphenylphosphine and diethylazedicarboxylate is preferably in the range from 1 to 5 molar equivalents relative to the compound (XXVIII) respectively, and the amount of the compound (XXIX) is preferably in the range from 1 to 2 molar equivalents relative to the compound (XXVIII). This reaction is conducted usually at temperatures ranging from −50 to 100° C., preferably from about −30 to 800° C. The reaction time ranges from 0.5 to 50 hours.

The compound (XXX) thus obtained can be isolated and purified by a known separating and purifying means such as concentration, concentration under reduced pressure, solvent extraction, crystallization, recrystallization, phasic transfer, chromatography or the like.

The starting compound (V) in Method E can be produced by, for example Method R, Method S and Method T described below.

Method R

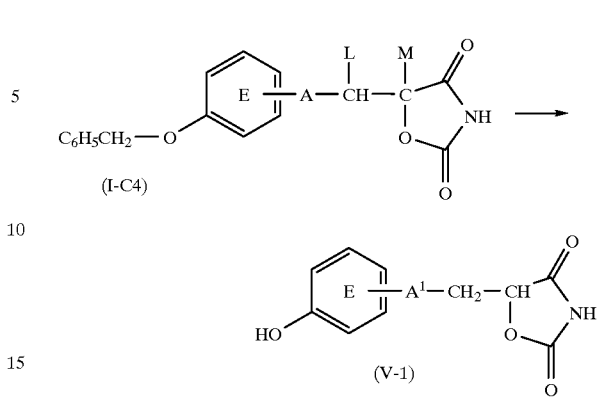

wherein each symbol is of the same meaning as defined above.

In this method, the benzyl compound (I-C4) produced in accordance with Method A, Method B, Method D or Method N is subjected to a reaction for elimination of benzyl group to produce the compound (V-1). This method is carried out in substantially the same manner as in Method C.

The compound (V-1) thus obtained can be isolated and purified by a known separating and purifying means such as concentration, concentration under reduced pressure, solvent extraction, crystallization, recrystallization, phasic transfer, chromatography or the like.

Method S

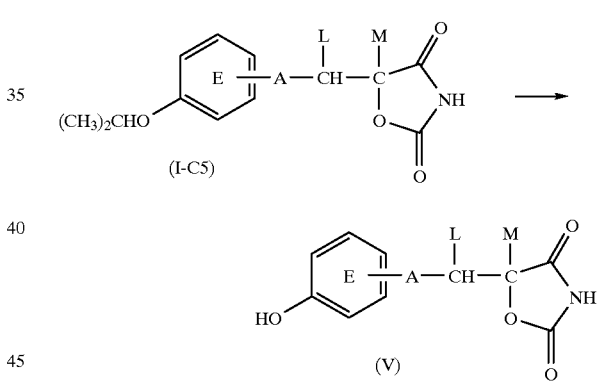

wherein each symbol is of the same meaning as defined above.

In this method, the isopropyl compound (I-C5) produced in accordance with Method A, Method B, Method C, Method D or Method N is subjected to a reaction for elimination of isopropyl group to produce the compound (V).

This reaction is carried out by processing in a solvent with titanium tetrachloride, titanium trichloride, boron trichloride, silicon tetrachloride or the like. Examples of the solvent include halogenated hydrocarbons such as carbon tetrachloride, chloroform, dichloromethane, 1,1,2,2-tetrachloroethane; acetonitrile and a suitable mixture of these solvents. The amount of titanium tetrachloride, titanium trichloride, boron trichloride, silicon tetrachloride or the like is preferably in the range from 1 to 6 molar equivalents relative to one isopropoxy group in the compound (I-C5). This reaction is conducted usually at temperatures ranging from −80 to 100° C., preferably from about −50 to 80° C. The reaction time ranges from 0.5 to 50 hours.

The reaction is carried out in substantially the same manner as in Method C.

The compound (V) thus obtained can be isolated and purified by a known separating and purifying means such as concentration, concentration under reduced pressure, solvent extraction, crystallization, recrystallization, phasic transfer, chromatography or the like.

Method T

In this method, the compound produced in accordance with Method A, Method B, Method C, Method D, Method E, Method F or Method N and having methoxy group as a substituent in ring E, is subjected to a reaction for elimination of methyl group to produce the phenol derivative. This reaction is carried out in a solvent by a reaction with alkyl mercaptans such as ethyl mercaptan and dodeca mercaptan in the presence of aluminum chloride. Examples of the solvent include aromatic hydrocarbons such as benzene, toluene and xylene; ethers such as ethylether, isopropyl ether, dioxane and tetrahydrofuran; halogenated hydrocarbons such as chloroform, dichloromethane and 1,1,2,2-tetrachloroethane; and a suitable mixture of these solvents. The amount of aluminum chloride is preferably in the range from 5 to 20 molar equivalents relative to the methoxy derivative, and the amount of titanium tetrachloride is preferably in the range from 5 to 20 molar equivalents relative to the methoxy derivative. This reaction is conducted usually at temperatures ranging from −80 to 100° C., preferably from about −50 to 50° C. The reaction time ranges from 0.5 to 50 hours.

The phenol derivative thus obtained can be isolated and purified by a known separating and purifying means such as concentration, concentration under reduced pressure, solvent extraction, crystallization, recrystallization, phasic transfer, chromatography or the like.

The compound (I) of this invention or salts thereof possess excellent hypoglycemic and hypolipidemic activities. Experimental data supporting these activities are as follows.

EXPERIMENTAL EXAMPLE

Hypoglycemic and hypolipidemic actions in mice

A test compound mixed in a powdery feed (CE-2, Clea Japan Inc.) at a rate of 0.005% was fed to $KKA_y$ mice (9–14 week old) freely for 4 days. During the period, the animals were allowed to access freely to water. Blood was collected from the orbital venous plexus. Using the plasma, glucose and triglyceride were enzymatically determined quantitatively by using Iatrochem-GLU (A) and Iatro-MA701 TG kit (Iatron Laboratories Inc.). The respective values are percents reduction (%) found in drug-dosed groups from the control group not receiving the test compound, which are shown in Table 1.

TABLE 1

| Compound (W. Ex. No.) | Hypoglycemic Action (%) | Triglyceride-lowering Action (%) |
|---|---|---|
| 5 | 48 | 72 |
| 15 | 51 | 47 |
| 17 | 61 | 75 |
| 22 | 57 | 56 |

As shown above, oxazolidinedione derivatives (I) of the present invention exhibit excellent hypoglycemic and hypolipidemic actions in model mice suffering from noninsulin-dependent diabetes mellitus, and are pharmaceutically useful as therapeutic agents for diabetes, hyperlipemia and hypertension, among others.

The following working examples, formulation examples and reference examples are merely intended to illustrate the present invention in further detail but should by no means be construed as defining the scope of the invention.

WORKING EXAMPLE 1

A mixture of 3-methoxy-4-(2-phenyl-4-oxazolylmethoxy)cinnamaldehyde (5.5 g), 2,4-oxazolidinedione (6.7 g), piperidine (1.4 g) and acetic acid (120 ml) was stirred for three days under reflux. The reaction mixture was cooled, and resulting crystalline precipitate was collected by filtration, which was washed with water, ethanol and isopropyl ether, successively to give 5-[3-methoxy-4-(2-phenyl-4-oxazolylmethoxy)cinnamylidene]-2,4-oxazolidinedione (2.9 g, 43%), which was recrystallized from chloroform-methanol to afford yellow needles, m.p.227–228° C.

WORKING EXAMPLES 2 TO 4

In substantially the same manner as in Working Example 1, compounds set forth in Table 2 were produced.

TABLE 2

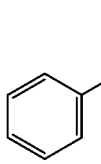

| No. of W. Ex. | A | C | m.p. (° C.) | Recrystallization solvent |
|---|---|---|---|---|
| 2 | 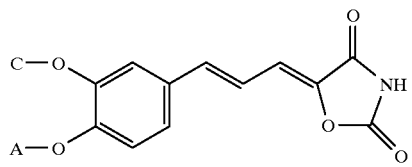 | $CH_3$— | 211–212 | chloroform-methanol |
| 3 | $(CH_3)_2CH$— | $CH_3$— | 226–227 | ethyl acetate- |

TABLE 2-continued

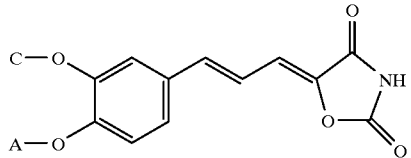

| No. of W. Ex. | A | C | m.p. (° C.) | Recrystallization solvent |
|---|---|---|---|---|
| | | | | hexane |
| 4 | (2-phenyl-4-oxazolyl)-CH₂— | CH₃CH₂— | 240–242 | dichloromethane-methanol |

WORKING EXAMPLE 5

A mixture of 5-[3-methoxy-4-(2-phenyl-4-oxazolylmethoxy)cinnamylidene]-2,4-oxazolidinedione (1.0 g), platinum oxide (PtO₂) (0.2 g) and tetrahydrofuran (THF)-acetic acid (4:1, 190 ml) was subjected to catalytic hydrogenation under 1 atmospheric pressure at room temperature. The catalyst was filtered off, and the filtrate was concentrated under reduced pressure. The concentrate was dissolved in chloroform, which was washed with water, a saturated aqueous solution of sodium hydrogencarbonate and water, successively, followed by drying (MgSO₄). The chloroform layer was concentrated under reduced pressure, and the concentrate was subjected column chromatography on silica gel. From the fraction eluted with chloroform-ethyl acetate (4:1), 5-[3-[3-methoxy-4-(2-phenyl-4-oxazolylmethoxy)phenyl]propyl]-2,4-oxazolidinedione (0.19 g, 19%) was obtained. Recrystallization of the product from ethyl acetate-hexane gave colorless prisms, m.p.134–135° C.

WORKING EXAMPLE 6

A mixture of 5-[3-methoxy-4-(2-phenyl-4-thiazolylmethoxy)cinnamylidene]-2,4-oxazolidinedione (0.76 g), palladium-carbon (5%, 1.0 g) and tetrahydrofuran (THF) (100 ml) was subjected to catalytic hydrogenation under 1 atmospheric pressure at room temperature. The catalyst was filtered off, and the filtrate was concentrated under reduced pressure. The concentrate was subjected to column chromatography on silica gel. From the fraction eluted with chloroform-ethyl acetate (4:1), 5-[3-[3-methoxy-4-(2-phenyl-4-thiazolylmethoxy)phenyl]propyl]-2,4-oxazolidinedione (0.25 g, 32%) was obtained. Recrystallization of the product from ethyl acetate-hexane gave colorless prisms, m.p.96–97° C.

WORKING EXAMPLE 7

In substantially the same manner as in Working Example 6, 5-[3-ethoxy-4-(5-methyl-2-phenyl-4-oxazolylmethoxy)cinnamylidene]-2,4-oxazolidinedione was subjected to catalytic hydrogenation to yield 5-[3-[3-ethoxy-4-(5-methyl-2-phenyl-4-oxazolylmethoxy)phenyl]propyl]-2,4-oxazolidinedione. The product was recrystallized from dichloromethane-ether to give colorless prisms, m.p.129–130° C.

WORKING EXAMPLE 8

A mixture of 5-(4-isopropoxy-3-methoxycinnamylidene)-2,4-oxazolidinedione (7.1 g), palladium-carbon (5%, 7.1 g) and tetrahydrofuran (THF) (150 ml) was subjected to catalytic hydrogenation under 1 atmospheric pressure at room temperature. The catalyst was filtered off, and the filtrate was concentrated under reduced pressure. The concentrate was subjected to column chromatography on silica gel. From the fraction eluted with chloroform-ethyl acetate (4:1), 5-[3-(4-isopropoxy-3-methoxyphenyl)propyl]-2,4-oxazolidinedione (4.3 g, 60%) was obtained as an oily product.

NMR (δ ppm in CDCl₃): 1.35(6H,d,J=6 Hz), 1.79–2.05 (4H,m), 2.62(2H,t,J=7 Hz), 3.84(3H,s), 4.47(1H,m), 4.84 (1H,dd,J=7&5 Hz), 6.67(1H,dd,J=8&2 Hz), 6.69(1H,s), 6.82(1H,d,J=8 Hz), 8.33(1H,s).

WORKING EXAMPLE 9

Sodium hydride (60% in oil, 0.32 g) was added, at 0° C., to a solution of 5-[3-(4-hydroxy-3-methoxyphenyl)propyl]-2,4-oxazolidinedione (1.0 g) in N,N-dimethylformamide (DMF) (20 ml). The mixture was stirred for one hour at room temperature. To the reaction mixture was then added 4-chloromethyl-2-[(E)-styryl]oxazole (0.87 g), which was stirred for 3.5 hours at 90° C. The reaction mixture was poured into water, which was acidified with 2N HCl, followed by extraction with ethyl acetate. The ethyl acetate layer was washed with water, dried (MgSO₄) and concentrated under reduced pressure to yield 5-[3-[3-methoxy-4-[2-[(E)-styryl]-4-oxazolylmethoxy]phenyl]propyl]-2,4-oxazolidinedione (1.1 g, 66%). The product was recrystallized from ethyl acetate-hexane to give colorless prisms, m.p.178–179° C.

WORKING EXAMPLE 10

In substantially the same manner as in Working Example 9, 5-[3-(4-hydroxy-3-methoxyphenyl)propyl]-2,4-oxazolidinedione was allowed to react with 4-chloromethyl-2-[(E)-styryl]thiazole to yield 5-[3-[3-methoxy-4-[2-[(E)-styryl]-4-thiazolylmethoxy]-phenyl]propyl]-2,4-oxazolidinedione. The product was recrystallized from chloroform-methanol to give colorless prisms, m.p.202–203° C.

WORKING EXAMPLE 11

A mixture of 3-ethoxy-4-(2-phenyl-4-oxazolylmethoxy)cinnamaldehyde (3.0 g), 2,4-oxazolidinedione (1.7 g), piperidine (0.73 g) and acetic acid (50 ml) was stirred for 24 hours under reflux. The reaction mixture was concentrated under reduced pressure, and resulting crystalline precipitate was collected by filtration. The filtrate was dissolved in ethyl acetate. The solution was successively washed with a saturated aqueous solution of sodium hydrogencarbonate, water, 1N HCl and water, followed by drying ($MgSO_4$). The ethyl acetate layer was concentrated under reduced pressure. The concentrate was subjected to column chromatography on silica gel. From the fraction eluted with chloroform-methanol (50:1), further crystals were collected, which were combined with the crystalline product obtained above and dissolved in tetrahydrofuran (THF) (100 ml). To the solution was added palladium-carbon (5%, 1.0 g), which was subjected to catalytic hydrogenation under 1 atmospheric pressure at room temperature. The catalyst was filtered off, and the filtrate was concentrated. The concentrate was subjected to column chromatography on silica gel. From the fraction eluted with chloroform-methanol (50:1), 5-[3-[3-ethoxy-4-(2-phenyl-4-oxazolylmethoxy)phenyl]propyl]-2,4-oxazolidinedione was obtained, which was recrystallized from chloroform-ether to give colorless prisms, m.p.119–120° C.

WORKING EXAMPLE 12

In substantially the same manner as in Working Example 11, 4-[5-methyl-2-(2-naphthyl)-4-oxazolylmethoxy]-3-methoxycinnamaldehyde was condensed with 2,4-oxazolidinedione. The condensate was subjected to catalytic hydrogenation to yield 5-[3-[4-[5-methyl-2-(2-naphthyl)-4-oxazolylmethoxy]-3-methoxyphenyl]propyl]-2,4-oxazolidinedione. The product was recrystallized from chloroform-methanol-ether to give colorless prisms, m.p.173–174° C.

WORKING EXAMPLE 13

In substantially the same manner as in Working Example 11, 4-[2-(2-furyl)-5-methyl-4-oxazolylmethoxy]-3-methoxycinnamaldehyde was condensed with 2,4-oxazolidinedione. The condensate was subjected to catalytic hydrogenation to yield 5-[3-[4-2-(2-furyl)-5-methyl-4-oxazolylmethoxy]-3-methoxyphenyl]propyl]-2,4-oxazolidinedione. The product was recrystallized from dichloromethane-ether to give colorless prisms, m.p.127–129° C.

WORKING EXAMPLE 14

In substantially the same manner as in Working Example 11, 3-isopropoxy-4-(5-methyl-2-phenyl-4-oxazolylmethoxy)cinnamaldehyde was condensed with 2,4-oxazolidinedione. The condensate was subjected to catalytic hydrogenation to yield 5-[3-[3-isopropoxy-4-(5-methyl-2-phenyl-4-oxazolylmethoxy)phenyl]propyl]-2,4-oxazolidinedione, which was recrystallized from ethyl acetate-hexane to give colorless needles, m.p.120–121° C.

WORKING EXAMPLE 15

In substantially the same manner as in Working Example 11, (E,E)-5-[3-methoxy-4-(5-methyl-2-phenyl-4-oxazolylmethoxy)phenyl]-2,4-pentadien-1-al was condensed with 2,4-oxazolidinedione. The condensate was subjected to catalytic hydrogenation to yield 5-[5-[3-methoxy-4-(5-methyl-2-phenyl-4-oxazolylmethoxy)phenyl]pentyl]-2,4-oxazolidinedione. The product was recrystallized from dichloromethane-ether to give colorless prisms, m.p.114–115° C.

WORKING EXAMPLE 16

In substantially the same manner as in Working Example 11, 4-(5-methyl-2-phenyl-4-oxazolylmethoxy)-3-propoxycinnamaldehyde was condensed with 2,4-oxazolidinedione. The condensate was subjected to catalytic hydrogenation to yield 5-[3-[4-(5-methyl-2-phenyl-4-oxazolylmethoxy)-3-propoxyphenyl]propyl]-2,4-oxazolidinedione, which was recrystallized from ethyl acetate-ether to give colorless needles, m.p.119–120° C.

WORKING EXAMPLE 17

In substantially the same manner as in Working Example 11, 3-methoxy-4-(5-methyl-2-phenyl-4-oxazolyl-methoxy)cinnamaldehyde was condensed with 2,4-oxazolidinedione. The condensate was subjected to catalytic hydrogenation to yield 5-[3-[3-methoxy-4-(5-methyl-2-phenyl-4-oxazolylmethoxy)phenyl]propyl]-2,4-oxazolidinedione, which was recrystallized from ethyl acetate-hexane to give colorless prisms, m.p.161–162° C.

WORKING EXAMPLE 18

A mixture of 2-[5-[3-methoxy-4-(5-methyl-2-phenyl-4-oxazolylmethoxy)phenyl]pentyl]-1,3-dioxolan (3.6 g), 2,4-oxazolidinedione (1.7 g), piperidine (0.72 g) and acetic acid (50 ml) was stirred for 16 hours under reflux. The reaction mixture was concentrated under reduced pressure, which was dissolved in ethyl acetate. The solution was successively washed with a saturated aqueous solution of sodium hydrogencarbonate, water, 1N HCl and water, followed by drying ($MgSO_4$). The ethyl acetate layer was concentrated under reduced pressure, which was subjected to column chromatography on silica gel. From the fraction eluted with chloroform-methanol (50:1), was obtained 5-[6-[3-methoxy-4-(5-methyl-2-phenyl-4-oxazolylmethoxy)phenyl]hexylidene]-2,4-oxazolidinedione as an oily product. The oily product was dissolved in tetrahydrofuran (THF) (80 ml), to which was added palladium-carbon (5%, 1.0 g). The mixture was subjected to catalytic hydrogenation under 1 atmospheric pressure at room temperature. The catalyst was filtered off, and the filtrate was concentrated under reduced pressure. The concentrate was subjected to column chromatography on silica gel. From the fraction eluted with chloroform-methanol (50:1), was obtained 5-[6-[3-methoxy-4-(5-methyl-2-phenyl-4-oxazolylmethoxy)phenyl]hexyl]-2,4-oxazolidinedione, which was recrystallized from ethyl acetate-isopropyl ether to give colorless prisms, m.p.113–117° C.

WORKING EXAMPLE 19

In substantially the same manner as in Working Example 18, 2-[6-[3-methoxy-4-(5-methyl-2-phenyl-4-oxazolylmethoxy)phenyl]hexyl]-1,3-dioxolan was condensed with 2,4-oxazolidinedione. The condensate was subjected to catalytic hydrogenation to yield 5-[7-[3-methoxy-4-(5-methyl-2-phenyl-4-oxazolylmethoxy)phenyl]heptyl]-2,4-oxazolidinedione, which was recrystallized from ethyl acetate-hexane to give colorless prisms, m.p.109–111° C.

WORKING EXAMPLE 20

In substantially the same manner as in Working Example 18, 2-[3-[3-methoxy-4-(5-methyl-2-phenyl-4-oxazolylmethoxy)phenyl]propyl]-1,3-dioxolan was condensed with 2,4-oxazolidinedione. The condensate was subjected to catalytic hydrogenation to yield 5-[4-[3-methoxy-4-(5-methyl-2-phenyl-4-oxazolylmethoxy)phenyl]butyl]-2, 4-oxazolidinedione, which was recrystallized from dichloromethane-isopropyl ether to give colorless prisms, m.p.135–136° C.

WORKING EXAMPLE 21

A solution of titanium tetrachloride (TiCl$_4$) (1.1 g) in dichloromethane (5 ml) was added dropwise, at 0° C., to a solution of 5-[3-[3-isopropoxy-4-(5-methyl-2-phenyl-4-oxazolylmethoxy)phenyl]propyl]-2,4-oxazolidinedione (0.7 g) in dichloromethane (25 ml). The mixture was stirred for one hour at room temperature. The reaction mixture was poured over 2N HCl, which was stirred for 15 minutes at room temperature. The organic layer was separated, and the aqueous layer was subjected to extraction with chloroform. The organic layer combined was and successively washed with water, 2N HCl and water, which was dried (MgSO$_4$) and concentrated. The concentrate was subjected to column chromatography on silica gel. From the fraction eluted with chloroform-methanol (50:1), was obtained 5-[3-[3-hydroxy-4-(5-methyl-2-phenyl-4-oxazolylmethoxy)phenyl]propyl]-2,4-oxazolidinedione (0.22 g, 34%), which was recrystallized from chloroform-methanol to give colorless prisms, m.p.162–164° C.

WORKING EXAMPLE 22

In substantially the same manner as in Working Example 11, 3-fluoro-4-(5-methyl-2-phenyl-4-oxazolyl methoxy)cinnamaldehyde was condensed with 2,4-oxazolidinedione. The condensate was subjected to catalytic reduction to yield 5-[3-[3-fluoro-4-(5-methyl-2-phenyl-4-oxazolylmethoxy)phenyl]propyl]-2,4-oxazolidinedione, which was recrystallized from dichloromethane-methanol to give colorless prisms, m.p.180–181° C.

WORKING EXAMPLE 23

In substantially the same manner as in Working Example 11, 4-methoxy-3-(5-methyl-2-phenyl-4-oxazolyl-methoxy)cinnamaldehyde was condensed with 2,4-oxazolidinedione. The condensate was subjected to catalytic reduction to yield 5-[3-[4-methoxy-3-(5-methyl-2-phenyl-4-oxazolylmethoxy)phenyl]propyl]-2,4-oxazolidinedione, which was recrystallized from chloroform-methanol to give colorless prisms, m.p.185–187° C.

WORKING EXAMPLE 24

To a solution of methyl (R)-(+)-2-carbamoyloxy-5-[4-[2-(2-furyl)-5-methyl-4-oxazolylmethoxy]-3-methoxyphenyl]pentanoate (2.92 g) in chloroform (100 ml) was added dropwise, at temperature ranging from −5 to 0° C., 1,8-diazabicyclo[5.4.0]-7-undecene (DBU) (1.54 g). The mixture was stirred for one hour at the same temperature range. The reaction mixture was washed with 2N HCl and water, which was then dried (MgSO4) and concentrated to yield (R)-(+)-5-[3-[4-[2-(2-furyl)-5-methyl-4-oxazolylmethoxy]-3-methoxyphenyl]propyl]-2,4-oxazolidinedione (2.46 g, 91%), which was recrystallized from acetone-isopropyl ether to give colorless needles, m.p.122–123° C. [α]$_D$+39.4° (c=0. 495, CHCl$_3$)

WORKING EXAMPLE 25

In substantially the same manner as in Working Example 24, (S)-(−)-5-[3-[4-[2-(2-furyl)-5-methyl-4-oxazolylmethoxy]-3-methoxyphenyl]propyl]-2,4-oxazolidinedione was obtained from methyl (S)-(−)-2-carbamoyloxy-5-[4-[2-(2-furyl)-5-methyl-4-oxazolylmethoxy]-3-methoxyphenyl]pentanoate. The product was recrystallized from acetone-isopropyl ether to give colorless needles, m.p.1.22–123° C. [α]$_D$−39.8° (c=0. 500, CHCl$_3$).

WORKING EXAMPLE 26

In substantially the same manner as in Working Example 9, 5-[2-(4-hydroxy-3-methoxyphenyl)ethyl]-2,4-oxazolidinedione was reacted with 4-chloromethyl-5-methyl-2-phenyloxazole to obtain 5-[2-[4-(5-methyl-2-phenyl-4-oxazolylmethoxy)-3-methoxyphenyl]ethyl]-2,4-oxazolidinedione, which was recrystallized from ethyl acetate-chloroform to give colorless prisms, m.p.194–195° C.

WORKING EXAMPLE 27

In substantially the same manner as in Working Example 9, 5-[3-(4-hydroxy-3-methoxyphenyl)propyl]-2,4-oxazolidinedione was reacted with 4-bromoacetyl-5-methyl-2-phenyloxazole to obtain 5-[3-[3-methoxy-4-[2-(5-methyl-2-phenyl-4-oxazolyl)-2-oxoethoxy]phenyl]propyl]-2,4-oxazolidinedione as an oily product.

NMR(δ ppm in CDCl$_3$): 1.7–2.15(4H,m), 2.63(2H,t,J=7 Hz), 2.73(3H,s), 3.91(3H,s), 4.85(1H,dd,J=6.5&5 Hz), 5.43 (2H,s), 6.65(1H,dd,J=8&2 Hz), 6.73(1H,d,J=2 Hz), 6.79 (1H,d,J=8 Hz), 7.45–7.55(3H,m), 7.95(1H,br s), 8.0–8.1 (2H,m).

WORKING EXAMPLE 28

Sodium borohydride (0.045 g) was added portionwise, at room temperature, to a solution of 5-[3-[3-methoxy-4-[2-(5-methyl-2-phenyl-4-oxazolyl)-2-oxoethoxy]phenyl)propyl]-2,4-oxazolidinedione (0.37 g) in tetrahydrofuran (THF) (5 ml)-ethanol (5 ml). The mixture was stirred for 2 hours at room temperature. The reaction mixture was poured into water, which was acidified with 2N HCl, followed by extraction with ethyl acetate. The ethyl acetate layer was washed with water, dried (MgSO$_4$), followed by distilling off the solvent. The residual oily product was subjected to column chromatography on silica gel. From the fraction eluted with chloroform-methanol (100:1, v/v), was obtained 5-[3-[4-[2-hydroxy-2-(5-methyl-2-phenyl-4-oxazolyl)ethoxy]-3-methoxyphenyl)propyl]-2,4-oxazlidinedione (0.31 g, 83%), which was recrystallized from acetone-isopropyl ether to give colorless prisms, m.p.151–152° C.

WORKING EXAMPLE 29

In substantially the same manner as in Working Example 11, 3-methoxy-4-[1-(5-methyl-2-phenyl-4-oxazolyl)ethoxy]cinnamaldehyde was condensed with 2,4-oxazolidinedione. The condensate was subjected to catalytic hydrogenation to yield 5-[3-[3-methoxy-4-[1-(5-methyl-2-phenyl-4-oxazolyl)ethoxy]phenyl]propyl]-2,4-oxazolidinedione.

NMR(δ ppm in CDCl$_3$): 1.73(3H,d,J=6.5 Hz), 1.7–2.1 (4H,m), 2.28(3H,s), 2.59(2H,t,J=7 Hz), 3.85(3H,s), 4.82 (1H,dd,J=7&4.5 Hz), 5.32(1H,q,J=6.5 Hz), 6.59(1H,dd,J= 8&2 Hz), 6.68(1H,d,J=2 Hz), 6.78(1H,d,J=8 Hz), 7.35–7.5 (3H,m), 7.95–8.1(2H,m), 8.66(1H,br s).

WORKING EXAMPLE 30

A mixture of 5-[3-[3-methoxy-4-[2-[(E)-styryl]-4-oxazolylmethoxy]phenyl]propyl]-2,4-oxazolidinedione (0.64 g), paradium-carbon (5%, 1.3 g) and tetrahydrofuran (THF) (35 ml) was subjected to catalytic hydrogenation under 1 atmospheric pressure at room temperature. The catalyst was filtered off, and the filtrate was concentrated under reduced pressure to yield 5-[3-[3-methoxy-4-[2-(2-phenylethyl)-4-oxazolylmethoxy]phenyl]propyl]-2,4-oxazolidinedione (0.43 g, 67%). The product was recrystallized from ethyl acetate-hexane to give colorless needles, m.p.122–123° C.

WORKING EXAMPLE 31

In substantially the same manner as in Working Example 30, 5-[3-[3-methoxy-4-[2-[(E)-styryl]-4-thiazolylmethoxy]phenyl]propyl]-2,4-oxazolidinedione was subjected to catalytic hydrogenation under 1 atmospheric pressure at room temperature to yield 5-[3-[3-methoxy-4-[2-(2-phenylethyl)-4-thiazolylmethoxy]phenyl]propyl]-2,4-oxazolidinedione. The product was recrystallized from ethyl acetate-hexane to give colorless needles, m.p.136–137° C.

WORKING EXAMPLE 32

In substantially the same manner as in Working Example 9, 5-[3-(4-hydroxy-3-methoxyphenyl)propyl]-2,4-oxazolidinedione was reacted with 4-chloromethyl-5-methyl-2-phenylthiazole to obtain 5-[3-[3-methoxy-4-(5-methyl-2-phenyl-4-thiazolylmethoxy)phenyl]propyl]-2,4-oxazolidinedione, which was recrystallized from ethyl acetate-chloroform to give colorless prisms, m.p.128–129° C.

WORKING EXAMPLE 33

In substantially the same manner as in Working Example 9, 5-[3-(4-hydroxy-3-methoxyphenyl)propyl]-2,4-oxazolidinedione was reacted with 5-chloromethyl-3-phenyl-1,2,4-oxadiazole to obtain 5-[3-[3-methoxy-4-(3-phenyl- 1,2,4-oxadiazol-5-ylmethoxy)phenyl]propyl]-2,4-oxazolidinedione, which was recrystallized from ethyl acetate-hexane to give colorless prisms, m.p.110–111° C.

WORKING EXAMPLE 34

A mixture of ethyl 6-(4-benzyloxy-3-methoxyphenyl)-2-hydroxyhexanoate (15.22 g), potassium cyanate (KCNO) (13.26 g) and butanol (180 ml) was stirred for 72 hours under reflux. The reaction mixture was concentrated under reduced pressure. The residue was poured into water, which was acidified with 2N HCl, followed by extraction with ethyl acetate. The ethyl acetate layer was washed with water, dried (MgSO$_4$), followed by distilling off the solvent. The residual oily product was subjected to column chromatography on silica gel. From the fraction eluted with ethyl acetate-hexane (1:1, v/v), was obtained 5-[4-(4-benzyloxy-3-methoxyphenyl)butyl]-2,4-oxazolidinedione (11.22 g, 74%), which was recrystallized from ethyl acetate-hexane to give colorless prisms, m.p.92–93° C.

WORKING EXAMPLE 35

In substantially the same manner as in Working Example 9, 5-[4-(4-hydroxy-3-methoxyphenyl)butyl]-2,4-oxazolidinedione was reacted with 4-chloromethyl-5-methyl-2-[(E)-styryl]oxazole to obtain 5-[4-[3-methoxy-4-[2-[(E)-styryl]-4-oxazolylmethoxy]phenyl]butyl]-2,4-oxazolidinedione, which was recrystallized from ethyl acetate-hexane to give colorless prisms, m.p.171–172° C.

WORKING EXAMPLE 36

In substantially the same manner as in Working Example 9, 5-[4-(4-hydroxy-3-methoxyphenyl)butyl]-2,4-oxazolidinedione was reacted with 4-chloromethyl-5-methyl-2-[(E)-styryl]thiazole to obtain 5-[4-[3-methoxy-4-[2-[(E)-styryl]-4-thiazolylmethoxy]phenyl]butyl]-2,4-oxazolidinedione, which was recrystallized from ethyl acetate-hexane to give colorless prisms, m.p.167–168° C.

WORKING EXAMPLE 37

In substantially the same manner as in Working Example 34, ethyl 4-(4-benzyloxy-3-ethoxyphenyl)-2-hydroxybutanoate was reacted with potassium cyanate (KCNO) to obtain 5-[2-(4-benzyloxy-3-ethoxyphenyl)ethyl]-2,4-oxazolidinedione, which was recrystallized from ethyl acetate-hexane to give colorless prisms, m.p.143–144° C.

WORKING EXAMPLE 38

In substantially the same manner as in Working Example 34, ethyl 4-(3-benzyloxy-4-methoxyphenyl)-2-hydroxybutanoate was reacted with potassium cyanate (KCNO) to obtain 5-[2-(3-benzyloxy-4-methoxyphenyl)ethyl]-2,4-oxazolidinedione as an oily product.

NMR(δ ppm in CDCl$_3$): 1.95–2.25(2H,m), 2.59–2.84(2H, m), 3.87(3H,s), 4.58(1H,dd,J=8.2&4.8 Hz), 5.15(2H,s), 6.72–6.86(3H,m), 7.26–7.45(5H,m), 8.52(1H,br s).

WORKING EXAMPLE 39

In substantially the same manner as in Working Example 9, 5-[4-(4-hydroxy-3-methoxyphenyl)butyl]-2,4-oxazolidinedione was reacted with 4-chloromethyl-2-[(E)-2-(2-naphthyl)ethyl]oxazole to obtain 5-[4-[3-methoxy-4-[2-[(E)-2-(2-naphthyl)ethenyl]-4-oxazolylmethoxy]phenyl]butyl]-2,4-oxazolidinedione, which was recrystallized from ethyl acetate-hexane to give colorless prisms, m.p.169–170° C.

WORKING EXAMPLE 40

In substantially the same manner as in Working Example 1, 4-benzyloxy-3,5-dimethoxycinnamaldehyde was condensed with 2,4-oxazolidinedione to obtain 5-[3-(4-benzyloxy-3,5-dimethoxy)cinnamilidene]-2,4-oxazolidinedione, which was recrystallized from ethyl acetate-hexane to give yellow prisms, m.p.181–182° C.

WORKING EXAMPLE 41

In substantially the same manner as in Working Example 9, 5-[3-(4-hydroxy-3,5-dimethoxyphenyl)propyl]-2,4-oxazolidinedione was reacted with 4-chloromethyl-5-methyl-2-[(E)-styryl]oxazole to obtain 5-[3-[3,5-dimethoxy-4-[2-[(E)-styryl]-4-oxazolylmethoxy]phenyl]propyl]-2,4-oxazolidinedione, which was recrystallized from ethyl acetate-hexane to give colorless prisms, m.p.94–95° C.

WORKING EXAMPLE 42

1-Dodecanethiol (2.37 g) was added, at 0° C., to a suspension of aluminum chloride (1.56 g) in dichloromethane (30 ml), which was stirred for 10 minutes. To the mixture, was added dropwise, at the same temperature, a solution of 5-[3-[4-[2-furyl)-5-methyl-4-oxazolylmethoxy]-3-methoxyphenyl]propyl]-2,4-oxazolidinedione (0.5 g) in dichloromethane (10 ml). The reaction mixture was stirred for 2 hours at room temperature, poured into ice-water, followed by extraction with dichloromethane. The dichloromethane layer was washed with water, dried (MgSO$_4$), followed by distilling off the solvent. The residual oily product was subjected to column chromatography on silica gel. From the fraction eluted with ethyl acetate-chloroform (1:3, v/v), was obtained 5-[3-[4-[2-(2-furyl)-5-methyl-4-oxazolylmethoxy]-3-hydroxyphenyl]propyl]-2,4-oxazolidinedione (0.21 g, 43%), which was recrystallized from dichloromethane-methanol to give colorless prisms, m.p.152–153° C.

WORKING EXAMPLE 43

In substantially the same manner as in Working Example 11, 3-fluoro-4-[2-[N-methyl-N-(2-pyridyl)amino]ethoxy] cinnamaldehyde was condensed with 2,4-oxazolidinedione. The condensate was subjected to catalytic hydrogenation to yield 5-[3-[3-fluoro-4-[2-[N-methyl-N-(2-pyridyl)amino] ethoxy]phenyl]propyl-2,4-oxazolidinedione, which was recrystallized from ethyl acetate-hexane to give colorless prisms, m.p.124–125° C.

Formulation Example 1 (Preparation of tablets)

| (1) | 5-[3-[3-methoxy-4-(5-methyl-2-phenyl-4-oxazolyl methoxy)phenyl]propyl]-2,4-oxazolidinedione (compound produced in Working Example 17) | 10 g |
|---|---|---|
| (2) | lactose | 50 g |
| (3) | corn starch | 15 g |
| (4) | carboxymethylcellulose calcium | 44 g |
| (5) | magnesium stearate | 1 g |
| | 1000 tablets | 120 g |

The whole amounts of (1), (2) and (3), and 30 g of (4) were kneaded with water, which was subjected to vacuum drying, followed by granulation. Thus-granulated powder was mixed with 14 g of (4) and 1 g of (5), followed by tableting using a tableting machine to prepare 1000 tablets containing 10 mg of (1) per tablet.

Formulation Example 2 (Preparation of tablets)

| (1) | 5-[3-[3-fluoro-4-(5-methyl-2-phenyl-4-oxazoylmethoxy)phenyl]propyl]-2,4-oxazolidinedione (compound produced in Working Example 22) | 30 g |
|---|---|---|
| (2) | lactose | 50 g |
| (3) | corn starch | 15 g |
| (4) | carboxymethylcellulose calcium | 44 g |
| (5) | magnesium stearate | 1 g |
| | 1000 tablets | 140 g |

The whole amounts of (1), (2) and (3), and 30 g of (4) were kneaded with water, which was subjected to vacuum drying, followed by granulation. Thus-granulated powder was mixed with 14 g of (4) and 1 g of (5), which was tableted by using a tableting machine to prepare 1000 tablets containing 30 mg of (1) per tablet.

Reference Example 1

A mixture of cinnamamide (25.3 g) and 1,3-dichloroacetone (20.9 g) was heated for one hour at 130° C. The reaction mixture was poured into water, which was neutralized with potassium carbonate, followed by extraction with ethyl acetate. The ethyl acetate layer was washed with water, dried (MgSO$_4$) and concentrated. The concentrate was purified by column chromatography on silica gel. From the fraction eluted with ether-hexane (1:5, v/v), was obtained 4-chloromethyl-2-[(E)-styryl] oxazole (16.9 g, 47%), which was recrystallized from ether-hexane to yield colorless needless, m.p.72–73° C.

Reference Example 2

A mixture of thiocinnamamide (11.7 g), 1,3-dichloroacetone (9.1 g) and ethanol (145 ml) was stirred for one hour under reflux. The reaction mixture was poured into ice-water, which was neutralized with potassium carbonate, followed by extraction with ethyl acetate. The ethyl acetate layer was washed with water, dried (MgSO$_4$) and concentrated. The concentrate was purified by means of column chromatography on silica gel. From the fraction eluted with ether-hexane (1:6, v/v), was obtained 4-chloromethyl-2-[(E)-styryl]thiazole (9.4 g, 56%), which was recrystallized from ether-hexane to yield colorless plates, m.p.88–89° C.

Reference Example 3

A mixture of 4-chloromethyl-2-phenyloxazole (10.0 g), vaniline (7.9 g), potassium carbonate (8.6 g) and N,N-dimethylformamide (DMF) (90 ml) was stirred for 2 hours at 100° C. The reaction mixture was poured into ice-water. Resulting crystalline precipitate was collected by filtration, which was dissolved in chloroform (400 ml). The chloroform layer was washed with water, dried (MgSO$_4$) and concentrated. Residual crystalline product was collected by filtration to yield 3-methoxy-4-(2-phenyl-4-oxazolylmethoxy)benzaldehyde (15.4 g, 97%), which was recrystallized from ethyl acetate-hexane to give colorless prisms, m.p.119–120° C.

Reference Examples 4 to 12

In substantially the same manner as in Reference Example 3, compounds set forth in Table 3 were produced.

TABLE 3
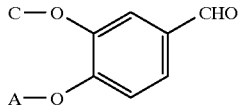
| No. of R. Ex. | A | C | m.p. (° C.) | Recrystallization solvent |
|---|---|---|---|---|
| 4 | 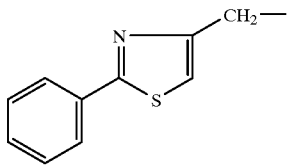 | CH₃— | 83–84 | ethyl acetate-hexane |
| 5 | (CH₃)₂CH— | CH₃— | oil[1] | |
| 6 | 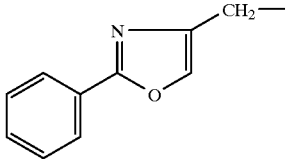 | C₂H₅— | 107–108 | dichloromethane-isopropyl ether |
| 7 | 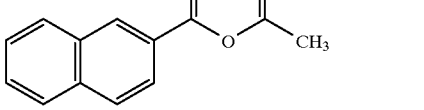 | CH₃— | 156–157 | dichloromethane-ether |
| 8 | 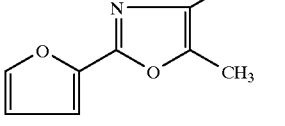 | CH₃— | 131–132 | dichloromethane-ethyl acetate |
| 9 | 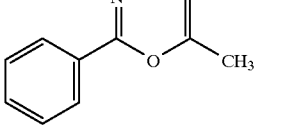 | (CH₃)₂CH— | 127–128 | ethyl acetate |
| 10 | 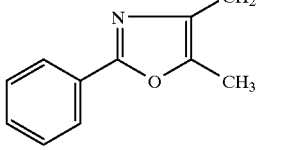 | CH₃CH₂CH₂— | 109–110 | ethyl acetate-hexane |
| 11 | 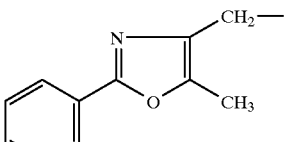 | C₂H₅— | 142–143 | dichloromethane-ether |

TABLE 3-continued

[Structure: benzene ring with C—O and A—O substituents and CHO group]

| No. of R. Ex. | A | C | m.p. (° C.) | Recrystallization solvent |
|---|---|---|---|---|
| 12 | [2-phenyl-oxazol-4-yl with CH₃ at 5-position]-CH₂— | CH₃— | 126–127 | ethyl acetate-hexane |

1) b.p.: 122–124° C./0.25 mmHg

Reference Example 13

Sodium hydride (60% in oil, 1.93 g) was added portionwise, at 0° C., to a solution of triethyl phosphonoacetate (10.81 g) and 3-methoxy-4-(2-phenyl-4-oxazolylmethoxy)benzaldehyde (14.62 g) in N,N-dimethylformamide (DMF)(230 ml). The mixture was stirred for one hour at room temperature. The reaction mixture was poured into ice-water, which was subjected to extraction with ethyl acetate. The ethyl acetate layer was washed with water, dried (MgSO$_4$) and concentrated to yield ethyl 3-methoxy-4-(2-phenyl-4-oxazolylmethoxy) cinnamate (17.24 g, 96%), which was recrystallized from ethyl acetate-hexane to give colorless needles, m.p.128–129° C.

Reference Examples 14 to 15

In substantially the same manner as in Reference Example 13, compounds set forth in Table 4 were produced.

TABLE 4

[Structure: benzene ring with C—O and A—O substituents and CH=CH—COOC₂H₅ group]

| No. of R. Ex. | A | C | m.p. (° C.) | Recrystallization solvent |
|---|---|---|---|---|
| 14 | [2-phenyl-thiazol-4-yl]-CH₂— | CH₃— | 92–93 | ethyl acetate-hexane |
| 15 | (CH₃)₂CH— | CH₃— | 103–104 | ethyl acetate-hexane |

Reference Example 16

A methanol solution of sodium methoxide (28%, 3.4 g) was added dropwise to an ice-cooled solution of trimethyl phosphonoacetate (3.2 g) and 3-ethoxy-4-(2-phenyl-4-oxazolylmethoxy)benzaldehyde (5.1 g) in N,N-dimethylformamide (DMF) (30 ml). The mixture was stirred for 5 minutes under ice-cooling, then for 4 hours at room temperature. The reaction mixture was poured into ice-water, which was subjected to extraction with ethyl acetate. The ethyl acetate layer was washed with water, dried (MgSO$_4$) and concentrated to yield methyl 3-ethoxy-4-(2-phenyl-4-oxazolylmethoxy)cinnamate (5.5 g, 91%), which was recrystallized from chloroform-ether to give colorless prisms, m.p.125–126° C.

Reference Examples 17 to 22

In substantially the same manner as in Reference Example 16, compounds set forth in Table 5 were produced.

TABLE 5

Structure: C—O—[benzene ring with COOCH₃ cinnamate (E)]—O—A

| No. of R. Ex. | A | C | m.p. (°C) | Recrystallization solvent |
|---|---|---|---|---|
| 17 | 2-(naphthalen-2-yl)-5-methyl-oxazol-4-yl-CH₂— | CH₃— | 161–162 | chloroform-ether |
| 18 | 2-(furan-2-yl)-5-methyl-oxazol-4-yl-CH₂— | CH₃— | 129–130 | dichloromethane-ether |
| 19 | 2-phenyl-5-methyl-oxazol-4-yl-CH₂— | $(CH_3)_2CH-$ | 125–126 | ethyl acetate-ether |
| 20 | 2-phenyl-5-methyl-oxazol-4-yl-CH₂— | $CH_3CH_2CH_2-$ | 118–119 | ethyl acetate |
| 21 | 2-phenyl-5-methyl-oxazol-4-yl-CH₂— | $C_2H_5-$ | 121–122 | dichloromethane-isopropyl ether |
| 22 | 2-phenyl-5-methyl-oxazol-4-yl-CH₂— | CH₃— | 140–141 | ethyl acetate-hexane |

Reference Example 23

In substantially the same manner as in Reference Example 16, 3-methoxy-4-(5-methyl-2-phenyl-4-oxazolylmethoxy)cinnamaldehyde was allowed to react with trimethyl phosphonoacetate to produce methyl (E,E)-5-[3-methoxy-4-(5-methyl-2-phenyl-4-oxazolylmethoxy)phenyl]-2,4-pentadienoate, which was recrystallized from ethyl acetate to give colorless prisms, m.p.166–167° C.

Reference Example 24

A toluene solution of diisobutylaluminum hydride (1.5M, 72.2 ml) was added dropwise, at 0° C., to a solution of ethyl 3-methoxy-4-(2-phenyl-4-oxazolylmethoxy)cinnamate (16.4 g) in tetrahydrofuran (THF) (240 ml). The mixture was stirred for 2 hours at room temperature, to which was added, under ice-cooling, methanol (7 ml). The reaction mixture was poured into 2N HCl (600 ml), which was subjected to extraction with ethyl acetate. The ethyl acetate layer was washed with water, dried (MgSO₄) and concentrated to yield (E)-3-[3-methoxy-4-(2-phenyl-4-oxazolylmethoxy)phenyl]-2-propen-1-ol (14.4 g, 98%), which was recrystallized from ethyl acetate-hexane to give colorless needles, m.p.113–114° C.

Reference Examples 25 to 32

In substantially the same manner as in Reference Example 24, compounds set forth in Table 6 were produced.

TABLE 6

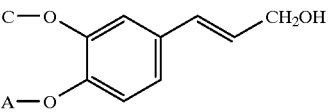

| No. of R. Ex. | A | C | m.p. (° C.) | Recrystallization solvent |
|---|---|---|---|---|
| 25 | 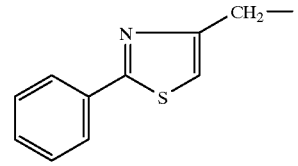 | $CH_3-$ | 71–72 | ethyl acetate-hexane |
| 26 | 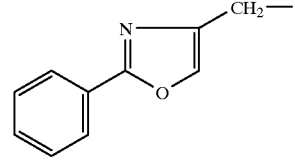 | $C_2H_5-$ | 120–121 | ethyl acetate-ether |
| 27 | 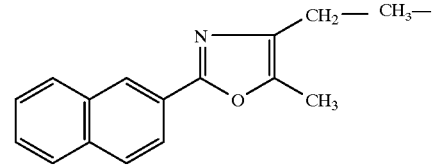 | $CH_3-$ | 149–150 | chloroform-ether |
| 28 | 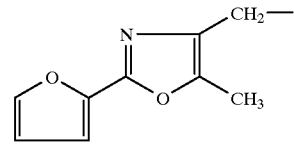 | $CH_3-$ | 128–129 | dichloromethane-ether |
| 29 | 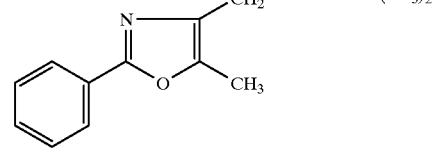 | $(CH_3)_2CH-$ | 108–109 | ethyl acetate-ether |
| 30 | 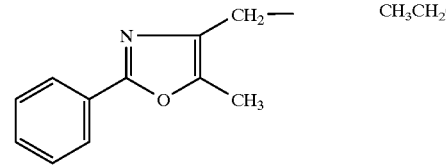 | $CH_3CH_2CH_2-$ | 127–128 | ethyl acetate-ether |
| 31 | 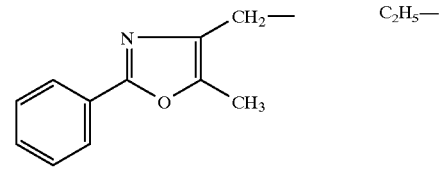 | $C_2H_5-$ | 152–153 | chloroform-ethyl acetate |

TABLE 6-continued

Structure: C—O and A—O on phenyl ring with CH=CH—CH₂OH substituent

| No. of R. Ex. | A | C | m.p. (°C.) | Recrystallization solvent |
|---|---|---|---|---|
| 32 | 2-phenyl-5-methyl-oxazol-4-yl-CH₂— | CH₃— | 137–138 | ethyl acetate-ether |

Reference Example 33

In substantially the same manner as in Reference Example 24, methyl (E,E)-5-[3-methoxy-4-(5-methyl-2-phenyl-4-oxazolylmethoxy)phenyl]-2,4-pentadienoate was subjected to reduction with diisobutylaluminum hydride to yield (E,E)-5-[3-methoxy-4-(5-methyl-2-phenyl-4-oxazolylmethoxy)phenyl]-2,4-pentadien-1-ol, which was recrystallized from ethyl acetate to give colorless needles, m.p.149–151° C.

Reference Example 34

A solution of aluminum chloride (AlCl₃) (6.1 g) in ether (70 ml) was added dropwise at 0° C. to a suspension of lithium aluminum hydride (LiAlH₄) (6.4 g) in ether (270 ml). The mixture was stirred for 10 minutes at room temperature, to which was then added dropwise, at room temperature, a solution of ethyl 4-isopropoxy-3-methoxy cinnamate (35.4 g) in ether-tetrahydrofuran (THF) (3:1, 220 ml). The mixture was stirred for 2 hours at room temperature, to which were added dropwise, under ice-cooling, water (170 ml) and 6N H₂SO₄ (230 ml). The organic layer was separated, and the aqueous layer was subjected to extraction with ether. The organic layers were combined, washed with water, dried (MgSO₄) and concentrated. The concentrate was subjected to column chromatography on silica gel. From the fraction eluted with ethyl acetate-hexane (1:2, v/v), was obtained (E)-3-(4-isopropoxy-3-methoxyphenyl)-2-propen-1-ol (27.0 g, 91%).

NMR (δ ppm in CDCl₃): 1.37(6H,d,J=6 Hz), 1.52(1H,s), 3.87(3H,s), 4.30(2H,dd,J=6&1 Hz), 4.52(1H,m), 6.24(1H, dt,J=16&6 Hz), 6.55(1H,d,J=16 Hz), 6.83(1H,d,J=8 Hz), 6.90(1H,dd,J=8&2 Hz), 6.94(1H,d,J=2 Hz).

Reference Example 35

Activated manganese dioxide (28.0 g) was added to a solution of (E)-3-[3-methoxy-4-(2-phenyl-4-oxazolyl-methoxy)phenyl]-2-propen-1-ol (13.6 g) in chloroform (250 ml). The mixture was stirred for 8 hours at room temperature, which was subjected to filtration through a celite layer. The filtrate was concentrated to yield 3-methoxy-4-(2-phenyl-4-oxazolylmethoxy) cinnamaldehyde (11.8 g, 88%), which was recrystallized from ethyl acetate-hexane to give colorless needles, m.p.144–145° C.

Reference Examples 36 to 44

In substantially the same manner as in Reference Example 35, compounds set forth in Table 7 were produced.

TABLE 7

Structure: C—O and A—O on phenyl ring with CH=CH—CHO substituent

| No. of R. Ex. | A | C | m.p. (°C.) | Recrystallization solvent |
|---|---|---|---|---|
| 36 | 2-phenyl-thiazol-4-yl-CH₂— | CH₃— | 115–116 | ethyl acetate-hexane |
| 37 | (CH₃)₂CH— | CH₃— | 93–94 | ethyl acetate-hexane |

TABLE 7-continued

Structure: C—O—[benzene ring]—CH=CH—CHO with A—O— substituent

| No. of R. Ex. | A | C | m.p. (° C.) | Recrystallization solvent |
|---|---|---|---|---|
| 38 | 2-phenyl-oxazol-4-yl-CH₂— | C₂H₅— | 148–149 | chloroform-ether |
| 39 | 2-(2-naphthyl)-5-methyl-oxazol-4-yl-CH₂— | CH₃— | 187–188 | dichloromethane-hexane |
| 40 | 2-(2-furyl)-5-methyl-oxazol-4-yl-CH₂— | CH₃— | 125–126 | dichloromethane-hexane |
| 41 | 5-methyl-2-phenyl-oxazol-4-yl-CH₂— | (CH₃)₂CH— | 114–115 | ethyl acetate-ether |
| 42 | 5-methyl-2-phenyl-oxazol-4-yl-CH₂— | CH₃CH₂CH₂— | 156–157 | ethyl acetate |
| 43 | 5-methyl-2-phenyl-oxazol-4-yl-CH₂— | C₂H₅— | 172–173 | dichloromethane-ethyl acetate |
| 44 | 5-methyl-2-phenyl-oxazol-4-yl-CH₂— | CH₃— | 159–160 | ethyl acetate |

Reference Example 45

In substantially the same manner as in Reference Example 35, (E,E)-5-[3-methoxy-4-(5-methyl-2-phenyl-4-oxazolylmethoxy)phenyl]-2,4-pentadien-1-ol was subjected to oxidation with activated manganese dioxide to yield (E,E)-5-[3-methoxy-4-(5-methyl-2-phenyl-4-oxazolylmethoxy)phenyl]-2,4-pentadien-1-al, which was recrystallized from ethyl acetate to give colorless needles, m.p.133–134° C.

Reference Example 46

A solution of titanium tetrachloride (TiCl$_4$) (10.6 g) in dichloromethane (10 ml) was added dropwise, at 0° C., to a solution of 5-[3-(4-isopropoxy-3-methoxy-phenyl)propyl]-2,4-oxazolidinedione (4.3 g) in dichloromethane (130 ml). The mixture was stirred for one hour at 0° C., which was poured into 2N HCl, followed by stirring for 15 minutes at room temperature. The organic layer was separated, and the aqueous layer was subjected to extraction with chloroform. The organic layers were combined, washed successively with water, 2N HCl and water, which was dried (MgSO$_4$), followed by concentration to yield 5-[3-(4-hydroxy-3-methoxyphenyl)propyl]-2,4-oxazolidinedione (2.8 g, 76%). Recrystallization of the product from ethanol-hexane gave colorless prisms, m.p.147–148° C.

Reference Example 47

A mixture of 3-methoxy-4-(5-methyl-2-phenyl-4-oxazolylmethoxy)cinnamaldehyde (5.6 g), palladium-carbon (5%, 0.5 g) and tetrahydrofuran (THF) (160 ml) was subjected to catalytic hydrogenation at room temperature under 1 atmospheric pressure. The catalyst was filtered off, and the filtrate was concentrated under reduced pressure. The concentrate was subjected to column chromatography on silica gel. From the fraction eluted with ethyl acetate -hexane (1:1), was obtained 3-[3-methoxy-4-(5-methyl-2-phenyl-4-oxazolylmethoxy)phenyl]propionaldehyde, which was recrystallized from ethyl acetate-hexane to give colorless needles, m.p.80–81° C.

Reference Example 48

To a suspension of [2-(1,3-dioxolan-2-yl)ethyl] triphenylphosphonium bromide (6.7 g) in tetrahydrofuran (THF) (60 ml) was added dropwise, at –30° C. in nitrogen streams, a hexane solution of n-butyl lithium (1.6M, 9.4 ml). The mixture was stirred for one hour at the same temperature, to which was then added dropwise, at –30° C., a solution of 3-[3-methoxy-4-(5-methyl-2-phenyl-4-oxazolylmethoxy) phenyl]propionaldehyde (4.1 g) in tetrahydrofuran (THF) (10 ml). The cooling bath was removed, and the reaction mixture was stirred for further one hour at room temperature. The reaction mixture was poured into water, which was subjected to extraction with ethyl acetate. The ethyl acetate layer was washed with water and dried (MgSO$_4$), followed by distilling off the solvent under reduced pressure. The residue was subjected to column chromatography on silica gel. From the fraction eluted with ethyl acetate-hexane (1:2), was obtained 2-[5-[3-methoxy-4-(5-methyl-2-phenyl-4-oxazolylmethoxy) phenyl]-3-pentenyl]-1,3-dioxolan as an oily product (4.5 g). This oily product was dissolved in methanol (50 ml)—tetrahydrofuran (THF) (30 ml). To the solution was added palladium-carbon (5%, 0.5 g), which was subjected to catalytic hydrogenation at room temperature under 1 atmospheric pressure. The catalyst was filtered off, and the filtrate was concentrated under reduced pressure to give 2-[5-[3-methoxy-4-(5-methyl-2-phenyl-4-oxazolylmethoxy)phenyl]pentyl]-1,3-dioxolan (3.8 g, 75%), which was recrystallized from ethyl acetate-hexane to give colorless needles, m.p.81–82° C.

Reference Example 49

In substantially the same manner as in Reference Example 48, the reaction product obtained by the reaction of [2-(1, 3-dioxolan-2-yl)ethyl]triphenylphosphonium bromide with 3-methoxy-4-(5-methyl-2-phenyl- 4-oxazolylmethoxy) benzaldehyde was subjected to catalytic hydrogenation to yield 2-[3-[3-methoxy-4-(5-methyl-2-phenyl-4-oxazolylmethoxy)phenyl]propyl]-1,3-dioxolan, which was recrystallized from ethyl acetate-hexane to give colorless prisms, m.p.74–75° C.

Reference Example 50

To a suspension of (5-ethoxycarbonylpentyl) triphenylphosphonium bromide (3.0 g) in tetrahydrofuran (THF) (70 ml) was added dropwise, in nitrogen streams at –30° C., a hexane solution of n-butyl lithium (1.6M, 3.9 ml). The mixture was stirred for 30 minutes at the same temperature, to which was added dropwise at –30° C. a solution of 3-methoxy-4-[5-methyl-2-phenyl-4-oxazolylmethoxy)benzaldehyde (1.0 g) in tetrahydrofuran (THF) (10 ml). The mixture was stirred for 4 hours at temperature ranging from 50 to 60° C. The reaction mixture was then poured into water, which was subjected to extraction with ethyl acetate. The ethyl acetate layer was washed with water and dried (MgSO$_4$), followed by distilling off the solvent under reduced pressure. The residue was subjected to column chromatography on silica gel. From the fraction eluted with ethyl acetate-hexane (1:4), was obtained ethyl 7-[3-methoxy-4-(5-methyl-2-phenyl-4-oxazolylmethoxy) phenyl]heptanoate (9.7 g, 85%) as an oily product.

NMR (δ ppm in CDCl$_3$): 1.25–1.75(11H,m), 2.29(2H,t, J=7.5 Hz), 2.40(3H,s), 2.55(2H,t,J=7.6 Hz), 3.86(3H,s), 4.12(2H,q,J=7.1 Hz), 5.03(2H,s), 6.65–6.75(2H,m), 6.95 (1H,d,J=8 Hz), 7.38–7.51(3H,m), 7.95–8.08(2H,m).

Reference Example 51

A solution of ethyl 7-[3-methoxy-4-(5-methyl-2-phenyl-4-oxazolylmethoxy)phenyl]heptanoate (9.6 g) in tetrahydrofuran (THF) (50 ml) was added dropwise, at room temperature, to a suspension of lithium aluminum hydride (0.96 g) in tetrahydrofuran (THF) (50 ml). The mixture was stirred for 30 minutes at room temperature, to which was then added, under ice-cooling, water (6 ml). Insolubles were filtered off, then the filtrate was concentrated. The concentrate was subjected to column chromatography on silica gel. From the fraction eluted with ethyl acetate-hexane (2:3), was obtained 7-[3-methoxy-4-(5-methyl-2-phenyl-4-oxazolylmethoxy)phenyl]heptanol, which was recrystallized from chloroform-ether to give colorless needles, m.p.78–79° C.

Reference Example 52

A solution of dimethyl sulfoxide (DMSO) (4 g) in dichloromethane (10 ml) was added dropwise, at temperatures ranging from –60 to –50° C., to a solution of oxalyl chloride [(COCl$_2$)] (2.9 g) in dichloromethane (100 ml). The mixture was stirred for 10 minutes at the same temperature range, to which was then added dropwise a solution of 7-[3-methoxy-4-(5-methyl-2-phenyl-4-oxazolylmethoxy)phenyl]heptanol (4.3 g) in dichloromethane (15 ml). The mixture was stirred for 30 minutes at 0° C., to which was added dropwise at –20° C. triethylamine (10.6 g). The mixture was stirred for further 30 minutes at the same temperature. The reaction mixture was poured into water, which was subjected to extraction with ethyl acetate. The ethyl acetate layer was washed with water and dried (MgSO$_4$), followed by distilling off the solvent under reduced pressure. The residue was subjected to column chromatography on silica gel. From the fraction eluted with ethyl acetate-hexane (1:3), was obtained 7-[3-methoxy-4-(5-methyl-2-phenyl-4-oxazolylmethoxy)-phenyl]heptanal, which was recrystallized from ethyl acetate-hexane to give colorless prisms, m.p.64–65° C.

Reference Example 53

A mixture of 7-[3-methoxy-4-(5-methyl-2-phenyl-4-oxazolylmethoxy)phenyl]heptanal (3.8 g), ethylene glycol (1 g), p-toluenesulfonic acid monohydrate and toluene (50 ml) was stirred for 4 hours under reflux. The reaction mixture was cooled, which was then washed with water and dried ($MgSO_4$), followed by distilling off the solvent under reduced pressure. The residue was subjected to column chromatography on silica gel. From the fraction eluted with ethyl acetate-hexane (1:3), was obtained 2-[6-[3-methoxy-4-(5-methyl-2-phenyl-4-oxazolylmethoxy)phenyl]hexyl]-1,3-dioxolan (3.9 g, 94%) as an oily product.

NMR (δ ppm in $CDCl_3$): 1.20–1.74(10H,m), 2.40(3H,s), 2.54(2H,t,J=7.6 Hz), 3.72–4.01(4H,m), 3.86(3H,s), 4.84 (1H,t,J=4.7 Hz), 5.02(2H,s), 6.62–6.76(2H,m), 6.95(1H,d, J=7.8 Hz), 7.36–7.52(3H,m), 7.95–8.08(2H,m).

Reference Example 54

Sodium hydride (60% in oil, 2.2 g) was added portionwise, at 0° C., to a solution of 3,4-difluoronitrobenzene (8.8 g) and 5-methyl-2-phenyl-4-oxazolyl methanol (10.0 g) in N,N-dimethylformamide (DMF) (100 ml). The mixture was stirred for 3 hours at room temperature. The reaction mixture was poured into ice-water, which was acidified with 2N HCl. Then, resulting crystalline precipitate was collected by filtration, which was recrystallized from dichloromethane-methanol to give 3-fluoro-4-(5-methyl-2-phenyl-4-oxazolylmethoxy) nitrobenzene (14.0 g, 81%) as colorless prisms, m.p.155–156° C.

Reference Example 55

A mixture of 3-fluoro-4-(5-methyl-2-phenyl-4-oxazolylmethoxy)nitrobenzene (13.6 g), palladium-carbon (5%, 2.0 g) and tetrahydrofuran (THF) (200 ml) was subjected to catalytic hydrogenation under 1 atmospheric pressure at room temperature. The catalyst was filtered off, and the filtrate was concentrated under reduced pressure to yield 3-fluoro-4-(5-methyl-2-phenyl- 4-oxazolylmethoxy)aniline as an oily product.

NMR (δ ppm in $CDCl_3$): 2.38(3H,s), 3.53(2H,broad s), 4.96(2H,s), 6.35(1H,ddd,J=8.5&3&1.5 Hz), 6.46(1H,dd,J= 12.5&3 Hz), 6.91(1H,t,J=9 Hz), 7.35–7.5(3H,m), 7.95–8.1 (2H,m).

Reference Example 56

A solution of sodium nitrite ($NaNO_2$) (3.1 g) in water (5 ml) was added dropwise, at temperature ranging from 0 to 5° C., to a mixture of 3-fluoro-4-(5-methyl-2-phenyl-4-oxazolylmethoxy)aniline (12.3 g), aqueous HBr (47%, 28.4 g) and acetone (150 ml)-methanol (50 ml). The mixture was stirred for 25 minutes at the same temperature range, to which was added methyl acrylate (21.3 g). The mixture was heated at temperatures ranging from 30 to 35° C., to which was then added copper oxide ($Cu_2O$) (0.05 g) at the same temperature range. The whole mixture was vigorously stirred. The reaction mixture was stirred for further 30 minutes, which was then concentrated under reduced pressure. To the concentrate was added aqueous ammonia, which was subjected to extraction with ethyl acetate. The ethyl acetate layer was washed with water, which was then dried ($MgSO_4$), followed by distilling off the solvent under reduced pressure. The residue was subjected to column chromatography on silica gel. From the fraction eluted with ethyl acetate-hexane (1:4), was obtained methyl 2-bromo-3-[3-fluoro-4-(5-methyl-2-phenyl-4-oxazolylmethoxy) phenyl]propionate (14.2 g) as an oily product.

NMR (δ ppm in $CDCl_3$): 2.42(3H,s), 3.16(1H,dd,J=14&7 Hz), 3.39(1H,dd,J=14&8.5 Hz), 3.73(3H,s), 4.34(1H,dd,J= 8.5&7 Hz), 5.05(2H,s), 6.85–7.0(2H,m), 7.07(1H,t,J=8.5 Hz), 7.35–7.5(3H,m), 7.95–8.05(2H,m).

Reference Example 57

A mixture of methyl 2-bromo-3-[3-fluoro-4-(5-methyl-2-phenyl-4-oxazolylmethoxy)phenyl]propionate (14.1 g), 1,8-diazabicyclo[5.4.0]undec-7-ene (DBU) (4.8 g) and toluene (150 ml) was stirred for 2 hours at temperatures ranging from 80 to 90° C. The reaction mixture was poured into 2N HCl, which was subjected to extraction with ethyl acetate. The ethyl acetate layer was washed with water and dried ($MgSO_4$), followed by distilling off the solvent under reduced pressure to yield methyl 3-fluoro-4-(5-methyl-2-phenyl-4-oxazolylmethoxy)cinnamate (10.0 g). The product was recrystallized from dichloromethane-methanol to give colorless prisms, m.p.167–168° C.

Reference Example 58

A toluene solution of diisobutyl aluminum hydride (1.5M, 37.2 ml) was added dropwise, at 0° C., to a solution of methyl 3-fluoro-4-(5-methyl-2-phenyl-4-oxazolylmethoxy) cinnamte (9.3 g) in dichloromethane (200 ml). The mixture was stirred for 2 hours at room temperature, to which was added dropwise, under ice-cooling, 2N HCl (200 ml), followed by extraction with dichloromethane. The dichloromethane layer was washed with water, dried ($MgSO_4$) and concentrated. The concentrate was subjected to column chromatography on silica gel. From the fraction eluted with ethyl acetate-chloroform (1:5), was obtained (E)-3-[3-fluoro-4-(2-phenyl-4-oxazolylmethoxy)phenyl]-2-propen-1-ol (6.9 g, 80%), which was recrystallized from dichloromethane-isopropyl ether to yield colorless needles, m.p.134–135° C.

Reference Example 59

In substantially the same manner as in Reference Example 35, (E)-3-[3-fluoro-4-(2-phenyl-4-oxazolylmethoxy) phenyl]-2-propen-1-ol was subjected to oxidation with activated manganese dioxide to yield 3-fluoro-4-(5-methyl-2-phenyl-4-oxazolylmethoxy)cinnamaldehyde, which was recrystallized from dichloromethane-methanol to give pale yellow prisms, m.p.133–134° C.

Reference Example 60

In substantially the same manner as in Reference Example 3, 4-chloromethyl-5-methyl-2-phenyloxazole was allowed to react with isovanilline to yield 4-methoxy-3-(5-methyl-2-phenyl-4-oxazolylmethoxy)benzaldehyde, which was recrystallized from ethyl acetate-hexane to give colorless prisms, m.p.121–122° C.

Reference Example 61

In substantially the same manner as in Reference Example 16, 4-methoxy-3-(5-methyl-2-phenyl-4-oxazolyl methoxy) benzaldehyde was allowed to react with trimethyl phosphonoacetate to yield methyl 4-methoxy-3-(5-methyl-2-phenyl-4-oxazolylmethoxy)cinnamate, which was recrystallized from ethyl acetate-ether to give colorless needles, m.p.135–136° C.

Reference Example 62

In substantially the same manner as in Reference Example 24, methyl 4-methoxy-3-(5-methyl-2-phenyl-4-oxazolylmethoxy)cinnamate was subjected to reduction with diisobutyl aluminum hydride to yield (E)-3-[4-methoxy-3-(5-methyl-2-phenyl-4-oxazolylmethoxy) phenyl]-2-propen-1-ol, which was recrystallized from ethyl acetate-ether to give pale yellow prisms, m.p.137–138° C.

Reference Example 63

In substantially the same manner as in Reference Example 35, (E)-3-[4-methoxy-3-(5-methyl-2-phenyl-4-oxazolylmethoxy)phenyl]-2-propen-1-ol was subjected to oxidation with activated manganese dioxide to yield 4-methoxy-3-(5-methyl-2-phenyl-4-oxazolylmethoxy) cinnam aldehyde, which was recrystallized from ethyl acetate-ether to give pale yellow needles, m.p.136–137° C.

Reference Example 64

In substantially the same manner as in Reference Example 13, 4-[2-(2-furyl)-5-methyl-4-oxazolylmethoxy]-3-methoxybenzaldehyde was reacted with triethyl phosphonoacetate to yield ethyl 4-[2-(2-furyl)-5-methyl-4-oxazolylmethoxy]-3-methoxycinnamate, which was recrystallized from ethyl acetate. m.p.142–143° C.

Reference Example 65

In substantially the same manner as in Reference Example 47, ethyl 4-[2-(2-furyl)-5-methyl-4-oxazolyl methoxy]-3-methoxycinnamate was subjected to catalytic hydrogenation to yield ethyl 3-[4-(2-(2-furyl)-5-methyl-4-oxazolylmethoxy]-3-methoxyphenyl]propionate, which was recrystallized from ethyl acetate-hexane. m.p.88–89° C.

Reference Example 66

To a mixture of ethyl 3-[4-[2-(2-furyl)-5-methyl-4-oxazolylmethoxy]-3-methoxyphenyl]propionate (20 g), sodium borohydride (9.8 g) and tetrahydrofuran (THF) (200 ml) was added dropwise methanol (50 ml) over 2 hours under reflux. The reaction mixture was poured into water, which was subjected to extraction with ethyl acetate. The ethyl acetate layer was washed with water, dried (MgSO$_4$) and concentrated to yield 3-[4-[2-(2-furyl)-5-methyl-4-oxazolylmethoxy]-3-methoxyphenyl]propanol (15.5 g, 87%), which was recrystallized from ethyl acetate-hexane to give colorless prisms, m.p.99–100° C.

Reference Example 67

To a mixture of 3-[4-[2-(2-furyl)-5-methyl-4-oxazolylmethoxy]-3-methoxyphenyl]propanol (14.5 g), triethylamine (5.16 g) and ethyl acetate (150 ml) was added dropwise, under ice-cooling, a solution of methanesulfonyl chloride (5.8 g) in ethyl acetate (10 ml). The reaction mixture was stirred for 30 minutes at the same temperature, which was washed with water, dried (MgSO$_4$) and concentrated to yield methanesulfonic acid [3-[4-[2-(2-furyl)-5-methyl-4-oxazolylmethoxy]-3-methoxyphenyl]propyl] (16.6 g, 94%), which was recrystallized from ethyl acetate-hexane to give colorless prisms, m.p.100–101° C.

Reference Example 68

A mixture of methanesulfonic acid [3-[4-[2-(2-furyl)-5-methyl-4-oxazolylmethoxy]-3-methoxyphenyl]propyl] (16.3 g), sodium cyanide (3.9 g) and N,N-dimethylformamide (DMF) (100 ml) was stirred for 2 hours at 80° C., which was poured into water. Resulting crystalline precipitate was collected by filtration to yield 4-[4-[2-(2-furyl)-5-methyl-4-oxazolylmethoxy]-3-methoxyphenyl] butyronitrile (12.5 g, 91%), which was recrystallized from ethyl acetate-hexane to give colorless needles, m.p.94–95° C.

Reference Example 69

A mixture of 4-[4-[2-(2-furyl)-5-methyl-4-oxazolyl methoxy]-3-methoxyphenyl]butyronitrile (30.0 g), 4N KOH (150 ml) and 2-methoxyethanol (150 ml) was stirred for 2 hours under reflux. The reaction mixture was poured into ice-water, which was acidified with conc. HCl. Resulting crystalline precipitate was collected by filtration to yield 4-[4-[2-(2-furyl)-5-methyl-4-oxazolylmethoxy]-3-methoxyphenyl]butanoic acid (31.0 g, 98%), which was recrystallized from ethyl acetate to give colorless prisms, m.p.129–130° C.

Reference Example 70

A mixture of 4-[4-[2-(2-furyl)-5-methyl-4-oxazolyl methoxy]-3-methoxyphenyl]butanoic acid (106 g), isopropyl iodide (58.2 g), potassium carbonate (47.3 g) and N,N-dimethylformamide (DMF) (100 ml) was stirred for 4 hours at temperatures ranging from 65 to 70° C. The reaction mixture was poured into ice-water, which was subjected to extraction with ethyl acetate. The ethyl acetate layer was washed with water, dried (MgSO$_4$) and then concentrated. The concentrate was subjected to column chromatography on silica gel. From the fraction eluted with ethyl acetate-hexane (1:2), was obtained isopropyl 4-[4-[2-(2-furyl)-5-methyl-4-oxazolylmethoxy]-3-methoxyphenyl]butanoate (107 g, 91%), which was recrystallized from acetone-hexane to give colorless needles, m.p.45–46° C.

Reference Example 71

A solution of isopropyl 4-[4-[2-(2-furyl)-5-methyl-4-oxazolylmethoxy]-3-methoxyphenyl]butanoate (100 g) in toluene (30 ml)-N,N-dimethylformamide (DMF) (30 ml) was added dropwise, at 100° C., to a mixture of diisopropyl oxalate (84.3 g), sodium hydride (60% oil, 11.6 g) and toluene (300 ml)-N,N-dimethylformamide (DMF) (30 ml). The mixture was stirred for one hour at the same temperature, which was distributed into ice-water-2N HCl and ethyl acetate. The ethyl acetate layer separated was washed with water, dried (MgSO$_4$) and then concentrated. The concentrate was dissolved in dimethyl sulfoxide (DMSO) (400 ml)-water (40 ml), to which was added sodium chloride (14.1 g). The mixture was stirred for 10 hours at 120° C. The reaction mixture was poured into water, which was subjected to extraction with ethyl acetate. The ethyl acetate layer was washed with water, dried (MgSO$_4$) and then concentrated. The concentrate was dissolved in tetrahydrofuran (100 ml)-isopropanol (200 ml), to which was added portionwise sodium borohydride (NaBH$_4$) (1.83 g) under ice-cooling. The reaction mixture was stirred for 90 minutes at 0° C., which was poured into ice-water and acidified with 2N HCl, followed by extraction with ethyl acetate. The ethyl acetate layer was washed with water, dried (MgSO$_4$) and then concentrated. The residue was subjected to column chromatography on silica gel. From the fraction eluted with ethyl acetate-hexane (1:2), was obtained isopropyl (±)-5-[4-[2-(2-furyl)-5-methyl-4-oxazolylmethoxy]-3-methoxyphenyl]-2-hydroxypentanoate (35.1 g, 33%), which was recrystallized from ethyl acetate-hexane to give colorless prisms, m.p.75–76° C.

Reference Example 72

A 3-L flask was successively charged with isopropyl (±)-5-[4-[2-(2-furyl)-5-methyl-4-oxazolylmethoxy]-3-methoxyphenyl]-2-hydroxypentanoate (33.0 g), LIP-301 [immobilized lipase derived from Pseudomonas sp, TOYOBO CO., LTD] (16.5 g), molecular sieve 4A (33 g), toluene (1650 ml) and vinyl acetate (158 ml). The mixture was stirred for 4 hours at 23° C. The reaction mixture was subjected to filtration, and the filtrate was concentrated under reduced pressure. The concentrate was subjected to column chromatography on silica gel. From the fraction eluted with isopropyl ether, was obtained isopropyl (R)-(+)-2-acetoxy-5-[4-[2-(2-furyl)-5-methyl-4-oxazolylmethoxy]-3-methoxyphenyl]pentanoate (15.9 g). Chiral analysis of this compound by HPLC showed 96% ee.

NMR (δ ppm in CDCl$_3$): 1.22(3H,d,J=6 Hz), 1.26(3H,d, J=6 Hz), 1.6–1.95(4H,m), 2.13(3H,s), 2.40(3H,s), 2.59(2H, t,J=8 Hz), 3.86(3H,s), 4.95(1H,t,J=6 Hz), 4.95–5.15(2H,m), 5.03(2H,s), 6.52(1H,dd,J=3.5&2 Hz), 6.65–6.75(2H,m), 6.9–7.0(2H,m), 7.53(1H,dd,J=2&1 Hz). [α]$_D$+12.4° (c=2.0, 2-propanol).

From the fraction eluted subsequently, was obtained isopropyl (S)-(−)-5-[4-[2-(2-furyl)-5-methyl-4-oxazolylmethoxy]-3-methoxyphenyl]-2-hydroxypentanoate (19.7 g). The chiral analysis of this compound by HPLC showed 89% ee.

Reference Example 73

A 3 L flask was successively charged with isopropyl (S)-(−)-5-[4-[2-(2-furyl)-5-methyl-4-oxazolylmethoxy]-3-methoxyphenyl]-2-hydroxypentanoate (19.7 g) obtained in Reference Example 72, LIP-301 [immobilized lipase derived from Pseudomonas sp., TOYOBO CO.,LTD] (16.5 g) molecular sieve 4A (33 g), toluene (1650 ml) and vinyl acetate (158 ml). The mixture was stirred for 4 hours at 23° C. The reaction mixture was subjected to filtration, and the filtrate was concentrated under reduced pressure. The concentrate was subjected to column chromatography on silica gel. From the fraction eluted with isopropyl ether, was obtained isopropyl (S)-(−)-5-[4-[2-(2-furyl)-5-methyl-4-oxazolylmethoxy]-3-methoxyphenyl]-2-hydroxypentanoate (13.9 g). The chiral analysis of this compound by HPLC showed 98% ee. Recrystallization of this product from 2-propanol gave colorless prisms, m.p.90–91° C.

[α]$_D$ −2.35° (c=2. 0, 2-propanol)

Reference Example 74

Isopropyl (R)-(+)-2-acetoxy-5-[4-[2-(2-furyl)-5-methyl-4-oxazolylmethoxy]-3-methoxyphenyl]pentanoate (4.87 g) was dissolved in methanolic HCl (5%, 100 ml), which was stirred for 12 hours at room temperature. The solution was poured into water, which was subjected to extraction with ethyl acetate. The ethyl acetate layer was washed with water, dried (MgSO$_4$) and concentrated. The residue was subjected to column chromatography on silica gel. From the fraction eluted with ethyl acetate-hexane (1:1), was obtained methyl (R)-(−)-5-[4-[2-(2-furyl)-5-methyl-4-oxazolylmethoxy]-3-methoxyphenyl]-2-hydroxypentanoate (3.2 g, 77%), which was recrystallized from ethyl acetate-isopropyl ether to give colorless prisms, m.p.83–84° C.

[α]$_D$ −3.08°(c=1. 0, CHCl$_3$)

Reference Example 75

Isopropyl (S)-(−)-5-[4-[2-(2-furyl)-5-methyl-4-oxazolylmethoxy]-3-methoxyphenyl]-2-hydroxypentanoate (3.55 g) was dissolved in methanolic HCl (5%, 100 ml). The solution was stirred for 10 hours at room temperature, which was poured into water, followed by extraction with ethyl acetate. The ethyl acetate layer was washed with water, dried (MgSO$_4$) and concentrated. The residue was subjected to column chromatography on silica gel. From the fraction eluted with ethyl acetate-hexane (1:1), was obtained methyl (S)-(+)-5-[4-[2-(2-furyl)-5-methyl-4-oxazolylmethoxy]-3-methoxyphenyl]-2-hydroxypentanoate (3.03 g, 91%). Recrystallization from ethyl acetate-hexane gave colorless prisms, m.p.80–81° C. [α]$_D$ +3.03° (c=1. 0, CHCl$_3$)

Reference Example 76

To a solution of methyl (R)-(−)-5-[4-[2-(2-furyl)-5-methyl-4-oxazolylmethoxy]-3-methoxyphenyl]-2-hydroxypentanoate (3.15 g) in pyridine (50 ml) was added 4-nitrophenyl chloroformate (2.3 g), in limited amounts, at room temperature. The mixture was stirred for one hour. The reaction mixture was poured into water, which was acidified with 2N HCl, followed by extraction with ethyl acetate. The ethyl acetate layer was washed with water, dried (MgSO$_4$) and concentrated. The residue was subjected to column chromatography on silica gel. From the fraction eluted with ethyl acetate-hexane (1:2), was obtained methyl (R)-(+)-5-[4-[2-(2-furyl)-5-methyl-4-oxazolylmethoxy]-3-methoxyphenyl]-2-(4-nitrophenoxycarbonyloxy)pentanoate (4.3 g, 98%).

NMR (δ ppm in CDCl3): 1.7–2.05(4H,m), 2.41(3H,s), 2.63(2H,t,J=7 Hz), 3.81(3H,s), 3.87(3H,s), 5.03(2H,s), 5.06 (1H,t,J=6 Hz), 6.53(1H,dd,J=3.5&2 Hz), 6.65–6.75(2H,m), 6.9–7.0(2H,m), 7.41(2H,d,J=9 Hz), 7.54(1H,dd,J=2&1 Hz), 8.29(2H,d,J=9 Hz).

[α]$_D$ +8.06° (c=1.0, CHCl$_3$).

Reference Example 77

In substantially the same manner as in Reference Example 76, from methyl (S)-(+)-5-[4-[2-(2-furyl)-5-methyl-4-oxazolylmethoxy]-3-methoxyphenyl]-2-hydroxypentanoate, was obtained methyl (S)-(−)-5-[4-[2-(2-furyl)-5-methyl-4-oxazolylmethoxy]-3-methoxyphenyl]-2-(4-nitrophenoxycarbonyloxy)pentanoate. [α]$_D$ −8.09° (c=1. 0, CHCl$_3$)

Reference Example 78

Into a tetrahydrofuran (THF) (80 ml) solution of methyl (R)-(+)-5-[4-[2-(2-furyl)-5-methyl-4-oxazolyl methoxy]-3-methoxyphenyl]-2-(4-nitrophenoxycarbonyloxy)pentanoate (4.25 g) was introduced ammonia (gas) for 10 minutes at temperature ranging from −65 to −70° C. The reaction mixture was poured into water-6N HCl, which was subjected to extraction with ethyl acetate. The ethyl acetate layer was washed with water, dried (MgSO$_4$) and concentrated. The residue was subjected to column chromatography on silica gel. From the fraction eluted with ethyl acetate-hexane (1:1), was obtained methyl (R)-(+)-2-carbamoyloxy-5-[4-[2-(2-furyl)-5-methyl-4-oxazolylmethoxy]-3-methoxyphenyl]pentanoate (3.0 g, 89%), which was recrystallized from acetone-isopropyl ether to give colorless needles, m.p.110–111° C. [α]$_D$ +5.30° (c=1. 0, CH$_3$OH)

Reference Example 79

In substantially the same manner as in Reference Example 78, from methyl (S)-(−)-5-[4-[2-(2-furyl)-5-methyl-4-oxazolylmethoxy]-3-methoxyphenyl]-2-(4- nitrophenoxycarbonyloxy)pentanoate, was obtained methyl (S)-(-)-2-carbamoyloxy-5-[4-[2-(2-furyl)-5-methyl-4-oxazolylmethoxy]-3-methoxyphenyl]pentanoate, which was recrystallized from acetone-isopropyl ether to give colorless needles, m.p.110–111° C. [α]$_D$ –5.41° (c=1. 0, CH$_3$OH)

Reference Example 80

A solution of n-butyl lithium in hexane (1.6 M, 15.6 ml) was added dropwise, at –15° C., to a mixture of (1,3-dioxolan-2-ylmethyl)triphenylphosphonium bromide (10.74 g) and tetrahydrofuran (110 ml). The mixture was stirred for 1 hour at the same temperature, to which was added 3-methoxy-4-(5-methyl-2-phenyl-4-oxazolylmethoxy) benzaldehyde (6.74 g). After being stirred for 4 hours at 50° C., the reaction mixture was poured into ice-water, which was subjected to extraction with ethyl acetate. The ethyl acetate layer was washed successively with 0.1 N HCl, water and a saturated saline solution, and dried (MgSO$_4$), followed by distilling off the solvent. The residual oily product was subjected to column chromatography on silica gel. From the fraction eluted with ethyl acetate-hexane (1:2, v/v), was obtained 2-[2-[3-methoxy-4-(5-methyl-2-phenyl-4-oxazolylmethoxy)phenyl]vinyl]-1,3-dioxolane (4.84 g) as an oily product. This oily product (4.84 g) was dissolved in tetrahydrofuran (90 ml). To the solution was added palladium-carbon (5%, 50% wet, 1.8 g), which was subjected to catalytic hydrogenation at room temperature under 1 atmospheric pressure. The catalyst was filtered off, and the filtrate was concentrated. The resulting oily product was subjected to column chromatography on silica gel. From the fraction eluted with ethyl acetate-hexane (1:3, v/v), was obtained 2-[2-[3-methoxy-4-(5-methyl-2-phenyl-4-oxazolylmethoxy)phenyl]ethyl]-1,3-dioxolane (3.03 g, 37%), which was recrystallized from ethyl acetate-hexane to give colorless needles, m.p.90–91° C.

Reference Example 81

A mixture of 2-[2-[3-methoxy-4-(5-methyl-2-phenyl-4-oxazolylmethoxy)phenyl]ethyl]-1.3-dioxolane (2.73 g) and an aqueous solution of acetic acid (50%, 75 ml) was stirred for 3 hours at 80° C. The reaction mixture was concentrated under reduced pressure. The residue was poured into water and made alkaline with potassium carbonate, followed by extraction with ethyl acetate. The ethyl acetate layer was washed with water and dried (MgSO$_4$), followed by distilling off the solvent to yield 3-[3-methoxy-4-(5-methyl-2-phenyl-4-oxazolylmethoxy)phenyl]propionaldehyde (2.09 g, 86%). The product was recrystallized from ethyl acetate-hexane to give colorless needles, m.p.85–86° C.

Reference Example 82

A mixture of 3-[3-methoxy-4-(5-methyl-2-phenyl-4-oxazolylmethoxy)phenyl]propionaldehyde (1.79 g), sodium cyanide (0.3 g), acetic anhydride (0.62 g), benzyltributylammonium chloride (0.79 g), water (12 ml) and dichloromethane (35 ml) was stirred for 15 hours at room temperature. The organic layer was separated, which was washed with water and dried (MgSO$_4$), followed by distilling off the solvent. The resulting oily product was subjected to column chromatography on silica gel. From the fraction eluted with ethyl acetate-hexane (1:3, v/v), was obtained 2-acetoxy-4-[3-methoxy-4-(5-methyl-2-phenyl-4-oxazolylmethoxy)phenyl]butyronitrile (2.0 g, 94%), NMR(δ ppm in CDCl$_3$): 2.14(3H,s), 2.12–2.31(2H,m), 2.41(3H,s), 2.78(2H,t,J=8 Hz), 3.87(3H,s), 5.04(2H,s), 5.27 (1H,t,J=7 Hz), 6.70(1H,dd,J=8&2 Hz), 6.71(1H,d,J=2 Hz), 7.00(1H,d,J=9 Hz), 7.42–7.47(3H,m), 7.99–8.04(2H,m)

Reference Example 83

A mixture of 2-acetoxy-4-[3-methoxy-4-(5-methyl-2-phenyl-4-oxazolylmethoxy)phenyl]butyronitrile (2.0 g), 6 N HCl (24 ml) and dioxane (12 ml) was stirred for 4 hours under reflux. The reaction mixture was poured into water, which was subjected to extraction with ethyl acetate. The ethyl acetate layer was washed with water and dried (MgSO$_4$), followed by distilling off the solvent. To the resulting oily product was added ethanolic hydrochloric acid (10%, 24 ml), followed by stirring for 1.5 hours under reflux. The reaction mixture was poured into water, which was subjected to extraction with ethyl acetate. The ethyl acetate layer was washed with water, dried (MgSO$_4$), followed by distilling off the solvent. The resulting oily product was subjected to column chromatography on silica gel. From the fraction eluted with ethyl acetate-hexane (1:2, v/v), was obtained ethyl 2-hydroxy-4-(4-hydroxy-3-methoxyphenyl) butanoate (0.73 g, 60%), NMR(δ ppm in CDCl$_3$): 1.29(3H,t,J=7 Hz), 1.81–2.17 (2H,m), 2.70(2H,t,J=8 Hz), 2.84(1H,d,J=5 Hz), 3.88(3H,s), 4.13–4.19(1H,m), 4.22(2H,q,J=7 Hz), 5.50(1H,s), 6.70(1H, dd,J=7&2 Hz), 6.72(1H,s), 6.84(1H,d,J=9 Hz)

Reference Example 84

A mixture of ethyl 2-hydroxy-4-(4-hydroxy-3-methoxyphenyl)butanoate (0.73 g), potassium cyanate (KCNO) (0.7 g) and butanol (25 ml) was stirred for 18 hours under reflux. The reaction mixture was concentrated under reduced pressure. The residue was poured into water and acidified with 2N HCl, followed by extraction with ethyl acetate. The ethyl acetate layer was washed with water and dried (MgSO$_4$), followed by distilling off the solvent. The resulting oily product was subjected to column chromatography on silica gel. From the fraction eluted with ethyl acetate-chloroform (1:4, v/v), was obtained 5-[2-(4-hydroxy-3-methoxyphenyl)ethyl]-2,4-oxazolidinedione (0.2 g, 28%), NMR(δ ppm in CDCl$_3$): 2.12–2.16(2H,m), 2.73–2.83(2H, m), 3.89(3H,s), 4.80(1H,dd,J=8&5 Hz), 5.53(1H,s), 6.70 (1H,d,J=2 Hz), 6.72(1H,dd,J=7&2 Hz), 6.86(1H,d,J=9 Hz), 8.21(1H,br s)

Reference Example 85

Sodium borohydride (1.41 g) was added portionwise, at 0° C., to a solution of 4-acetyl-5-methyl-2-phenyloxazole (15.0 g) in ethanol (100 ml). The mixture was stirred for 1 hour at the same temperature, and then for 1 hour at room temperature. The reaction mixture was poured into water, which was neutralized with 2N HCl to obtain 1-(5-methyl-2-phenyl-4-oxazolyl)ethanol (13.0 g, 86%), which was recrystallized from ethyl acetate-hexane to give colorless prisms, m.p.101–102° C.

Reference Example 86

Diethyl azodicarboxylate (DEAD) (4.71 g) was added dropwise, under ice-cooling, to a mixture of 1-(5-methyl-2-phenyl-4-oxazolyl)ethanol (5.0 g), vanilline (3.75 g), triphenylphosphine (Ph$_3$P) (7.1 g) and tetrahydrofuran (THF) (80 ml). The reaction mixture was stirred for 8 hours at room temperature and concentrated under reduced pressure. The residue was subjected to column chromatography on silica gel. From the fraction eluted with ethyl acetate-hexane (1:4, v/v), was obtained 3-methoxy-4-[1-(5-methyl-2-phenyl-4-oxazolyl)ethoxy]benzaldehyde (4.48 g, 54%), which was recrystallized from ethyl acetate-hexane to give colorless needles, m.p.104–105° C.

Reference Example 87

In substantially the same manner as in Reference Example 13, 3-methoxy-4-[1-(5-methyl-2-phenyl-4-oxazolyl)ethoxy] benzaldehyde was reacted with triethyl phosphonoacetate to yield ethyl 3-methoxy-4-[1-(5-methyl-2-phenyl-4-oxazolyl) ethoxy]cinnamate, which was recrystallized from acetone-isopropyl ether to give colorless needles, m.p.121–122° C.

Reference Example 88

In substantially the same manner as in Reference Example 24, ethyl 3-methoxy-4-[1-(5-methyl-2-phenyl-4-oxazolyl) ethoxy]cinnamate was subjected to reduction reaction with diisobutylaluminum hydride to yield (E)-3-[3-methoxy-4-[1-(5-methyl-2-phenyl-4-oxazolyl)ethoxy]phenyl]-2-propen-1-ol.

NMR($\delta$ ppm in CDCl$_3$): 1.44(1H,br t,J=6.5 Hz), 1.75(3H, d,J=6.5 Hz), 2.28(3H,s), 3.88(3H,s), 4.25–4.35(2H,m), 5.37 (1H,q,J=6.5 Hz), 6.23(1H,dt,J=16&6 Hz), 6.52(1H,dt,J= 16&1.5 Hz), 6.8–6.95(3H,m), 7.35–7.5(3H,m), 7.95–8.05 (2H,m)

Reference Example 89

In substantially the same manner as in Reference Example 35, (E)-3-[3-methoxy-4-[1-(5-methyl-2-phenyl-4-oxazolyl) ethoxy]phenyl]-2-propen-1-ol was subjcted to oxidation reaction with activated manganese dioxide to yield 3-methoxy-4-[1-(5-methyl-2-phenyl-4-oxazolyl)ethoxy] cinnamaldehyde, which was recrystallized from acetone-isopropyl ether to give colorless needles, m.p.152–153° C.

Reference Example 90

Sodium hydride (60% in oil, 8.43 g) was added portionwise, at 0° C., to a solution of 4-benzyloxy-3-methoxybenzaldehyde (46.4 g) and triethyl phosphonocrotonate (50.3 g) in N,N-dimethylformamide (DMF) (190 ml). The mixture was stirred for 15 hours at room temperature, which was poured into 1N HCl (1 L), followed by extraction with ethyl acetate. The ethyl acetate layer was washed with water and dried (MgSO$_4$), followed by distilling off the solvent. The resulting oily product was subjected to column chromatography on silica gel. From the fraction eluted with ethyl acetate-hexane (1:3, v/v), was obtained ethyl (E,E)-5-(4-benzyloxy-3-methoxyphenyl)-2,4-pentadienoate (38.3 g, 59%), which was recrystallized from ethyl acetate-hexane to give pale yellow needles, m.p.85–86° C.

Reference Example 91

In substantially the same manner as in Reference Example 47, ethyl (E,E)-5-(4-benzyloxy-3-methoxyphenyl)-2,4-pentadienate was subjected to catalytic reduction to yield ethyl 5-(4-hydroxy-3-methoxyphenyl)pentanoate.

NMR($\delta$ ppm in CDCl$_3$): 1.25(3H,t,J=7 Hz), 1.61–1.66 (4H,m), 2.32(2H,t,J=7 Hz), 2.56(2H,t,J=7 Hz), 3.88(3H,s), 4.12(2H,q,J=7 Hz), 5.46(1H,s), 6.66(1H,dd,J=8&2 Hz), 6.83(1H,d,J=9 Hz)

Reference Example 92

A mixture of ethyl 5-(4-hydroxy-3-methoxyphenyl) pentanoate (27.92 g), benzyl bromide (20.82 g), potassium carbonate (22.9 g) and N,N-dimethylformamide (DMF) (140 ml) was stirred for 15 hours at 90° C. The reaction mixture was concentrated under reduced pressure. The residue was subjected to column chromatography on silica gel. From the fraction eluted with ethyl acetate-hexane (1:6, v/v), was obtained ethyl 5-(4-benzyloxy-3-methoxyphenyl) pentanoate (31.64 g, 84%), NMR($\delta$ ppm in CDCl$_3$): 1.25(3H,t,J=7 Hz), 1.61–1.66 (4H,m), 2.32(2H,t,J=7 Hz), 2.56(2H,t,J=7 Hz), 3.88(3H,s), 4.12(2H,q,J=7 Hz), 5.12(2H,s), 6.64(1H,dd,J=8&2 Hz), 6.72(1H,d,J=2 Hz), 6.80(1H,d,J=8 Hz), 7.28–7.47(5H,m)

Reference Example 93

In substantially the same manner as in Reference Example 71, ethyl 5-(4-benzyloxy-3-methoxyphenyl)pentanoate was condensed with diethyl oxalate. The product was subjected to decarboxylation reaction, which was then subjected to reduction with sodium borohydride to yield ethyl 6-(4-benzyloxy-3-methoxyphenyl)-2-hydroxyhexanoate.

NMR($\delta$ ppm in CDCl$_3$): 1.27(3H,t,J=7 Hz), 1.43–1.79 (6H,m), 2.55(2H,t,J=8 Hz), 2.73(1H,d,J=6 Hz), 3.88(3H,s), 4.12–4.17(1H,m), 4.23(2H,q,J=7 Hz), 5.12(2H,s), 6.63(1H, dd,J=8&2 Hz), 6.72(1H,d,J=2 Hz), 6.79(1H,d,J=8 Hz), 7.26–7.46(5H,m)

Reference Example 94

In substantially the same manner as in Reference Example 47, 5-[4-(4-benzyloxy-3-methoxyphenyl)butyl]-2,4-oxazolidinedione was subjected to catalytic reduction to yield 5-[4-(4-hydroxy-3-methoxyphenyl)butyl]-2,4-oxazolidinedione. The product was recrystallized from ethyl acetate-hexane to give colorless prisms, m.p.115–116° C.

Reference Example 95

In substantially the same manner as in Reference Example 13, 4-benzyloxy-3-ethoxybenzaldehyde was reacted with triethyl phosphonoacetate to yield ethyl 4-benzyloxy-3-methoxycinnamate. The product was recrystallized from isopropyl ether-hexane to give colorless needles, m.p.74.5–75° C.

Reference Example 96

In substantially the same manner as in Reference Example 47, ethyl 4-benzyloxy-3-methoxycinnamate was subjected to catalytic hydrogenation to yield ethyl 3-(3-ethoxy-4-hydroxyphenyl)propionate.

NMR($\delta$ ppm in CDCl$_3$): 1.24(3H,t,J=7 Hz), 1.44(3H,t,J=7 Hz), 2.57(2H,t,J=7.7 Hz), 2.87(2H,t,J=7.7 Hz), 4.09(2H,q, J=7 Hz), 4.13(2H,q,J=7 Hz), 5.54(1H,s), 6.69(1H,d,J=8.4 Hz), 6.70(1H,s), 6.84(1H,d,J=8.4 Hz)

Reference Example 97

In substantially the same manner as in Reference Example 92, 3-(3-ethoxy-4-hydroxyphenyl)propionate was reacted with benzyl bromide to yield 3-(4-benzyloxy-3-ethoxyphenyl)propionate.

NMR($\delta$ ppm in CDCl$_3$): 1.23(3H,t,J=7 Hz), 1.45(3H,t,J=7 Hz), 2.58(2H,t,J=7.6 Hz), 2.87(2H,t,J=7.6 Hz), 4.09(2H,q, J=7 Hz), 4.12(2H,q,J=7 Hz), 5.11(2H,s), 6.66(1H,dd,J= 8.3&1.9 Hz), 6.76(1H,d,J=1.9 Hz), 6.82(1H,d,J=8.3 Hz), 7.23–7.61(5H,m)

Reference Example 98

In substantially the same manner as in Reference Example 93, 3-(4-benzyloxy-3-ethoxyphenyl)propionate was processed to yield 4-(4-benzyloxy-3-ethoxyphenyl)-2-hydroxybutanoate. The product was recrystallized from ethyl acetate-isopropyl ether-hexane to give colorless needles, m.p.62–63° C.

Reference Example 99

In substantially the same manner as in Reference Example 47, 5-[2-(4-benzyloxy-3-ethoxyphenyl)ethyl]-2,4-oxazolidinedione was subjected to catalytic hydrogenation to yield 5-[2-(4-hydroxy-3-ethoxyphenyl)ethyl]-2,4-oxazolidinedione. The product was recrystallized from ethyl acetate-hexane to give colorless prisms, m.p.154.5–155° C.

Reference Example 100

In substantially the same manner as in Reference Example 13, 3-benzyloxy-4-methoxybenzaldehyde was reacted with triethylphosphonoacetate to yield ethyl 4-benzyloxy-3-methoxycinnamate. The product was recrystallized from ether-hexane to give colorless needles, m.p.95–96° C.

Reference Example 101

In substantially the same manner as in Reference Example 47, ethyl 4-benzyloxy-3-methoxycinnamate was subjected to catalytic hydrogenation to yield ethyl 3-(3-hydroxy-4-methoxyphenyl)propionate.

NMR($\delta$ ppm in $CDCl_3$): 1.24(3H,t,J=7 Hz), 2.57(2H,t,J=7.6 Hz), 2.86(2H,t,J=7.6 Hz), 3.86(3H,s), 4.13(2H,q,J=7.2 Hz), 5.58(1H,s), 6.68(1H,dd,J=8.2&2 Hz), 6.77(1H,d,J=8.2 Hz), 6.78(1H,d,J=2 Hz)

Reference Example 102

In substantially the same manner as in Reference Example 92, ethyl 3-(3-hydroxy-4-methoxyphenyl)propionate was reacted with benzyl bromide to yield ethyl 3-(3-benzyloxy-4-methoxyphenyl)propionate. The product was recrystallized from hexane to give colorless needles, m.p.49.5–50.5° C.

Reference Example 103

In substantially the same manner as in Reference Example 93, ethyl 3-(3-benzyloxy-4-methoxyphenyl)propionate was processed to yield ethyl 4-(3-benzyloxy-4-methoxyphenyl)-2-hydroxybutanoate. The product was recrystallized from ethyl acetate-hexane to give colorless needles, m.p.93–94° C.

Reference Example 104

In substantially the same manner as in Reference Example 47, 5-[2-(3-benzyloxy-4-methoxyphenyl)ethyl]-2,4-oxazolidinedione was subjected to catalytic hydrogenation to yield 5-[2-(3-hydroxy-4-methoxyphenyl)ethyl]-2,4-oxazolidinedione. The product was recrystallized from isopropyl ether-hexane to give colorless prisms, m.p.121–122° C.

Reference Example 105

In substantially the same manner as in Reference Example 92, syringaaldehyde was reacted with benzyl bromide to yield 4-benzyloxy-3,5-dimethoxybenzaldehyde. The product was recrystallized from ethyl acetate-hexane to give colorless prisms, m.p.65–66° C.

Reference Example 106

In substantially the same manner as in Reference Example 13, 4-benzyloxy-3,5-dimethoxybenzaldehyde was reacted with triethyl phosphonoacetate to yield ethyl 4-benzyloxy-3,5-dimethoxycinnamate. The product was recrystallized from ether-hexane to give colorless plates, m.p.68–69° C.

Reference Example 107

In substantially the same manner as in Reference Example 34, ethyl 4-benzyloxy-3,5-dimethoxycinnamate was subjected to catalytic hydrogenation to yield (E)-3-(4-benzyloxy-3,5-dimethoxyphenyl)-2-propen-1-ol. The product was recrystallized from ethyl acetate-hexane to give colorless needles, m.p.72–73° C.

Reference Example 108

In substantially the same manner as in Reference Example 35, (E)-3-(4-benzyloxy-3,5-dimethoxyphenyl)-2-propen-1-ol was subjected to oxidation reaction with activated manganese dioxide to yield 4-benzyloxy-3,5-dimethoxycinnamaldehyde. The product was recrystallized from ethyl acetate-hexane to give colorless plates, m.p.114–115° C.

Reference Example 109

In substantially the same manner as in Reference Example 47, 5-[3-(4-benzyloxy-3,5-dimethoxy)cinnamilidene]-2,4-oxazolidinedione was subjected to catalytic hydrogenation to yield 5-[3-(4-hydroxy-3,5-dimethoxyphenyl)propyl]-2,4-oxazolidinedione. The product was recrystallized from ethanol-hexane to give colorless prisms, m.p.155–156° C.

Reference Example 110

In substantially the same manner as in Reference Example 54, 3,4-difluoronitrobenzene was reacted with 2-[N-methyl-N-(2-pyridyl)amino]ethanol to yield 3-fluoro-4-[2-[N-methyl-N-(2-pyridyl)amino]ethoxy]nitrobenzene. The product was recrystallized from ethyl acetate-hexane to give yellow prisms, m.p.95–96° C.

Reference Example 111

In substantially the same manner as in Reference Example 55, 3-fluoro-4-[2-[N-methyl-N-(2-pyridyl)amino]ethoxy]nitrobenzene was subjected to catalytic hydrogenation to yield 3-fluoro-4-[2-[N-methyl-N-(2-pyridyl)amino]ethoxyaniline as an oily product.

NMR($\delta$ ppm in $CDCl_3$): 3.15(3H,s), 3.40–3.55(2H,brs), 3.96(2H,t,J=5.4 Hz), 4.16(2H,t,J=5.4 Hz), 6.30–6.37(1H,m), 6.41–6.58(3H,m), 6.73–6.83(1H,m), 7.40–7.50(1H,m), 8.12–8.17(1H,m)

Reference Example 112

In substantially the same manner as in Reference Example 56, 3-fluoro-4-[2-[N-methyl-N-(2-pyridyl)amino]ethoxy]aniline was processed to yield methyl 2-bromo-3-[3-fluoro-4-[2-[N-methyl-N-(2-pyridyl)amino]ethoxy]phenyl]propionate as an oily product.

NMR($\delta$ ppm in $CDCl_3$): 3.14(1H,dd,J=7.0&14.0 Hz), 3.15(3H,s), 3.37(1H,dd,J=8.2&14.0 Hz), 3.73(3H,s), 4.00(2H,t,J=5.4 Hz), 4.23(2H,t,J=5.4 Hz), 4.32(1H,dd,J=7.0&8.2 Hz), 6.49–6.58(2H,m), 6.86–6.96(3H,m), 7.45(1H,ddd,J=1.8,6.8&8.8 Hz), 8.12–8.16(1H,m)

Reference Example 113

In substantially the same manner as in Reference Example 57, methyl 2-bromo-3-[3-fluoro-4-[2-[N-methyl-N-(2-pyridyl)amino]ethoxy]phenyl]propionate was processed to yield methyl 3-fluoro-4-[2-[N-methyl-N-(2-pyridyl)amino]ethoxy]cinnamate. The product was recrystallized from ethyl acetate-hexane to give colorless prisms, m.p.110–111° C.

Reference Example 114

In substantially the same manner as in Reference Example 58, methyl 3-fluoro-4-[2-[N-methyl-N-(2-pyridyl)amino]ethoxy]cinnamate was subjected to reduction reaction with diisobutylaluminum hydride to yield (E)-3-(3-fluoro-4-[2-[N-methyl-N-(2-pyridyl)amino]ethoxy]phenyl]-2-propen-1-ol. The product was recrystallized from ethyl acetate-hexane to give colorless needles, m.p.80–81° C.

Reference Example 115

In substantially the same manner as in Reference Example 35, (E)-3-[3-fluoro-4-[2-[N-methyl-N-(2-pyridyl)amino]ethoxy]phenyl]-2-propen-1-ol was subjected to oxidation reaction with activated manganese dioxide to yield 3-fluoro-4-[2-[N-methyl-N-(2-pyridyl)amino]ethoxy] cinnamaldehyde, which was recrystallized from ethyl acetate-hexane to give colorless needles, m.p.93–94° C.

What is claimed is:

1. A 2,4-oxazolidinedione compound of the formula:

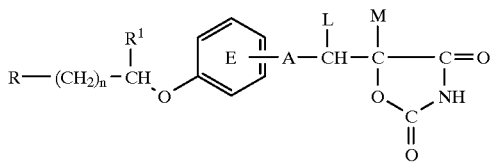

wherein:

R stands for an oxazolyl group which may have 1 to 2 substituents selected from the group consisting of:
  (1) aliphatic chain hydrocarbon group;
  (2) alicyclic hydrocarbon group;
  (3) aryl group;
  (4) aromatic heterocyclic group selected from the group consisting of furyl and thienyl;
  (5) halogen atom;
  (6) nitro group;
  (7) amino group which is unsubstituted or substituted by 1 or 2 substituents selected from the group consisting of $C_{1-10}$ alkyl, $C_{2-10}$ alkenyl, $C_{1-10}$ acyl and phenyl;
  (8) acyl group selected from formyl, $C_{1-10}$ alkyl-carbonyl, $C_{2-10}$ alkenyl-carbonyl or benzoyl, which is unsubstituted or substituted by a substituent selected from the group consisting of $C_{1-3}$ alkyl, $C_{1-3}$ alkoxy, halogen, nitro, hydroxy and amino;
  (9) hydroxyl, $C_{6-14}$ aryloxy, $C_{1-10}$ alkoxy, $C_{2-10}$ alkenyloxy, phenyl-$C_{1-4}$ alkyloxy and $C_{2-4}$ alkanoyloxy group;
  (10) thiol, $C_{1-10}$ alkylthio, phenyl-$C_{1-4}$ alkylthio and $C_{2-4}$ alkanoylthio;
  (11) carboxyl, $C_{2-5}$ alkoxycarbonyl, $C_{8-10}$ aralkyloxycarbonyl and $C_{7-15}$ aryloxycarbonyl group;
  (12) styryl;
  (13) phenylethyl; and
  (14) naphthylethenyl;
  wherein each of the above substituents (2), (3) and (4) may be substituted by 1 to 3 substituents selected from the group consisting of:
  1) lower alkyl group;
  2) lower alkenyl group;
  3) lower alkynyl group;
  4) cycloalkyl group;
  5) aryl group;
  6) aromatic heterocyclic group selected from the group consisting of thienyl and furyl;
  7) $C_{7-9}$ aralkyl group;
  8) amino group;
  9) N-mono($C_{1-4}$)alkylamino group;
  10) N,N-di($C_{1-4}$)alkylamino group;
  11) acylamino group selected from the group consisting of acetylamino, propionylamino and benzoylamino;
  12) amidino group;
  13) $C_{2-8}$ acyl group;
  14) carbamoyl group;
  15) N-mono ($C_{1-4}$)alkyl carbamoyl group;
  16) N,N-di ($C_{1-4}$) alkyl carbamoyl group;
  17) sulfamoyl group;
  18) N-mono ($C_{1-4}$) alkyl sulfamoyl group;
  19) N,N-di($C_{1-4}$)alkyl sulfamoyl group;
  20) carboxyl group;
  21) lower alkoxycarbonyl group;
  22) hydroxyl group;
  23) lower alkoxy group;
  24) lower alkenyloxy group;
  25) cycloalkyloxy group;
  26) $C_{7-9}$ aralkyloxy group;
  27) aryloxy group selected from the group consisting of phenyloxy and naphthyloxy;
  28) mercapto group;
  29) lower alkylthio group;
  30) $C_{7-9}$ aralkylthio group;
  31) arylthio group selected from the group consisting of phenylthio and naphthylthio;
  32) sulfo group;
  33) cyano group;
  34) azido group;
  35) nitro group;
  36) nitroso group; and
  37) halogen;

n is 0, 1 or 2;

A stands for —$CH_2CH_2$—;

$R^1$ stands for hydrogen or an alkyl group;

ring E stands for a benzene ring having 1 or 2 substituents selected from the group consisting of hydroxyl, $C_{6-14}$ aryloxy, $C_{1-10}$ alkoxy, $C_{2-10}$ alkenyloxy, phenyl-$C_{1-4}$ alkyloxy and $C_{2-4}$ alkanoyloxy group;

L and M respectively each stand for hydrogen, or a pharmaceutically acceptable salt thereof.

2. A compound according to claim 1, which is (R)-(+)-5-[3-[4-[2-(2-furyl)-5-methyl-4-oxazolylmethoxy]-3-methoxyphenyl]propyl]-2,4-oxazolidinedione.

3. A compound according to claim 1, which is 5-[3-[3-fluoro-4-(5-methyl-2-phenyl-4-oxazolylmethoxy)phenyl]propyl]-2,4-oxazolidinedione.

4. A compound according to claim 1, which is 5-[3-[3,5-dimethoxy-4-[2-[(E)-styryl]-4-oxazolylmethoxy]phenyl]propyl]-2,4-oxazolidinedione.

5. A method for treating diabetes in a mammal in need thereof, which comprises administering to said mammal a therapeutically effective amount of a compound or a pharmaceutically acceptable salt thereof as defined in claim 1.

6. Method for treating hyperlipemia in a mammal in need thereof, which comprises administering to said mammal a therapeutically effective amount of a compound or a pharmaceutically acceptable salt thereof as defined in claim 1.

7. A compound according to claim 1, wherein the partial formula:

represents the formula:

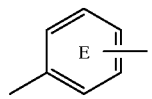

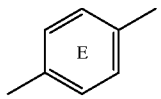

8. A pharmaceutical composition comprising a 2,4-oxazolidinedione compound or a pharmaceutically acceptable salt thereof according to claim 1, together with a pharmaceutically acceptable carrier, diluent or excipient.

9. A pharmaceutical composition according to claim 8, which is for lowering blood sugar.

10. A pharmaceutical composition according to claim 8, which is for lowering lipid in blood.

11. A pharmaceutical composition according to claim 8, which is a therapeutic agent of diabetes.

12. A pharmaceutical composition according to claim 8, which is a therapeutic agent of hyperlipemia.

13. A compound according to claim 1, wherein the partial formula:

represents the formula:

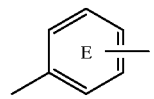

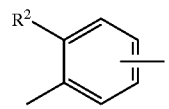

, and wherein $R^2$ stands for hydroxyl, $C_{6-14}$ aryloxy, $C_{1-10}$ alkoxy, $C_{2-10}$ alkenyloxy, phenyl-$C_{1-4}$ alkyloxy or $C_{2-4}$ alkanoyloxy group.

14. A compound according to claim 10, wherein $R^2$ is a $C_{1-4}$ alkoxy group.

15. A compound according to claim 10, wherein n is 0 or 1; and $R^2$ is a $C_{1-4}$ alkoxy group.

16. A compound according to claim 15, wherein R is an oxazolyl group which is unsubstituted or substituted by phenyl, naphthyl, furyl, thienyl or $C_{1-3}$ alkyl group.

17. A compound according to claim 1, wherein n is 0.

* * * * *